(12) United States Patent
Allanson et al.

(10) Patent No.: US 6,207,820 B1
(45) Date of Patent: Mar. 27, 2001

(54) COMBINATORIAL LIBRARY OF MOENOMYCIN ANALOGS AND METHODS OF PRODUCING SAME

(75) Inventors: Nigel Mark Allanson, Princeton; Tin Yau Chan, Edison; Nicole T. Hatzenbuhler, Bridgewater; Rakesh K. Jain, Lawrenceville; Ramesh Kakarla, East Brunswick; Rui Liang, Plainsboro; Dashan Liu, East Brunswick; Domingos J. Silva, Plainsboro; Michael J. Sofia, Lawrenceville, all of NJ (US)

(73) Assignee: Incara Research Laboratories, Cranbury, NJ (US)

(*) Notice: Subject to any disclaimer, the term of this patent is extended or adjusted under 35 U.S.C. 154(b) by 0 days.

(21) Appl. No.: 09/394,045

(22) Filed: Sep. 13, 1999

Related U.S. Application Data

(62) Division of application No. 08/975,229, filed on Nov. 21, 1997.

(51) Int. Cl.$^7$ .................................................. C07H 1/00
(52) U.S. Cl. .................. 536/126; 536/18.5; 536/18.6; 536/124
(58) Field of Search .......................... 536/4, 18.5, 18.6, 536/124, 126

(56) References Cited

U.S. PATENT DOCUMENTS

| | | |
|---|---|---|
| 3,674,866 | 7/1972 | Lindner et al. . |
| 4,684,626 | 8/1987 | Welzel et al. . |
| 5,206,206 | 4/1993 | Buelna et al. . |
| 5,206,405 | 4/1993 | Aretz et al. . |
| 5,315,038 | 5/1994 | Aretz et al. . |
| 5,316,929 | 5/1994 | Aretz et al. . |
| 5,506,140 | 4/1996 | Aretz et al. . |

FOREIGN PATENT DOCUMENTS 0 655 249    11/1994    (EP) .

OTHER PUBLICATIONS

Scherkenbeck, J., et al., *Tetrahedron*, 49:3091–3100 (1993).
Heuer, M. et al., *Tetrahedron*, 50:2029–2045 (1994).
Fehlhaber, H.W., et al., *Tetrahedron*, 46:1557–1568 (1990).
Hessler–Klintz, M., et al., *Tetrahedron*, 49:7667–7678 (1993).
Welzel, P., et al., *Tetrahedron*, 43:585–598 (1987).
Moller, R., et al., *Tetrahedron*, 49:1635–1648 (1993).
Marzian, S., et al., *Tetrahedron*, 50:5299–5308 (1994).
Donnerstag, A., et al., *Tetrahedron*, 51:1931–1940 (1995).
Ritzeler, O., et al., *Tetrahedron*, 53:1675–1694 (1997a).
Ritzeler, O., et al., *Tetrahedron*, 53:1675–1694 (1997b).
Range, G., et al., *Tetrahedron*, 53:1695–1706 (1997).

*Primary Examiner*—Elli Peselev
(74) *Attorney, Agent, or Firm*—Gilberto M. Villacorta; Corinne M. Pouliquen; Pepper Hamilton LLP

(57) ABSTRACT

A combinatorial chemical library of compounds structurally related to the moenomycin class of antibiotics has the formula

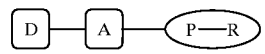

wherein D is a donor mono- or disaccharide, A is an acceptor monosaccharide, and P—R is a lipophosphoglycerate mimetic group. Members of the library have a glycosidic linkage between the anomeric carbon of D and the C2 carbon of A, and the D—A moiety is in turn covalently linked through the anomeric carbon of A to the P—R group. Members of the library exhibit their greatest structural diversity in terms of substitutions occurring at the C3 position of the A residue, substitutions at the C2 position of the D residue, and different P—R groups used in assembling the compounds. Members of the library are preferably synthesized by solid phase techniques involving stepwise coupling of the respective units to a support, functionalizing the A and/or D saccharides either before or after immobilizing them on the support, and cleaving the assembled compounds from the support. Preferred functionalities attached to the sugar residues are amides, carbamates, ureas, sulfonamides, substituted amines, esters, carbonates, and sulfates. Exemplary P—R groups are derivatives of homoserine, glyceric acid, salicylates and mandelic acid. Members of the library can be screened for anti-microbial activity by contacting them with a culture of microbes and monitoring the growth rate of the microbes.

6 Claims, 20 Drawing Sheets

Scheme 1

Scheme 4

Scheme 7

Scheme 9

Scheme 10

Scheme 15

Scheme 17

Scheme 18

Scheme 20

Scheme 21

Scheme 21 (cont'd)

COMBINATORIAL LIBRARY OF MOENOMYCIN ANALOGS AND METHODS OF PRODUCING SAME

RELATED APPLICATIONS

This application is a divisional application of U.S. application Ser. No. 08/975,229 filed Nov. 21, 1997 which is incorporated herein by reference.

TECHNICAL FIELD

The present invention is for a combinatorial chemical library of compounds structurally related to the moenomycin class of antibiotics, and methods of preparing the compounds. Members of the library comprise disaccharides and trisaccharides covalently bonded to a lipid or lipid mimetic through a phosphorus linkage.

BACKGROUND OF THE INVENTION

The moenomycin antibiotics are naturally-occurring phosphoglycolipids, which have been isolated from several strains of Streptomyces. These antibiotics have a wide range of antimicrobial activity, which is believed due to their ability to inhibit the transglycosylase activities of the bi-functional penicillin binding proteins (PBPs). These proteins catalyze the transfer of a disaccharide unit to a growing peptidoglycan chain during the biosynthesis of bacterial cell walls. To date, the moenomycins are the only known inhibitors of this enzyme activity. The structure of the disaccharide substrate is shown hereinbelow:

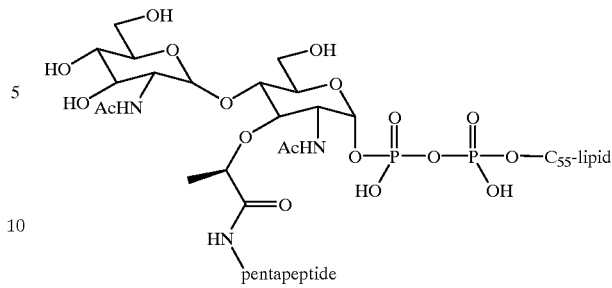

The moenomycins are active against several bacterial strains, including those resistant to beta-lactam antibiotics. They are currently marketed under the tradename Flavomycin® as an additive in cattle feed, where the efficacy in promoting animal growth is believed due to their antimicrobial activity. The moenomycins are particularly potent against gram-positive bacteria and less potent against gram-negative microbes.

The potential for moenomycin antibiotics as human therapeutics has not been studied in detail, but is expected to be limited by poor bioavailability and unfavorable pharmacodynamics. The unique mode of action and wide range of activity of this class of antibiotics makes them attractive for the study of related compounds having more favorable pharmacological properties.

At present, moenomycins A, $C_1$, $C_2$, $C_3$, $A_{12}$, and pholipomycin compose the class of moenomycin antibiotics. Of this class, the most studied member is moenomycin A—a pentasaccharide linked to a $C_{25}$ lipid group through a phosphate moiety. The structure of moenomycin A is shown hereinbelow. The structural similarity of this compound to the transglycosylase substrate mentioned above is readily apparent and suggests that moenomycin A acts as a competitive inhibitor of transglycosylase activity.

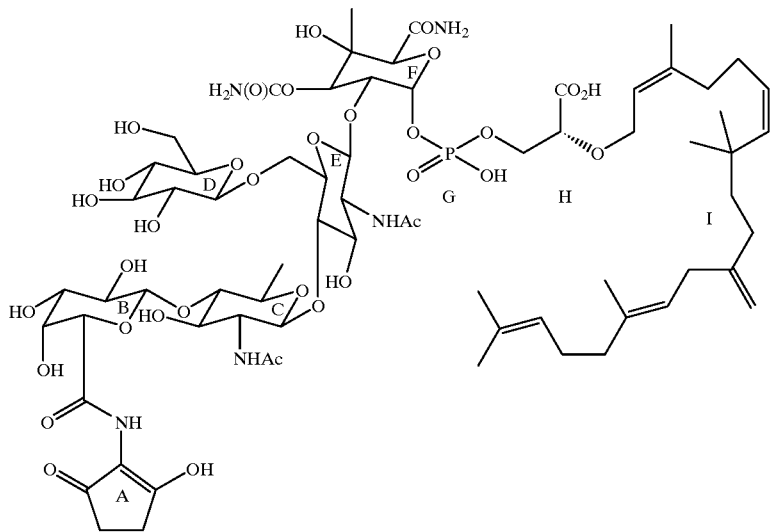

moenomycin A

In the above structure, it is known that a disaccharide-phospholipid degradation product of moenomycin A is equipotent (100% minimum inhibitory concentration (MIC) at 1 µg/mL) to the parent natural product [EP Publn. No. 130327]. In particular, it has been shown that the A, B, C and D units of moenomycin A are unimportant to the inhibition of transglycosylase activity, but that the E, F, G, H, and I groups are essential [Welzel, P., et al., (1984), (1987); Moller, U., et al., (1993); Marzian, S., et al., (1994)]. The lipid moiety I can be fully hydrogenated without substantially affecting its activity. However, a free carboxylic acid function for the glyceric acid unit H appears to be necessary for inhibition. Furthermore, the structural requirements within the F-G-H region appear to be rather strict [Fehlhaber, H-W., et al., (1990); Moller, U., et al., (1993); Luning, J., et al., (1994); Heuer, M., et al., (1994)]. The structure of a fully active disaccharide degradation product of moenomycin A is shown hereinbelow:

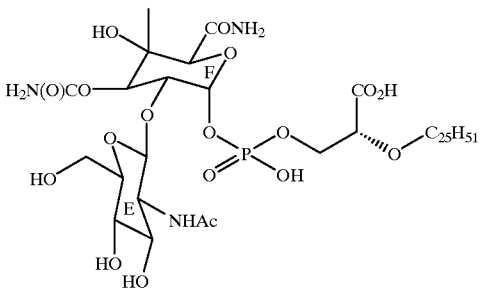

The other moenomycin compounds mentioned above differ structurally from moenomycin A principally by the number of sugar residues in the molecule and by the configuration of groups at the C4 position of the F sugar unit. In particular, only moenomycins A and $A_{12}$ have a D sugar residue attached to the E unit. Moenomycins $C_3$, $C_4$ and pholipomycin are tetrasaccharide-phospholipids, which differ from each other by the presence or absence of hydroxyl groups at the C6 positions of the C and E sugar units [Hessler-Klintz, M., et al., (1993); Scherkenbeck, J., et al., (1993)].

Moenomycin $C_1$ also is a tetrasaccharide and, as with moenomycin $A_{12}$, lacks the branching methyl group and has a change of configuration at the C4 position of the F sugar unit, i.e., the F unit is a galactopyranosiduronamide. In contrast to the other moenomycins, degradation studies of moenomycins $C_1$ and $A_{12}$ reveal that the smallest antibiotically active products for these F unit galactopyranosiduronamide compounds are trisaccharide derivatives, which include the C, E and F sugar units. It has been suggested that the additional saccharide unit (C) is required for these compounds in order to achieve the necessary hydrogen bonding environment within the active site, which is otherwise attained with a disaccharide unit in the 4-C-methyl glucopyranosiduronamide compounds [Hessler-Klintz, M., et al., (1993); Donnerstag, A., et al., (1995)]. In a recent series of papers, Welzel and coworkers describe the synthesis and antibiotic properties of some C-E-F trisaccharide derivatives of moenomycin $A_{12}$ [Ritzeler, O., et al., (1997a); Ritzeler, O., et al., (1997b); Range, G., et al., (1997)].

The biosynthesis of moenomycin in an aerobic fermentation process is the subject of U.S. Pat. No. 3,992,263, issued to Dietrich et al. Enzymatic methods for degrading moenomycin to defined end products, i.e., pentasaccharide and phospholipid products, are disclosed by U.S. Pat. Nos. 5,206,405, 5,260,206, and 5,506,140, all issued to Aretz et al., which propose that these end products can be used as building blocks in the synthesis of new transglycosylase inhibitors. An enzymatic method of cleaving the phosphate group from the aforementioned phospholipid is described in U.S. Pat. Nos. 5,315,038 and 5,316,929, issued to Aretz et al.

A study of the activities of several moenomycin analogs against the *Helicobacter pylori* bacillus is the subject of EP 655249, issued to Hoechst AG.

It is desired to synthesize and study a library of compounds having several of the basic structural features of the moenomycin degradation products discussed above, which retain anti-microbial activity. Of particular interest are compounds having better pharmacological properties yet retaining the broad spectrum of moenomycin activities. Of particular interest are activities against resistant strains of microorganisms. Generally speaking, it is desired to broaden the spectrum of activities and/or enhance the potencies of moenomycin antibiotics, particularly against clinically relevant microbes.

SUMMARY OF THE INVENTION

The present invention is for a combinatorial chemical library of moenomycin analogs, the members of which are represented by the following formula:

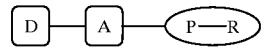

In the formula, "D" represents one or more "donor" saccharide residue(s), as defined hereinafter, and is preferably a mono- or disaccharide. The "A" group in the formula represents an "acceptor" saccharide residue, as defined hereinafter, and is a monosaccharide. The "P—R" group of the formula represents a lipophosphoglycerate mimetic group, as defined hereinafter, and differs from the phospholipid group of moenomycin A and partially or fully saturated forms thereof. Compounds represented by the above formula have a chemical structure analogous to the antibiotically active disaccharide moenomycin fragment discussed hereinabove. Accordingly, compounds represented by this formula are said to belong to a "directed" chemical library of moenomycin analogs.

In a preferred aspect of the invention, the C1 (anomeric) position of donor saccharide residue D is covalently bonded to the C2 position of acceptor saccharide residue A, e.g., through a glycosidic linkage. Also, it is preferred that the C1 (anomeric) position of A is covalently bonded to the lipophosphoglycerate mimetic group P—R through an O atom, which links A to a phosphorus atom of the P—R group.

Typically, the P—R group contains a phosphoester, phosphoanhydride, or phosphonate linkage, which joins an oxidized form of phosphorus to a negatively charged functional group, e.g., a carboxyl or sulfate group. While not wishing to be bound by any particular theory, it is believed that the dianion afforded by the P—R group is attracted to positive charges, e.g., a divalent metal ion, within the active site of the transglycosylase enzyme, thereby inhibiting its activity.

An aromatic or aliphatic moiety, sometimes referred to herein as a "lipid" moiety, can be covalently linked to the aforementioned oxidized form of phosphorus and the negatively charged functional group to provide the lipophosphoglycerate mimetic group. A synthetic or natural lipid moiety can form an integral part of the lipophosphoglycerate mimetic group by constituting part of the backbone joining the oxidized phosphorus to the negatively charged functional group. More typically, however, the lipid moiety is linked to the aforesaid groups through an ether, amide or carbon-carbon single bond.

Members of a library of the present invention display the greatest diversity of structural features in respect to: (i) substitutions occurring at the C3 position of residue A, (ii) substitutions occurring at the C2 position of the D saccharide, and (iii) the selection of the P—R group. Preferred substituents at the C3 position of A and the C2 position of D are amides, carbarnates, ureas, sulfonamides, substituted amines, esters, carbonates, and sulfates, as described herein. Preferred P—R groups are derived from homoserine, glyceric acid, salicylates, mandelic acid compounds, and phthalide phosphoric acids due to their ready availability.

Also contemplated is a method of preparing a library of compounds having the formula presented above. The synthesis can be performed in solution or on a support, and is preferably carried out on a solid phase support. A solid phase synthesis of the invention comprises the steps of:

(a) covalently linking an acceptor monosaccharide (A) to the support by forming a carboxylate or carboxamido linkage between the C6 carbon of A and the support, with A substituted at its anomeric carbon with a thiophenyl group;

(b) covalently linking the anomeric carbon of a donor saccharide (D) through an O-glycosidic linkage to the C2 carbon of the A residue to form a D—A moiety linked to the support;

(c) coupling a lipophosphoglycerate mimetic group (P—R) to the anomeric position of the A residue of the D—A moiety to form a D—A—P—R moiety linked to the support; and (d) cleaving the target D—A—P—R compound from the support.

The D—A coupling step (b) is preferably performed using a C1-thiophenyl donor saccharide that has been converted to its C1-sulfoxide form by a conventional method prior to reacting it with A. A preferred method of converting C1-thiophenyl sugars to their C1-sulfoxides is described in U.S. Ser. No. 08/281,167, the disclosure of which is incorporated herein by reference.

Before or after performing step (b), the C3 position of A and/or the C2 position of D can be functionalized. Preferred substituents at these sites are arnide, carbamate, urea, sulfonamide, substituted amine, ester, carbonate, and sulfate groups, as described more fully hereinafter. The hydroxyl groups of the A and/or D residues can be orthogonally protected to permit independent functionalization of their hydroxyl groups and it is generally preferred that protecting groups be cleaved from the assembled molecule prior to cleaving it from the support in step (d).

Preferably, coupling step (c) is performed by attaching a preformed P—R group to A. However, the P—R group can alternatively be assembled stepwise on A by first attaching a phosphorus-containing group, followed by an organic moiety that is negatively charged or that can be converted to have a negative charge, such that a lipophosphoglycerate mimetic (P—R) is linked to A.

A method of screening members of the present library for anti-microbial activity is also contemplated. Such method comprises contacting a member of the library with a culture of microbes, and monitoring the growth rate of the microbes. An observation that the growth rate has ceased or diminished is an indication that the compound has anti-microbial activity. Screening may also be performed by directly assaying for peptidoglycan synthesis in the microbes.

A fuller understanding of the present invention can be obtained from a consideration of the figures and detailed description provided hereinbelow.

DETAILED DESCRIPTION OF THE INVENTION

Figure 1:
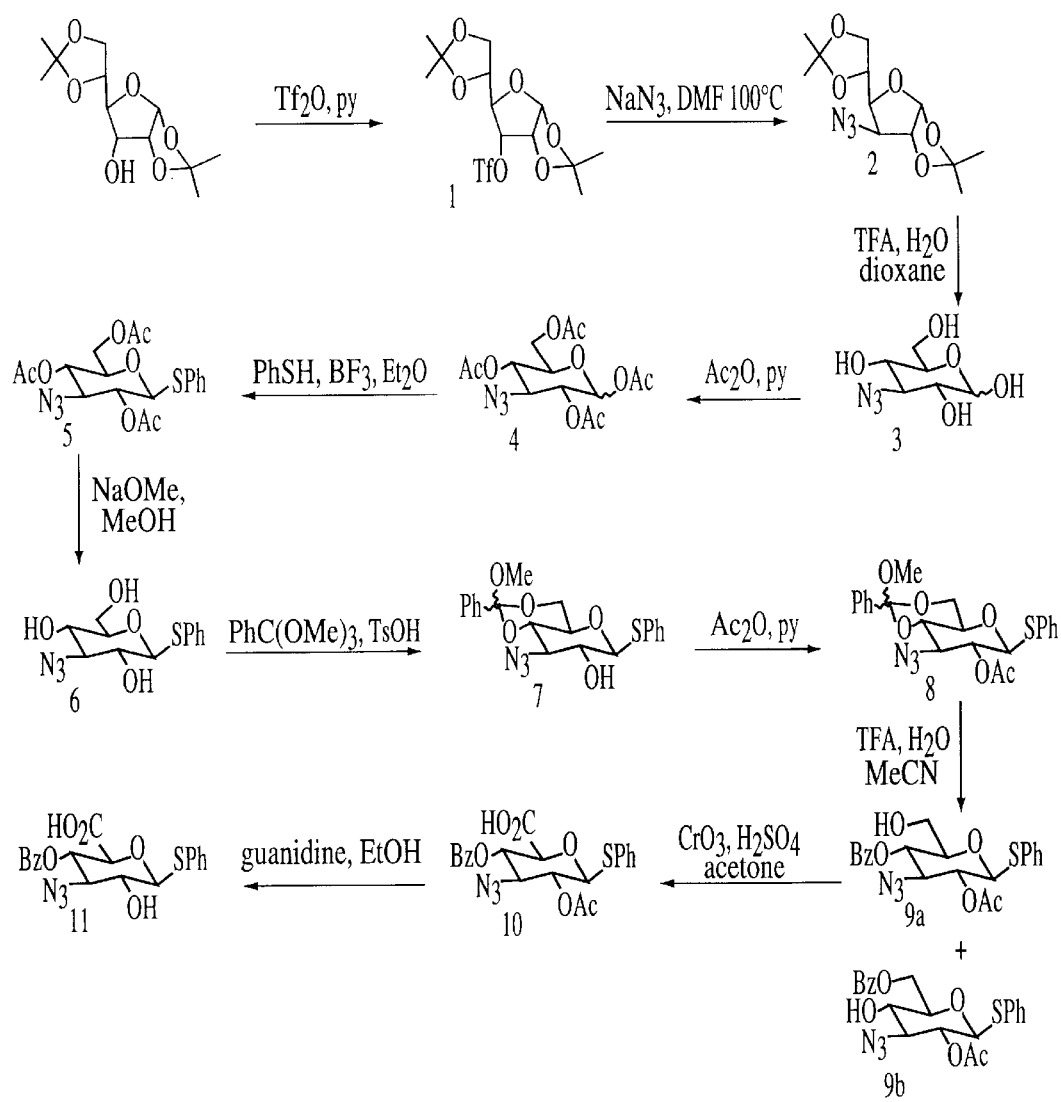
FIG. 1 depicts Scheme 1 for synthesizing acceptor saccharides of the invention according to Example I-1.
Figure 2:
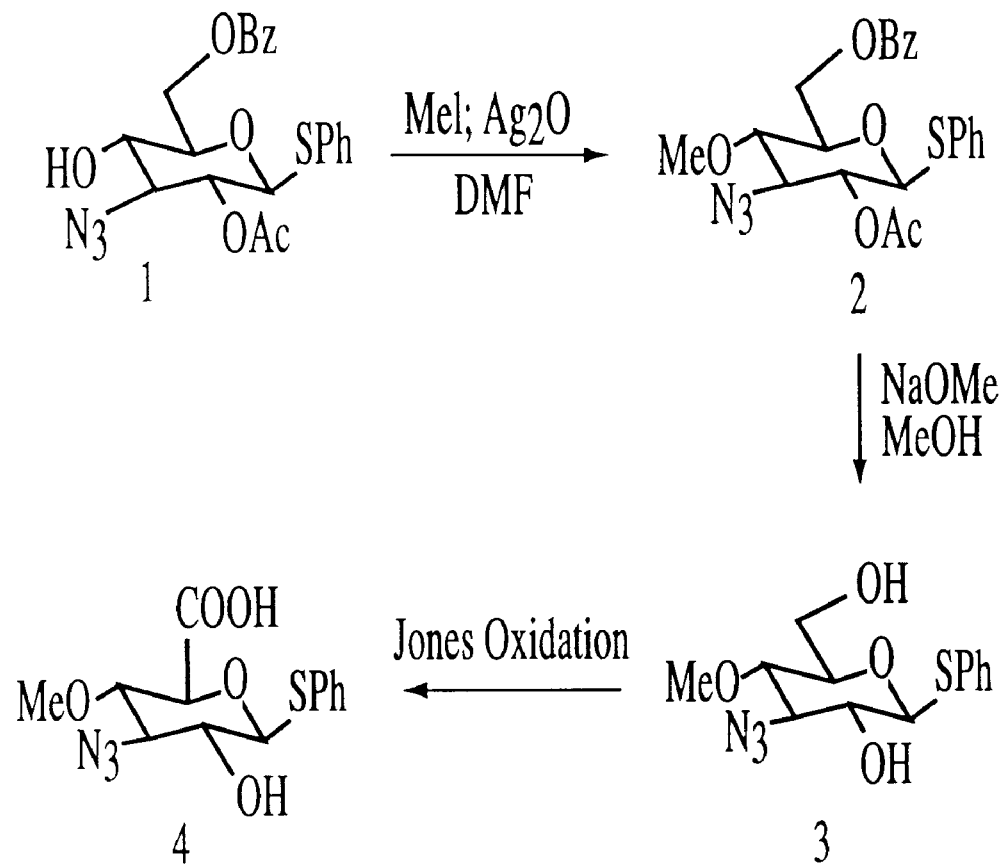
FIG. 2 depicts a reaction scheme for synthesizing an acceptor saccharide of the invention according to Scheme 2, which is discussed in Example I-2.
Figure 3:
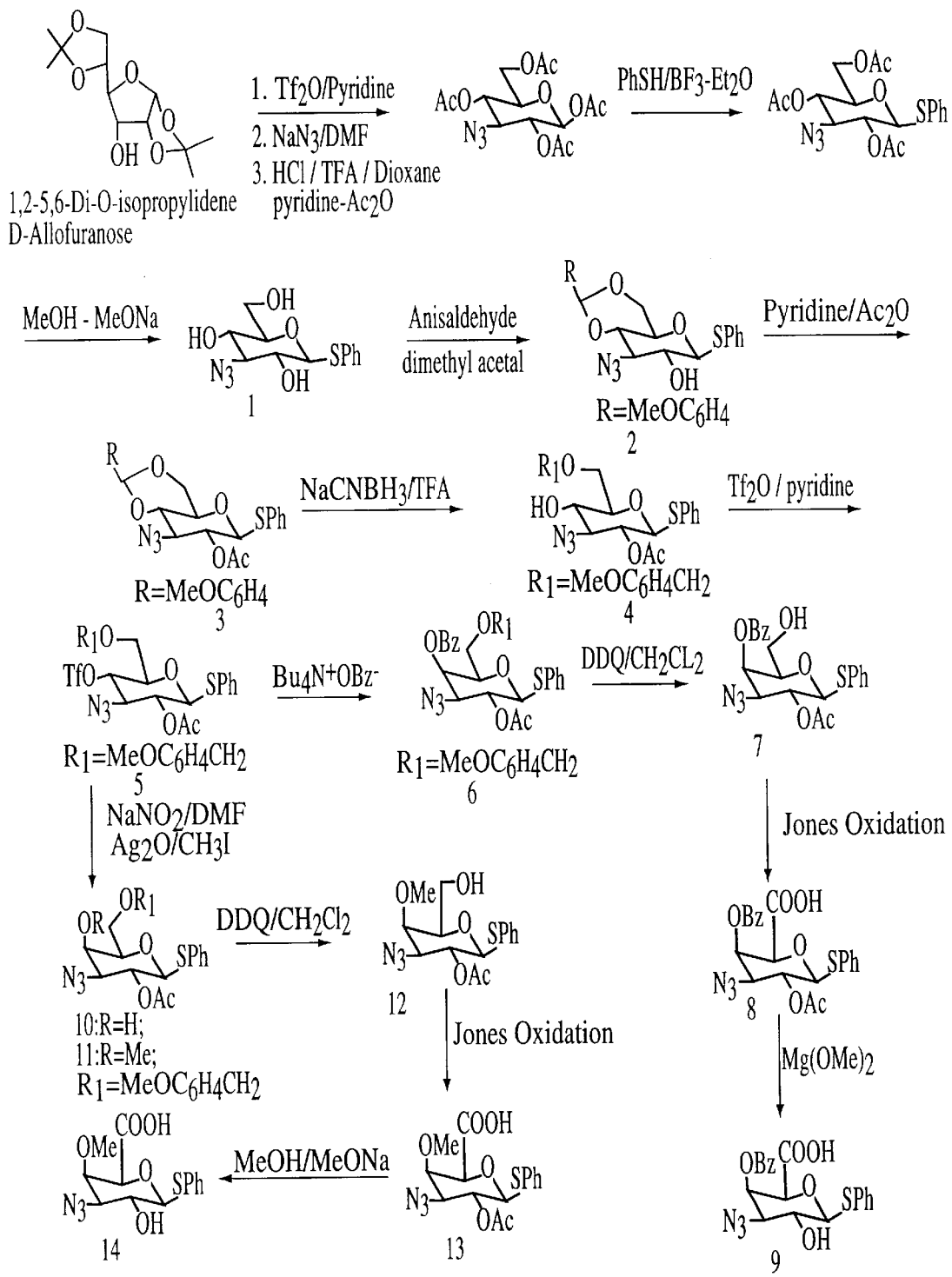
FIG. 3 depicts reaction schemes for synthesizing acceptor saccharides of the invention according to Scheme 3, which is discussed in Example I-3.
Figure 4:
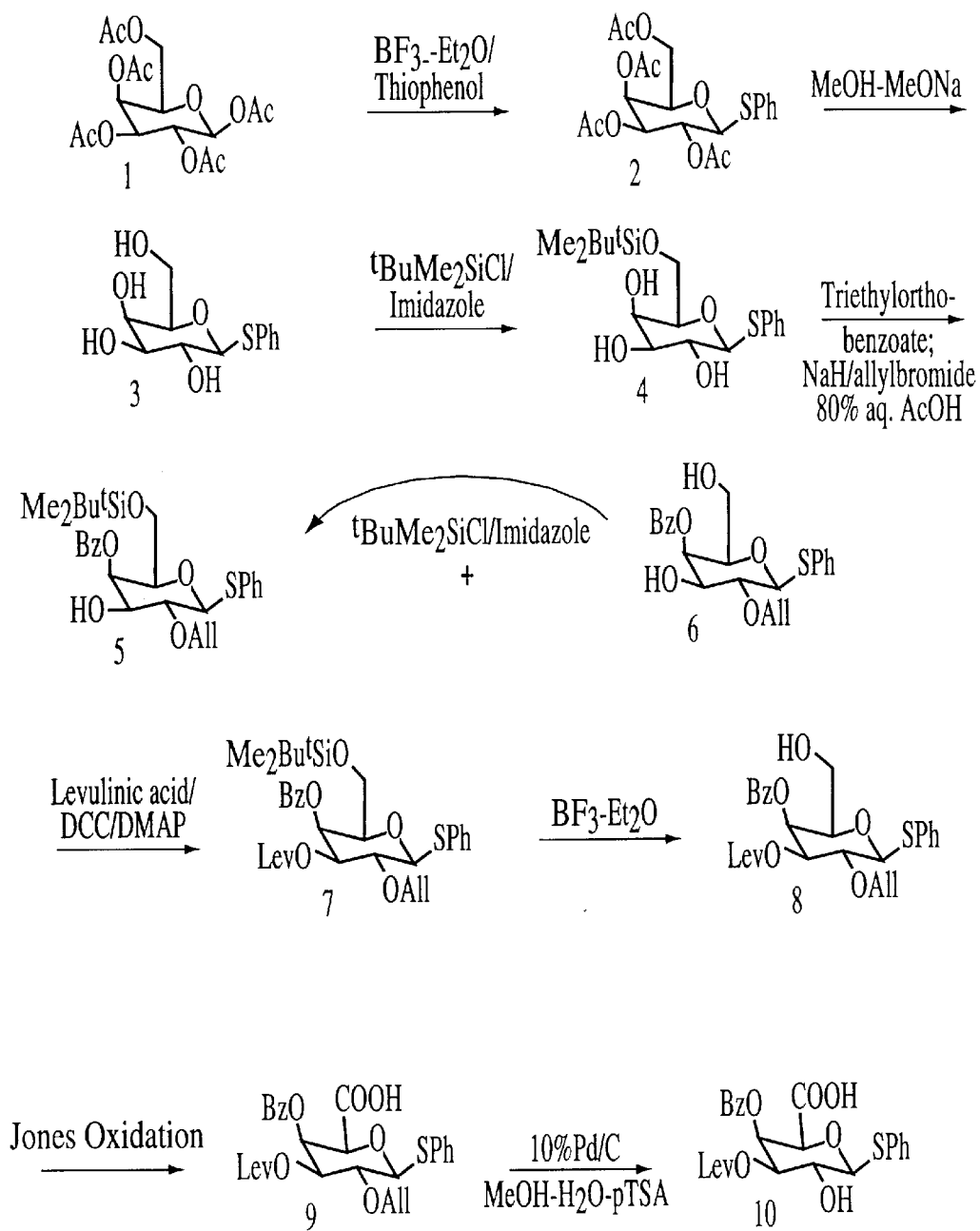
FIG. 4 depicts Scheme 4 for synthesizing an acceptor saccharide of the invention according to Example I-4.
Figure 5:
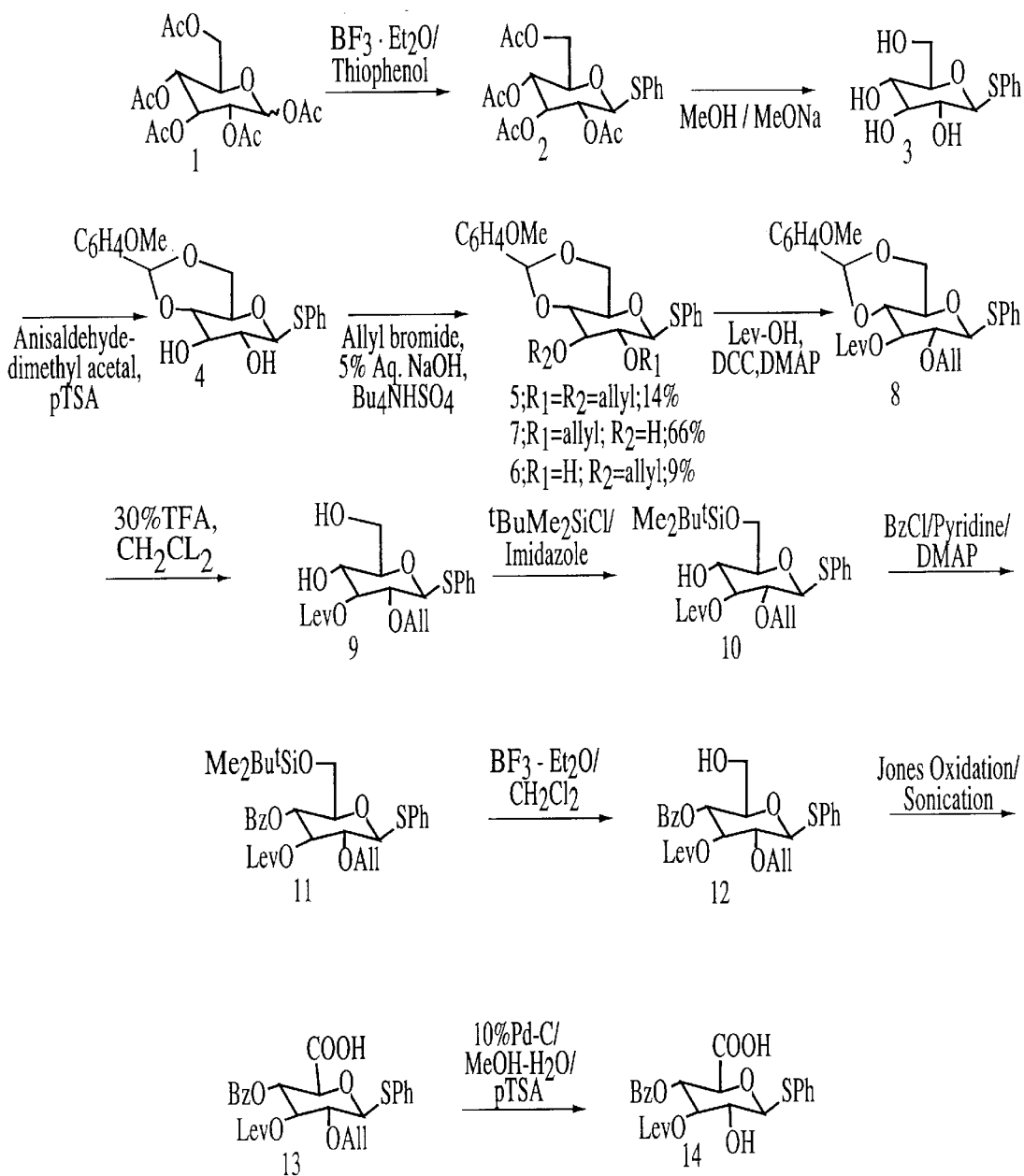
FIG. 5 depicts Scheme 5 for synthesizing an acceptor saccharide of the invention according to Example I-5.
Figure 6:
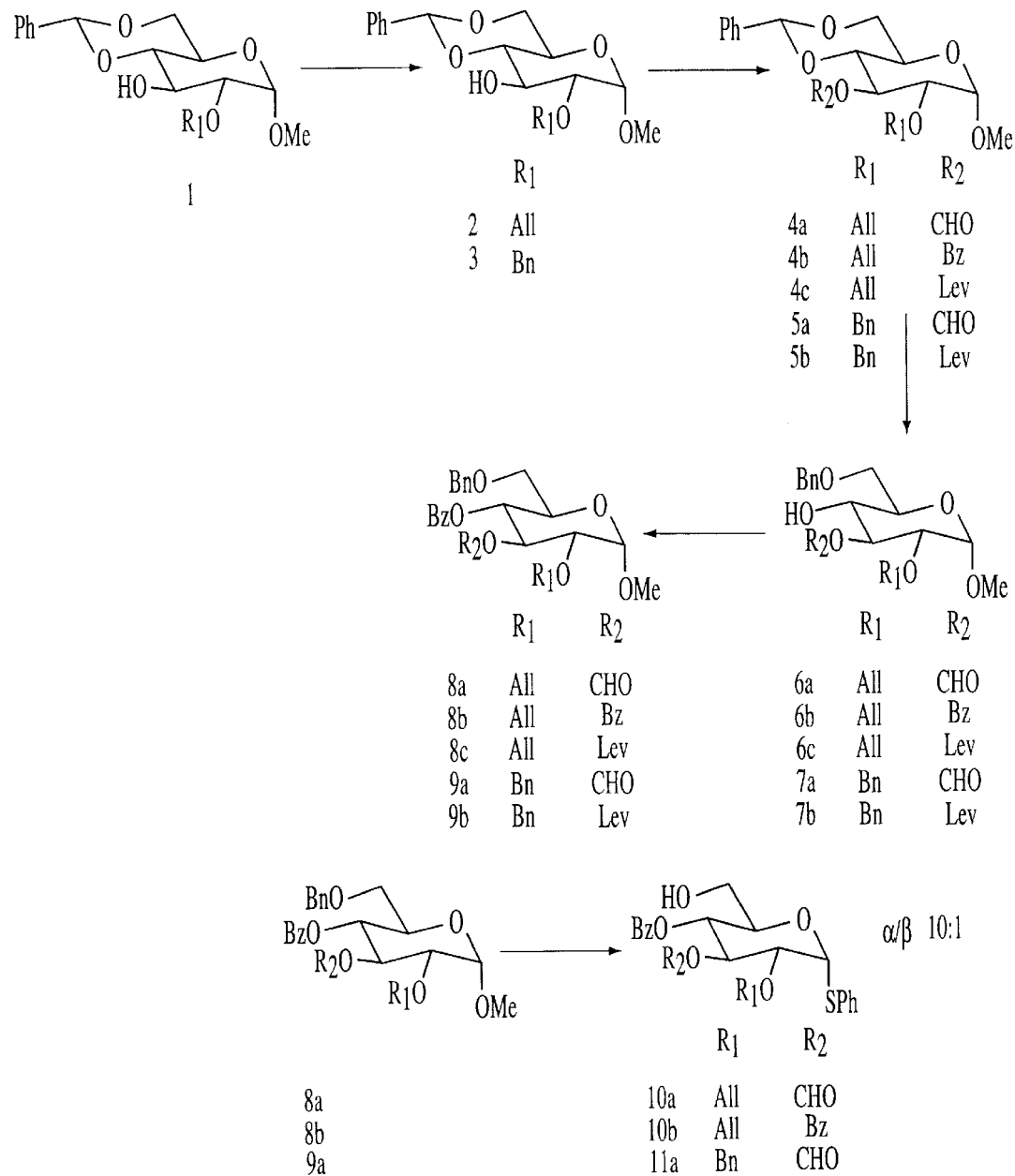
FIGS. 6–7 depict a reaction scheme for synthesizing acceptor saccharides of the invention according to Scheme 6, which is discussed in Example I-6.
Figure 7:
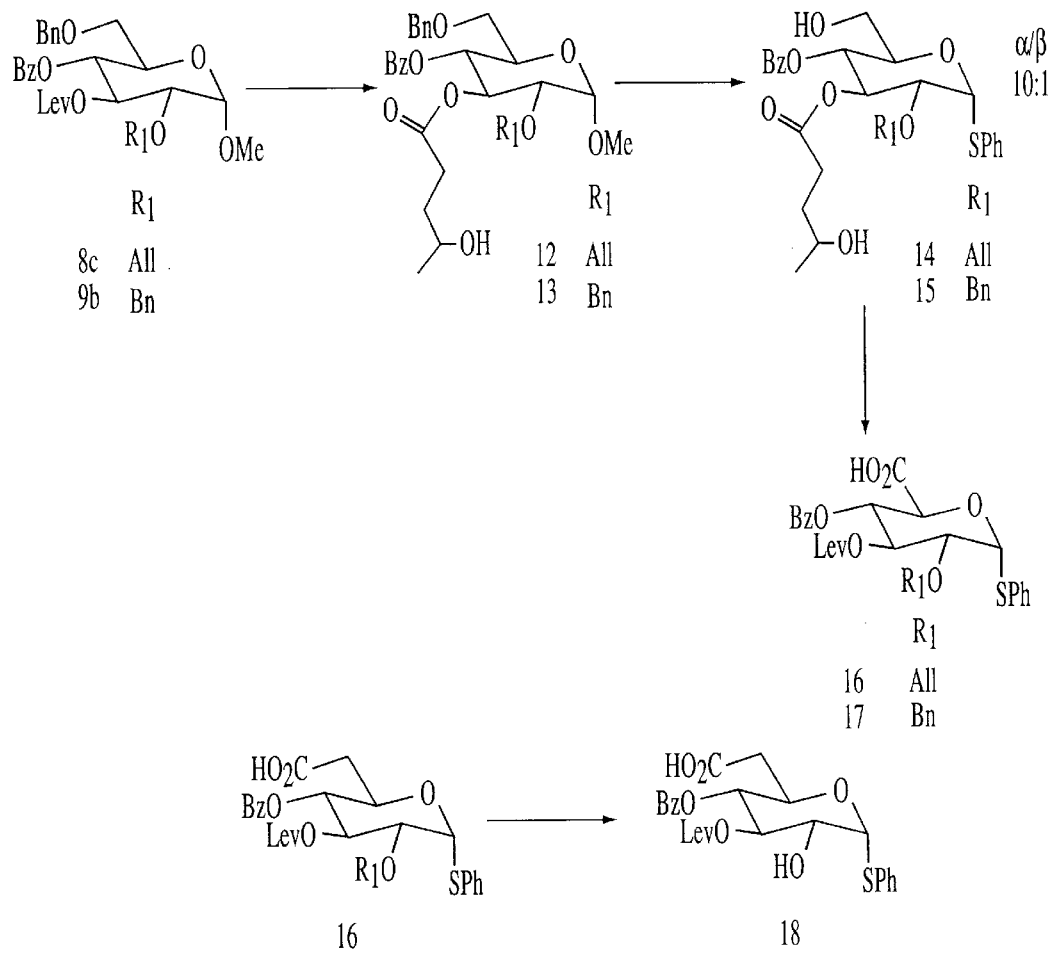
Figure 8:
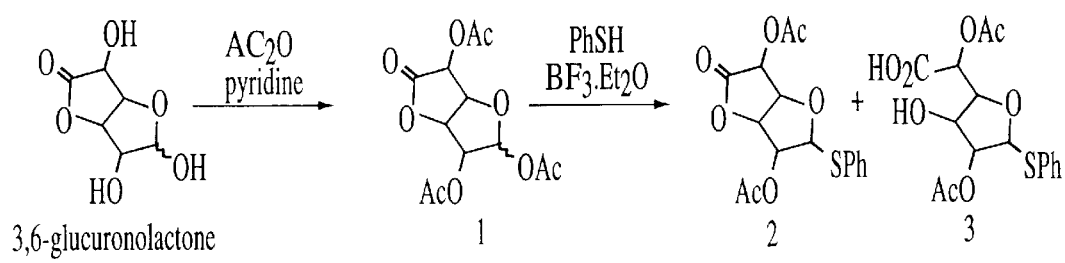
FIG. 8 depicts Scheme 7 for synthesizing an acceptor saccharide of the invention according to Example I-7.
Figure 9:
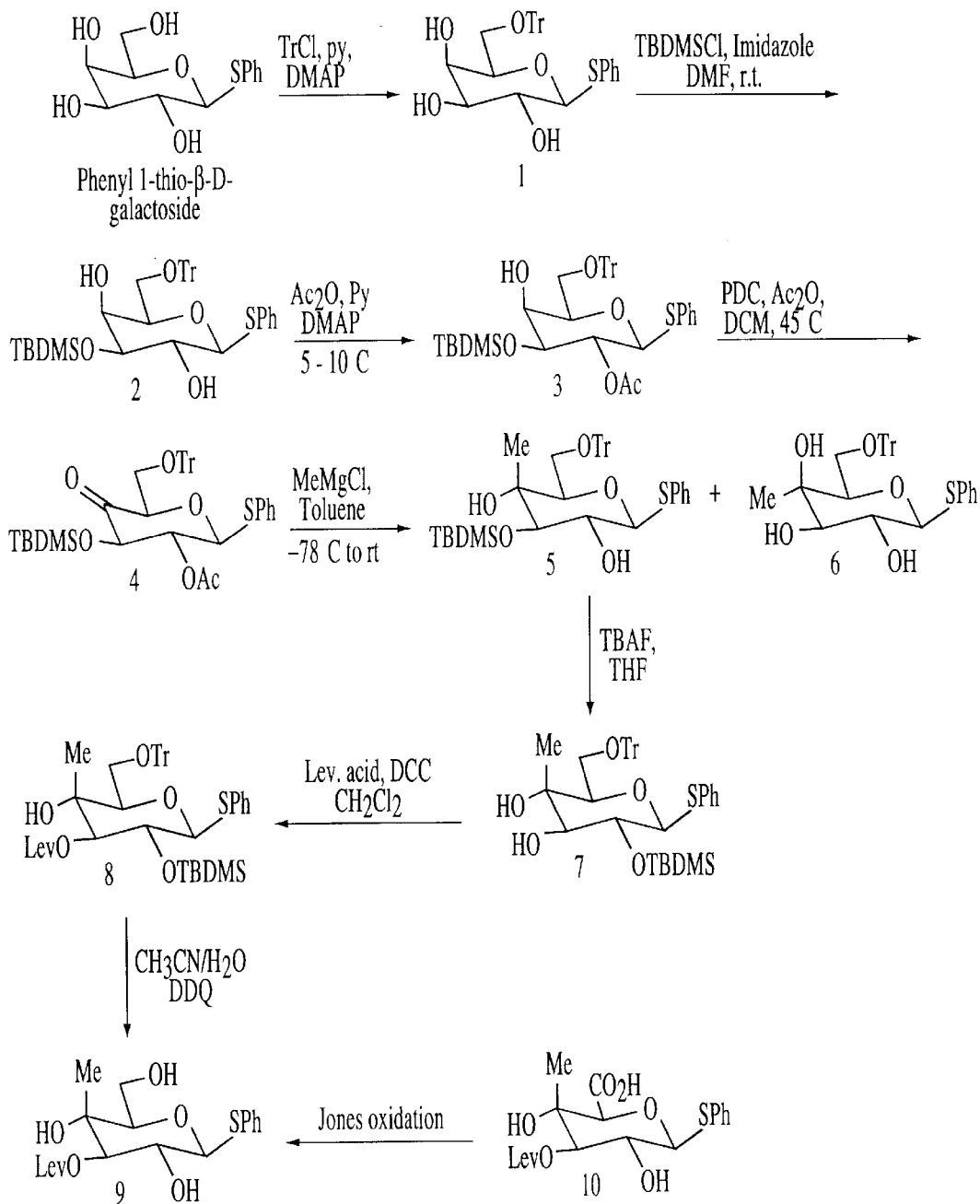
FIG. 9 depicts Scheme 8 for synthesizing an acceptor saccharide of the invention according to Example I-8.
Figure 10:
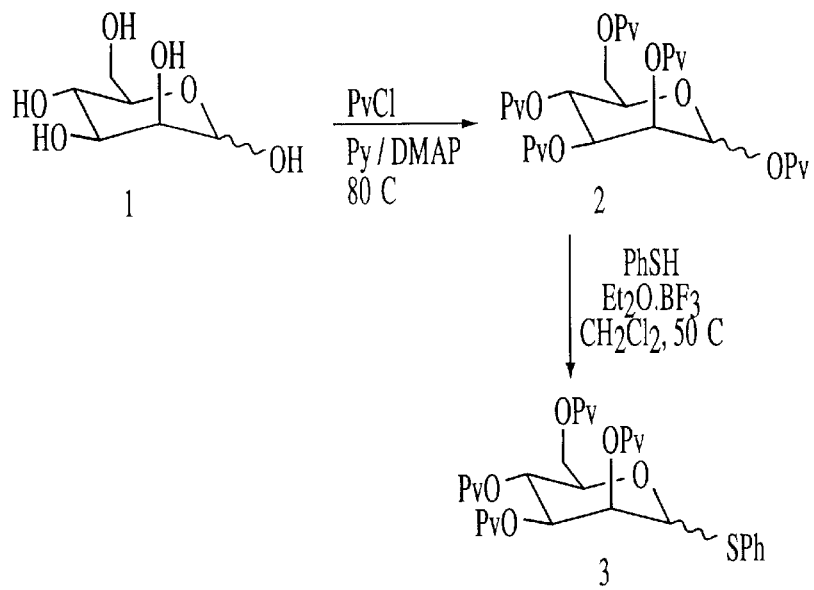
FIG. 10 depicts Schemes 9 and 10 for synthesizing donor saccharides of the invention, as discussed in Examples II-1 and II-2.
Figure 10:
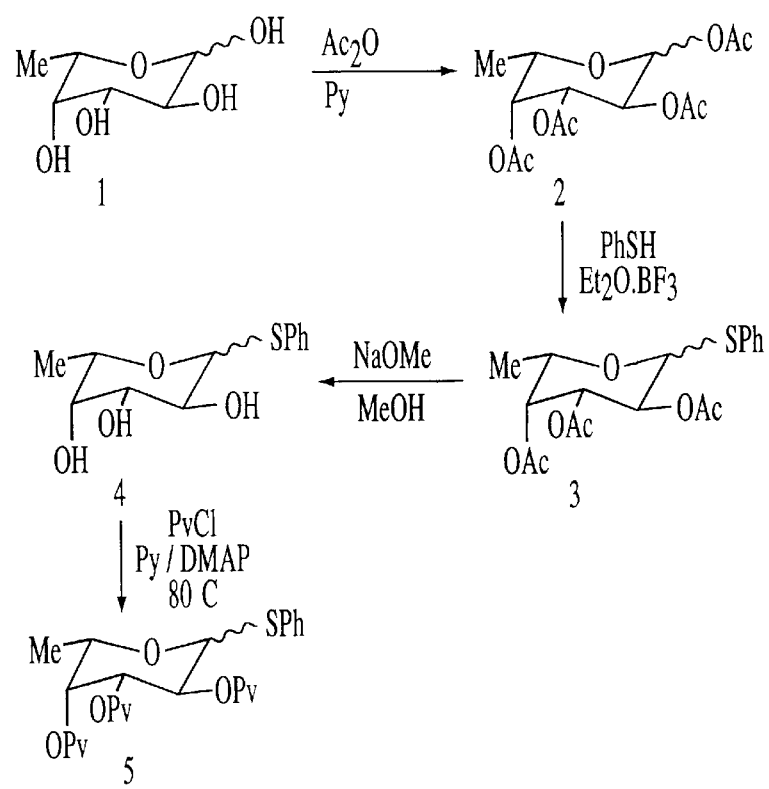
Figure 11:
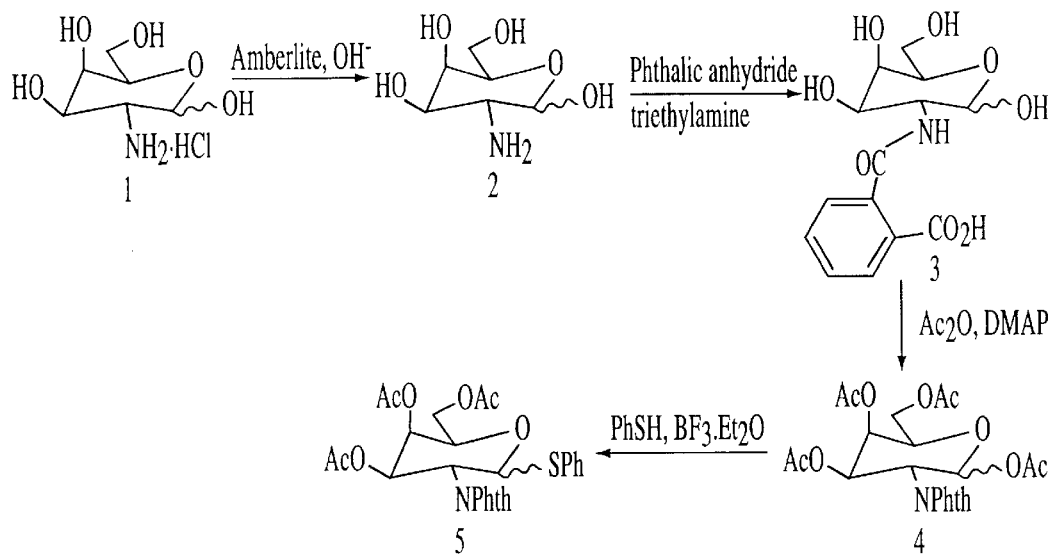
FIG. 11 depicts Schemes 11 and 12 for synthesizing donor saccharides of the invention, as discussed in Examples II-3 and II-4.
Figure 11:
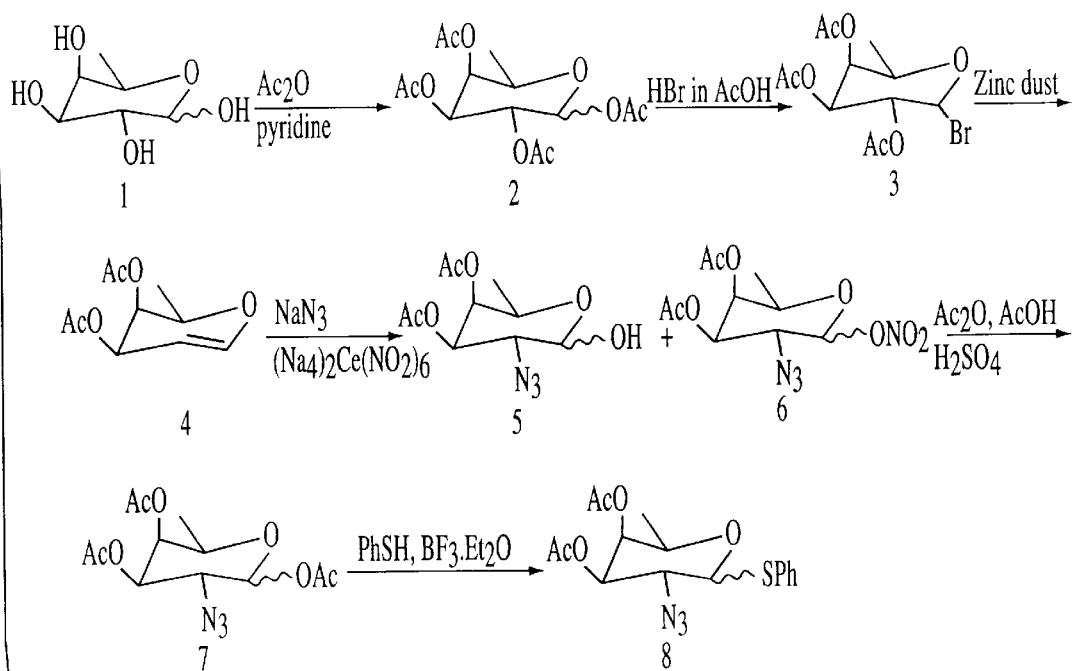
Figure 12:
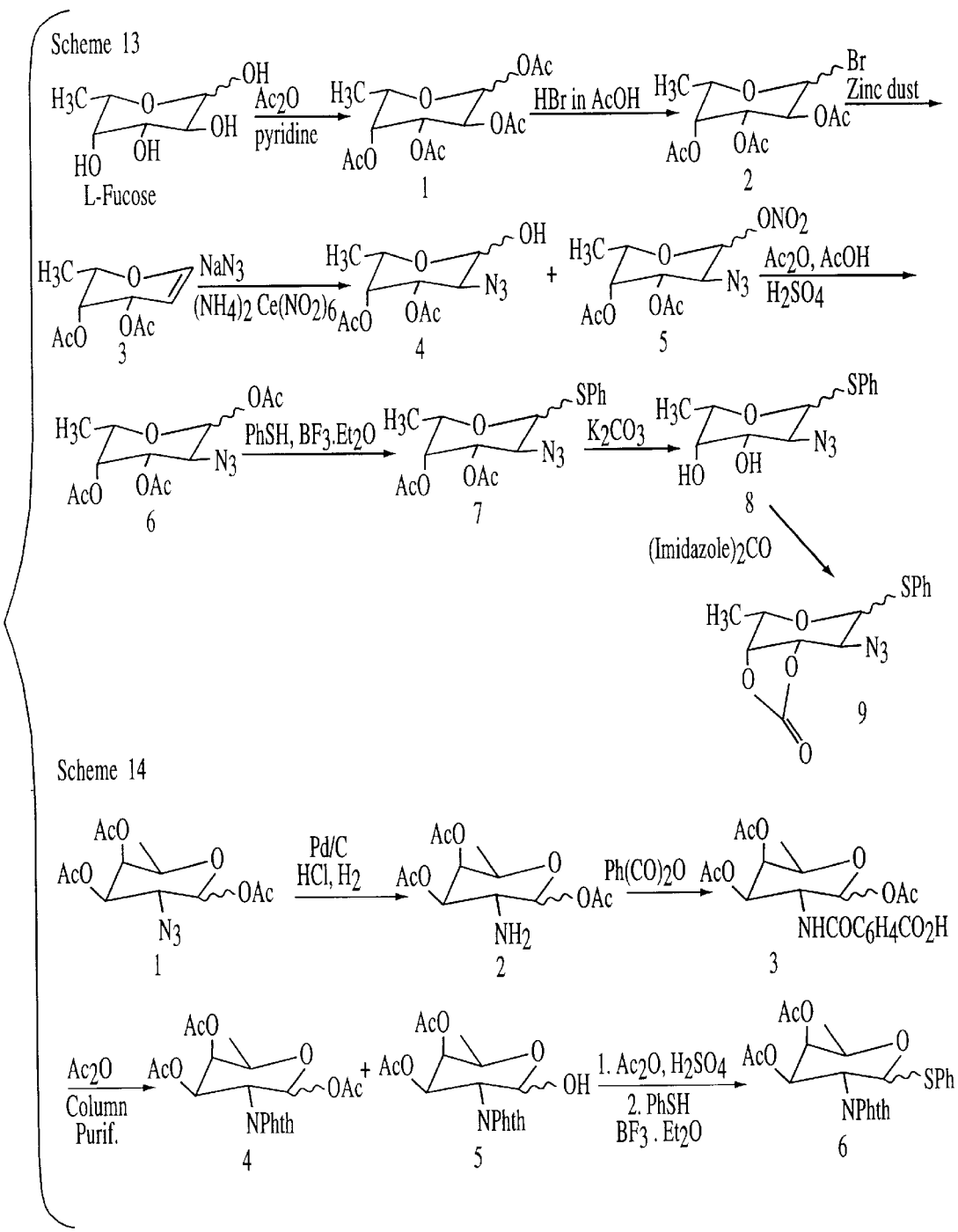
FIG. 12 depicts Schemes 13 and 14 for synthesizing donor saccharides of the invention, as discussed in Examples II-5 and II-6.
Figure 13:
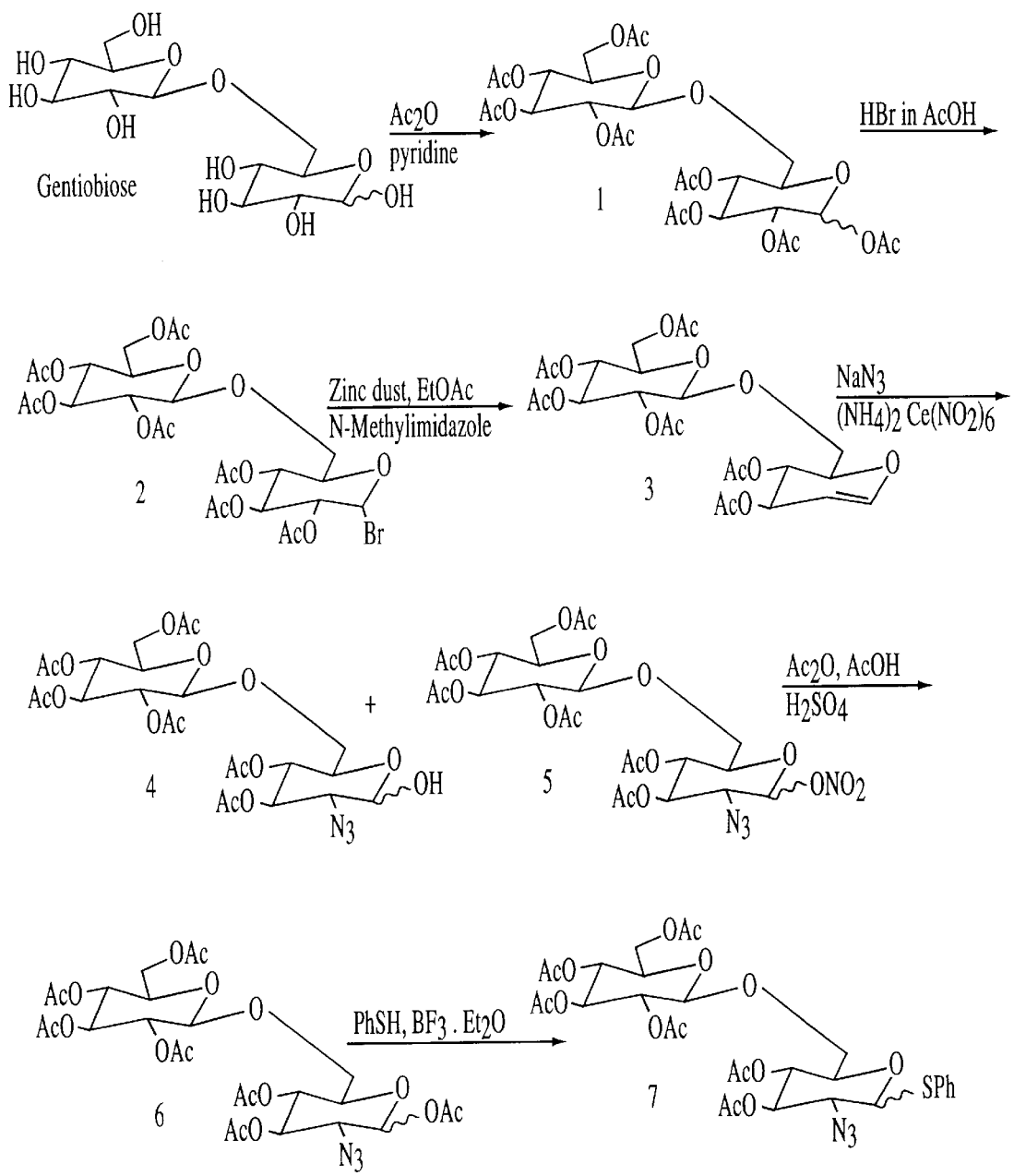
FIG. 13 depicts Scheme 15 for synthesizing a donor saccharide of the invention according to Example II-7.
Figure 14:
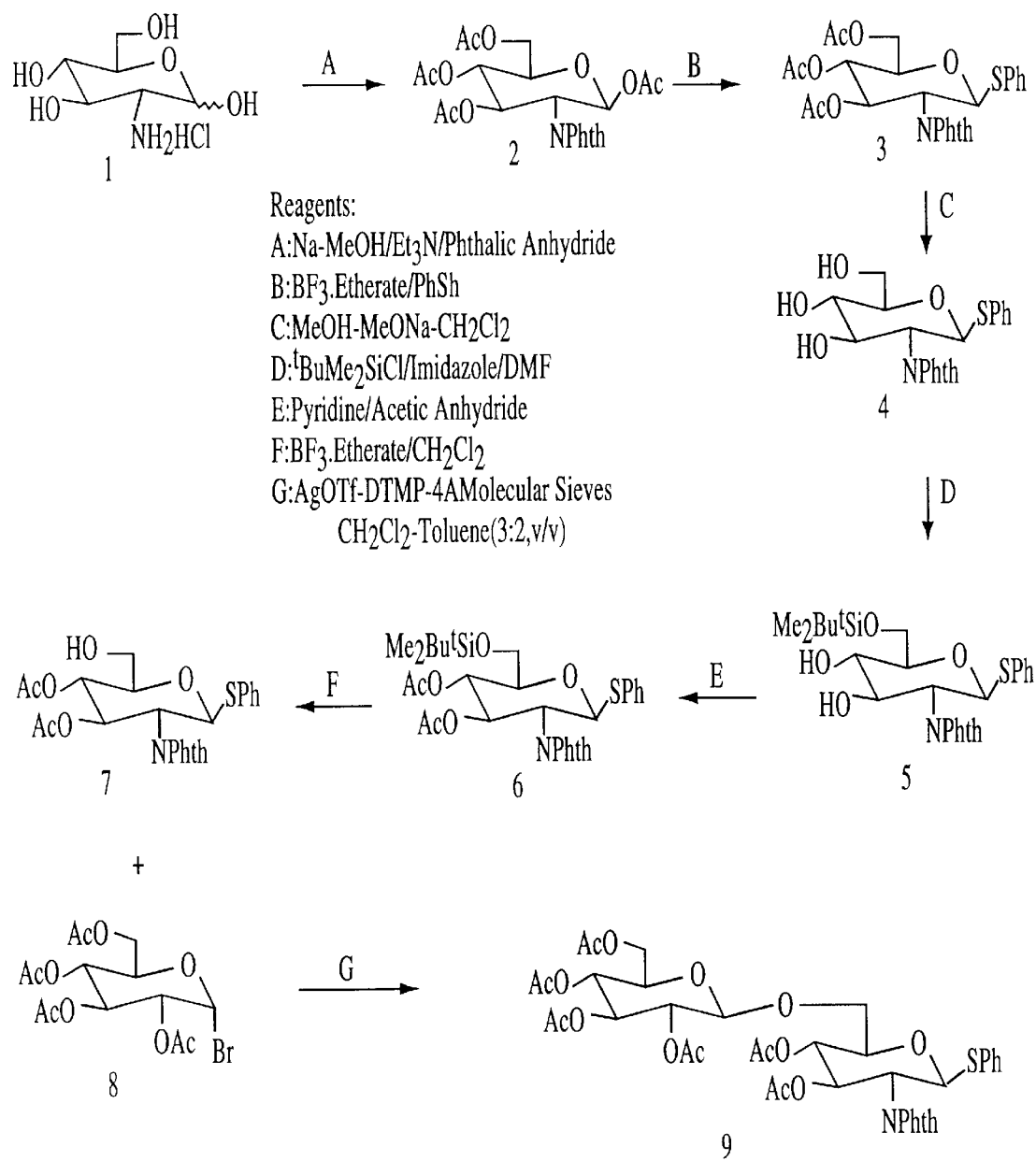
FIG. 14 depicts Scheme 16 for synthesizing a donor saccharide of the invention according to Example II-8.
Figure 15:
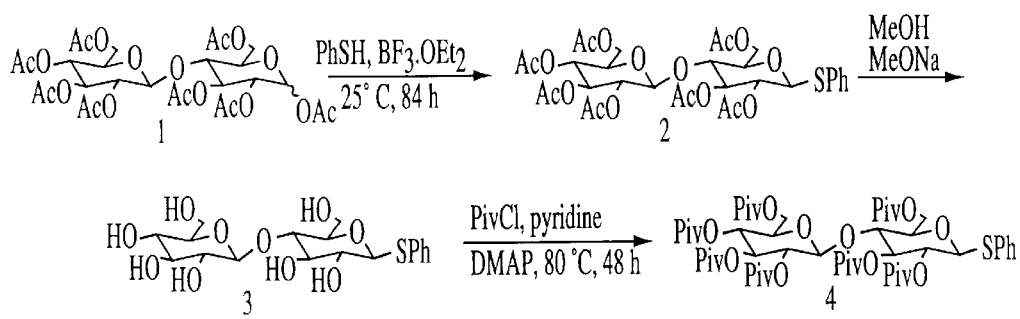
FIG. 15 depicts Schemes 17 and 18 for synthesizing donor saccharides of the invention, as discussed in Examples II-9 and II-10.
Figure 15:
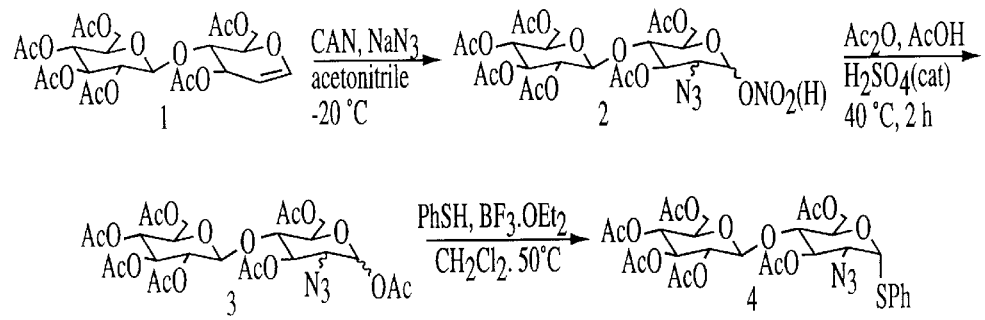
Figure 16:
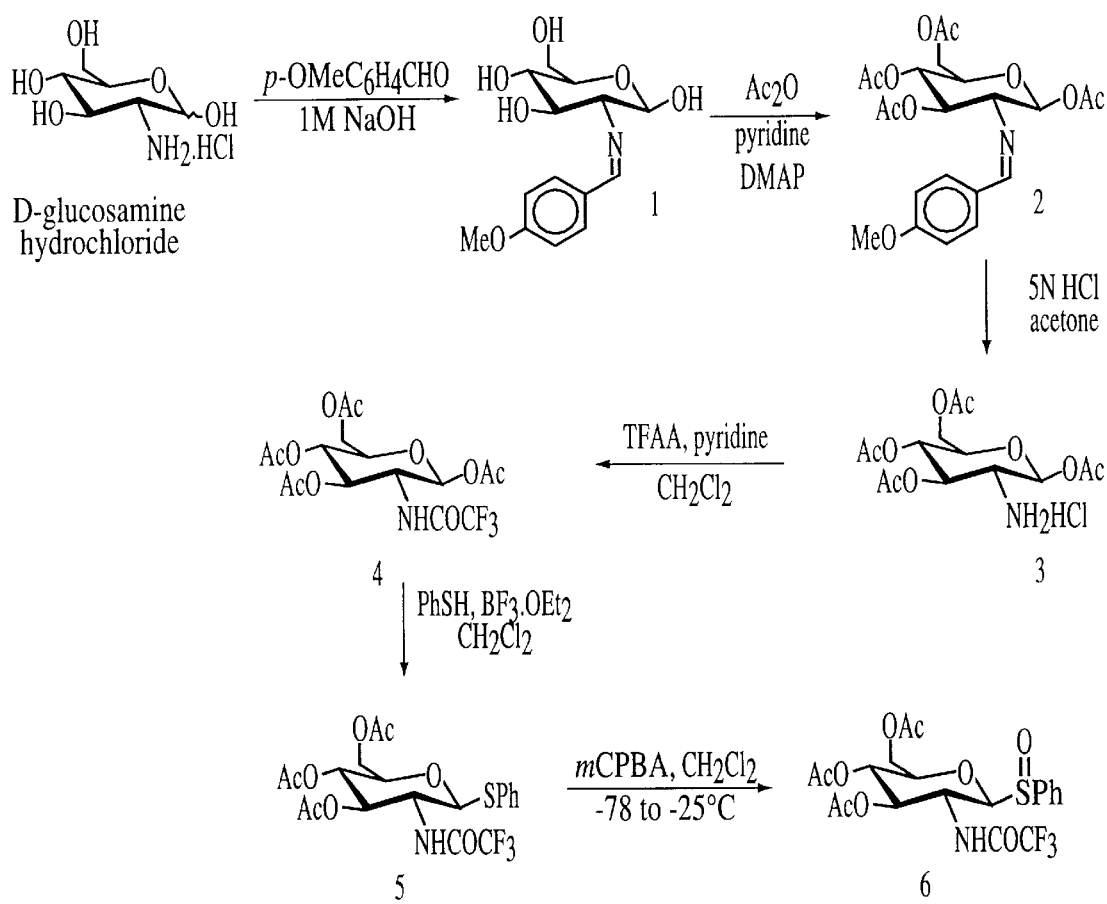
FIG. 16 depicts Scheme 19 for synthesizing a donor saccharide of the invention, including conversion to its sulfoxide form, according to Example II-11.
Figure 17:
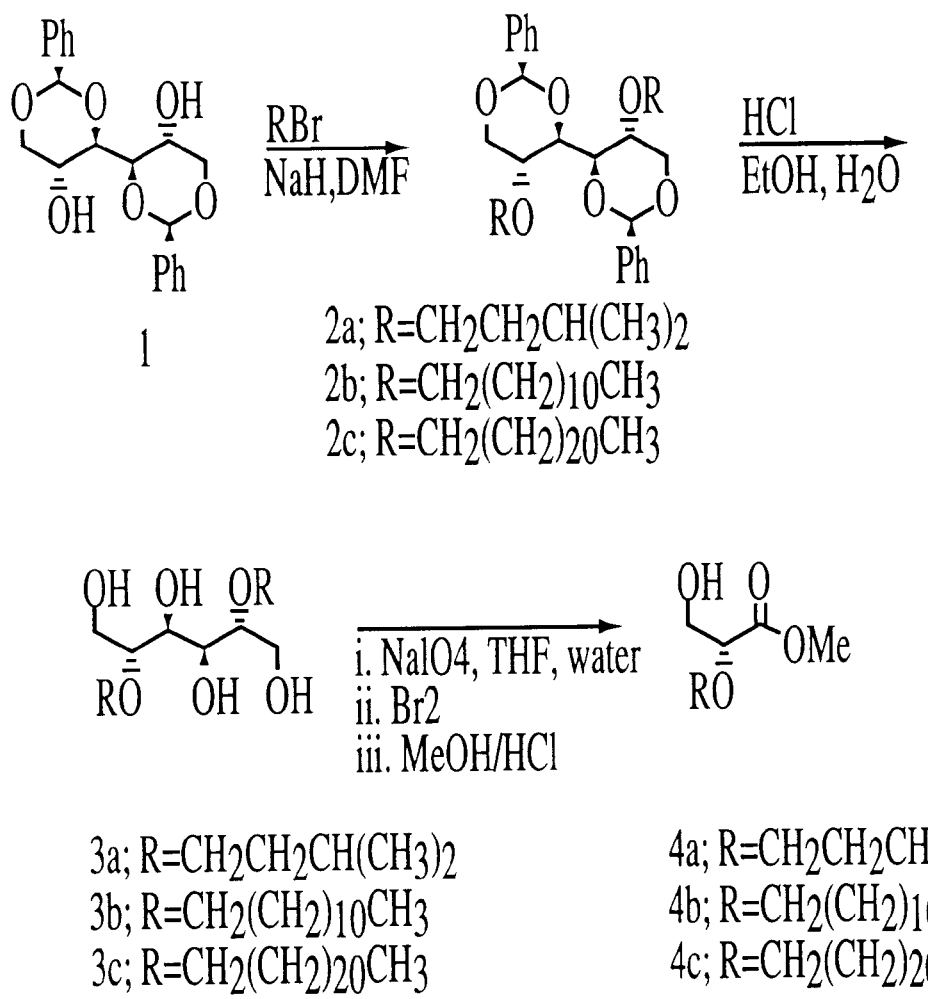
FIG. 17 depicts Scheme 20 for synthesizing lipid groups for incorporation into the lipophosphoglycerate mimetics used in preparing the moenomycin analogs of the present invention, as discussed in Examples III-1, III-2 and III-3.
Figure 18:
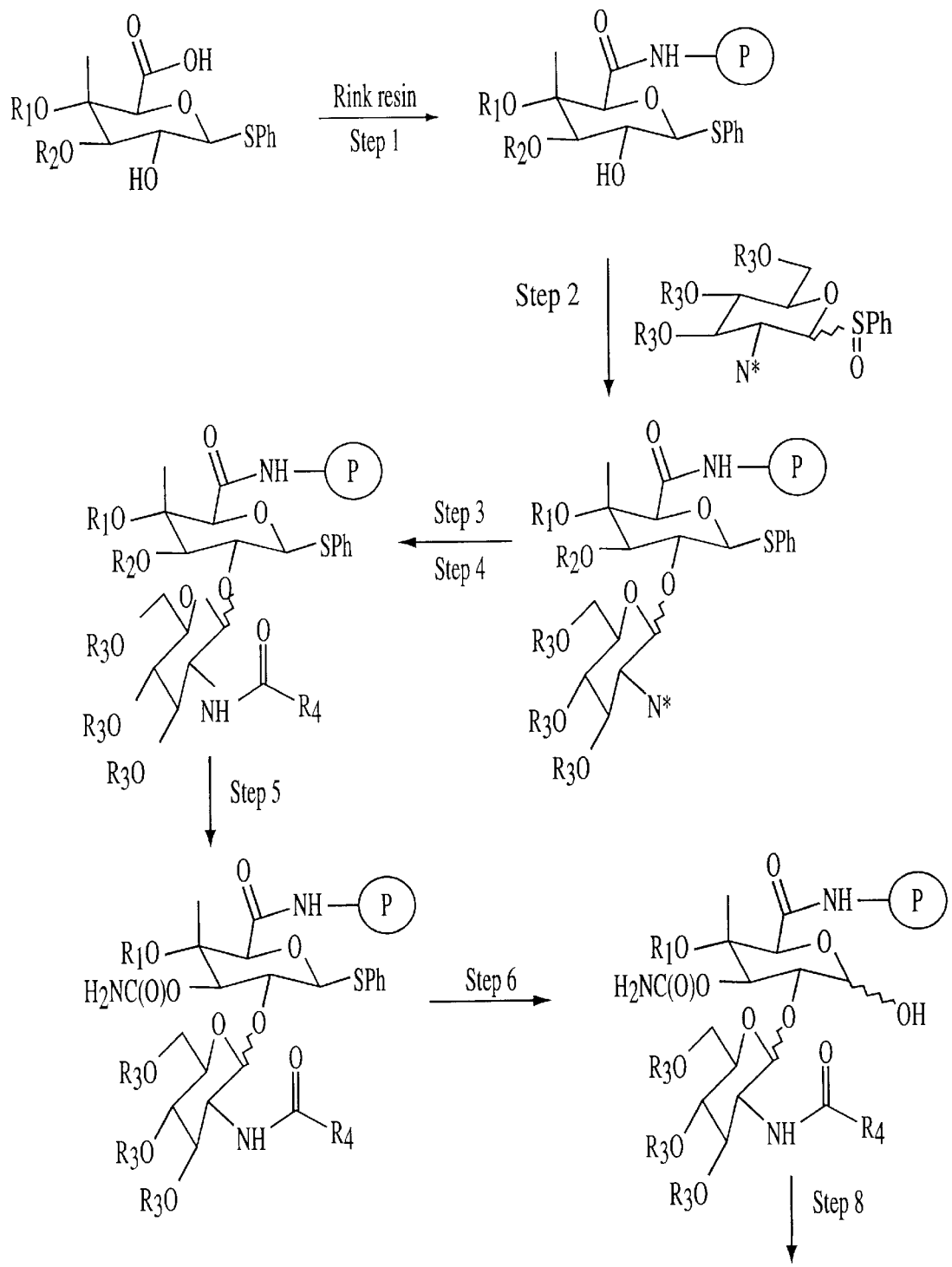
FIGS. 18–19 depict Scheme 21 for assembling moenomycin analogs on a solid support according to the principles of the present invention.
Figure 19:
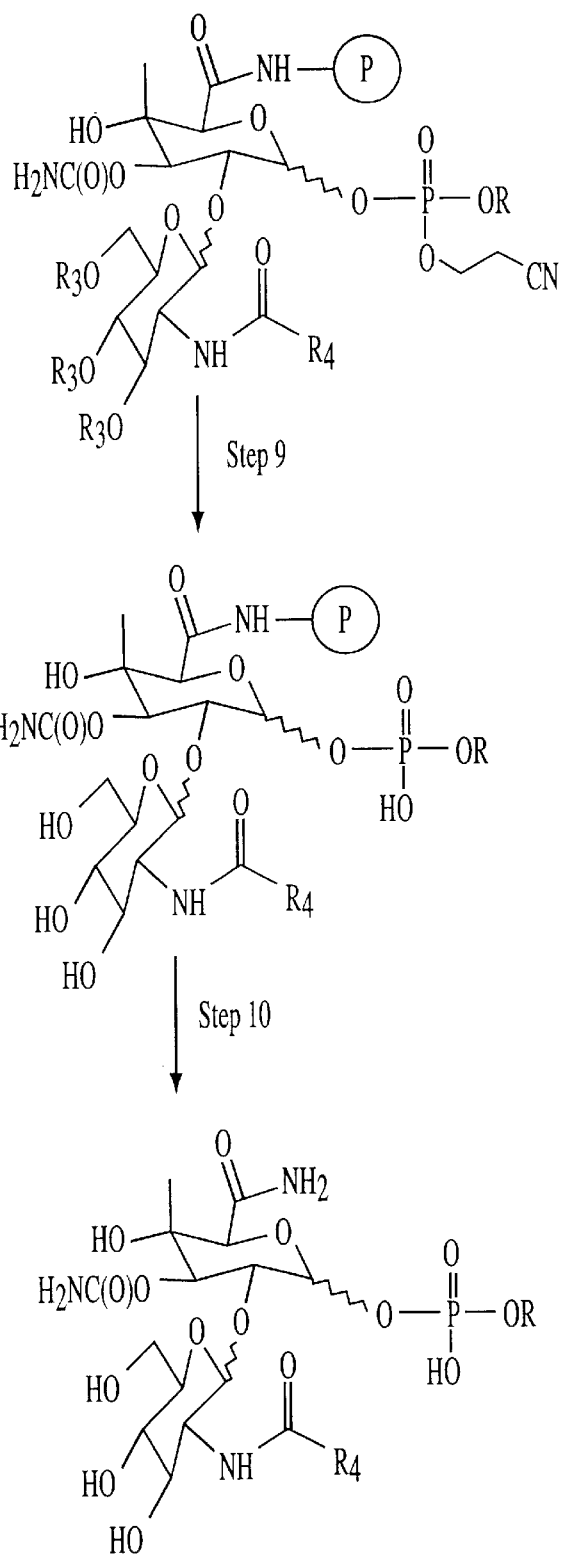

The present invention is described herein by way of certain specialized abbreviations and terms, the meanings of which are set forth as follows:

| List of Abbreviations | |
|---|---|
| All | allyl |
| Bn | benzyl |
| Bz | benzoyl |
| CAN | cerium ammonium nitrate |
| CEDIPAPCl | 2-cyanoethyl diisopropylamino phosphorus chloride |
| DCC | dicyclohexylcarbodiimide |
| DCM | dichloromethane |
| DDQ | 2,3-dichloro-5,6-dicyano-1,4-benzoquinone |
| DIPEA | N,N-diisopropyl ethylamine |
| DMAP | 4-N,N-dimethylamino pyridine |
| DMF | dimethylformamide |
| EA | ethyl acetate |
| ESMS | electrospray mass spectrometry |
| FAB | fast atom bombardment |
| HATU | O-(7-azabenzotriazol-1-yl)-1,1,3,3,-tetramethyluronium hexafluorophosphate |
| Lev | levulinoyl |
| mCPBA | m-chloroperbenzoic acid |
| Phth | phthalimido |
| PDC | pyridinium dichromate |
| Pv/Piv | pivaloyl |
| Py | pyridine |
| RT | room temperature |
| TBAF | tetrakis(n-butyl) ammonium fluoride |
| TBDMSCl | tert-butyl dimethylsilyl chloride |
| TEA | triethylamine |
| TFA | trifluoroacetic acid |
| TFAA | trifluoroacetic acid anhydride |
| Tf$_2$O | trifluoromethanesulfonic anhydride |
| TLC | thin layer chromatography |
| TrCl | trityl chloride |
| TsOH/pTSA | p-toluenesulfonic acid |

Glossary of Terms

Acceptor Saccharide—An acceptor saccharide (A), as used herein, "accepts" a donor saccharide to form a di- or trisaccharide residue of a moenomycin analog of the present invention. The acceptor saccharide is a natural or nonnatural hexose oxidized at its C6 position to either a carboxylate or carboxyamido group. In the final moenomycin analog compound, the acceptor residue is covalently linked at its C1 (anomeric) position with a lipophosphoglycerate mimetic group, and is covalently linked at its C2 position with a donor saccharide. The acceptor saccharide can be chemically modified (derivatized) at any of its normal hydroxyl sites (C1–C4 for pyranoses and C1–C3 and C5 for furanoses), with the preferred site for derivatization being the C3 position. Whenever the acceptor is a nonnatural hexose, it is typically an epimer of a naturally occurring monosaccharide. Additionally, C3 amino sugars are preferred acceptor saccharides.

Donor saccharide—A donor saccharide (D), as used herein, "donates" a mono- or di-saccharide group to an acceptor saccharide to form a di- or trisaccharide moenomycin analog of the present invention. The donor saccharide is formed from one or two natural or nonnatural hexoses. Whenever two hexoses are employed as the donor saccharide, they are covalently bonded together, e.g., through a (1→4) or (1→6) glycosyl linkage. The donor can be chemically modified (derivatized) at any of its normal hydroxyl sites (C1–C4 and C6 for pyranoses and C1–C3 and C5–C6 for furanoses). Typically, whenever a donor is derivatized, it is derivatized at the C2 position of the saccharide residue proximate the acceptor residue in the final molecule. Whenever the donor is a nonnatural hexose, it is typically an epimer of a naturally occurring monosaccharide.

Epimers—Sugar molecules differing in configuration at a single asymmetric center of the saccharide ring.

Lipophosphoglycerate mimetic—A chemical moiety having formula P—R that is covalently bonded to the C1 (anomeric) position of A through an O atom. The P—R group contains at least two electronegative functionalities separated by a predefined distance. These electronegative functionalities include independent selections from among phosphate, phosphoanhydride, phosphonate, sulfonate, carboxylate, hydroxyl, hydroxylamine, and acylsulfonamido groups. The electronegative functionalities can be an integral component of the backbone of the P—R structure or they can be attached as appendages to the backbone. Exemplary of these structures are integral (divalent) functionalities, such as phosphate and phenolate groups, and appendage (monovalent) functionalities, such as aliphatic hydroxyl and carboxylate. Two of the electronegative functionalities are spaced apart in the P—R group at a distance comparable to that of the phosphate and carboxylate groups (units G and H) of moenomycin A. This simulation of the electronic structure present in moenomycin A gives rise to the description herein of the P—R group as being a "mimetic" of the corresponding phosphoglycerate moiety of moenomycin A. Under biological conditions of interest, the aforementioned electronegative substituents typically release a proton, thereby leaving behind a negatively charged center. Preferably, a P—R group of the invention contains a phosphate group linked to another electronegative functionality. The phosphate group is bonded to an A residue through an O atom, and is linked to the second electronegative functionality, e.g., through a phosphoester, phosphoanhydride, or phosphonate linkage. The second electronegative functionality is preferably a carboxylic acid group. An aromatic or aliphatic moiety (also referred to herein as a "lipid") can be covalently linked to the aforementioned negatively charged functional group of the P—R group, e.g., through an ether, amide or single C—C bond, to provide the lipophosphoglycerate mimetic P—R. The aromatic or aliphatic moiety can form all or part of the backbone joining the negatively charged group to the oxidized phosphorus atom. Preferred P—R groups are discussed more fully hereinafter.

Position isomer—A structural isomer of another compound, particularly one having a cyclic or aromatic structure, which is formed by relocation of one or more substituent group(s) or by movement of one or more heteroatom(s) about the ring.

A combinatorial chemical library of the present invention is represented by the following formula:

In the formula, D represents a donor saccharide, A represents an acceptor saccharide, and P—R represents a lipophosphoglycerate mimetic group, as defined hereinabove. Preferably, the D residue is a mono- or disaccharide, which is covalently bonded to A through a glycosidic linkage. A is an oxidized monosaccharide, such as a pyranosiduronic acid, pyranosiduronamide, furanosiduronic acid, or furanosiduronamide, and is covalently bonded through an O atom to the P—R group. Preferably, the C1 position of D is linked to the C2 position of A and the C1 position of A is covalently bonded to P—R. The P—R group is not a phospholipid group of moenomycin A or a saturated form thereof.

In a preferred aspect of the invention, residue A of a member of the library is an α or β isomer of a D or L form of a glucopyranosiduronamide, a galactosiduronamide, a 4-C-methyl-galactopyranosiduronamide, a 4-C-methyl-glucopyranosiduronamide, a 3-amino-3-deoxy-analog thereof, or an epimer thereof More preferably, an A residue of a member of an instant library has a formula selected from among the following structures:

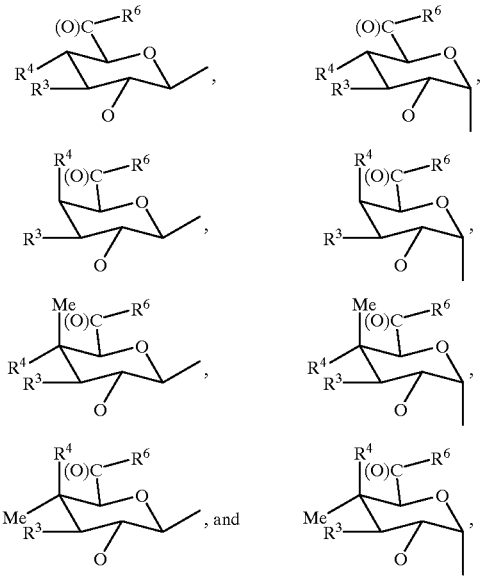

wherein

R³ is X—Y, where X is O— or NH—, and Y is H, alkyl, cycloalkyl, alkenyl, aryl, aralkyl, C(O)R, C(O)NHR, C(O)OR, or SO₂R, where R is H, alkyl, cycloalkyl, alkenyl, aryl, alkaryl, or heterocycle, or X—Y combine to form N₃;

R⁴ is O—X, where X is H, alkyl, cycloalkyl, alkenyl, acyl, benzoyl, aryl or aralkyl; and R⁶ is OH, NH₂, or NHMe.

As used herein, the term "alkyl" refers to straight and branched chain hydrocarbons containing 1 to 30 carbon atoms, such as methyl, ethyl, propyl, isopropyl, butyl, t-butyl, isobutyl, pentyl, hexyl, isohexyl, heptyl, octyl, nonyl, decyl, undecyl, and dodecyl. The term "lower alkyl" refers to alkyl groups having 1 to 7 carbon atoms, various branched chain isomers thereof, and the like. The terms "alkyl" and "lower alkyl" also include such groups having one or more halo-substituents, such as F, Cl, Br, I, CF₃, an alkoxy substituent, an aryl substituent, an alkyl-aryl substituent, a haloaryl substituent, a cycloalkyl substituent, an alkylcycloalkyl substituent, a hydroxyl group, an alkylamino substituent, an alkanoylamino substituent, an arylcarbonylamino substituent, a nitro group, a cyano group, a thiol group, or an alkylthio substituent.

The term "cycloalkyl" is a cyclic alkyl group that includes saturated hydrocarbon groups containing 3 to 12 carbon atoms, typically 3 to 8 carbons, and includes cyclopropyl, cylcopentyl, cyclohexyl, cycloheptyl, and cyclodecyl. A cycloalkyl group can be substituted with one or more halogen, lower alkyl, lower alkoxy group, hydroxy, alkylamino group, alkanoylamino, arylcarbonylamino group, aminogroup, nitro group, cyano group, thiol group or alkylthio group.

As used herein, the term "alkylene" or "alkenyl" refers to mono-, di-, tri- or higher unsaturated straight and branched chain hydrocarbons containing 1 to 30 carbon atoms, such as ethenyl, propenyl, butylenyl, hexenyl, octenyl, decenyl, and dodecenyl. The term "lower alkenyl" refers to alkylene groups having 2 to 8 carbon atoms, various branched chain isomers thereof, and the like. The terms "alkenyl" and "lower alkenyl" also include such groups having one or more halo-substituents, such as F, Cl, Br, I, CF₃, an alkoxy substituent, an aryl substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro group, a cyano group, a thiol group, or an alkylthio substituent.

The term "acyl" or "alkanoyl", either alone or as a part of another group, as used herein refers to an alkylcarbonyl or alkenylcarbonyl group, with the alkyl and alkenyl groups being those defined above. A "lower acyl", "lower alkanoyl" or "lower alkenoyl", either alone or as a part of another group, refers to a lower alkylcarbonyl or lower alkenylcarbonyl group, with the lower alkyl and lower alkenyl groups being those defined above. A formyl group is considered herein to be a lower acyl group.

The term "aryl" as used herein refers to monocyclic or bicyclic aromatic groups from 6 to 10 carbons in a ring, such as phenyl, naphthyl, substituted phenyl or substituted napthyl, wherein the substituent may be one or more lower alkyl groups, halogen, lower alkoxy, hydroxy, phenyl, alkanoyloxy, benzoyloxy, haloalkyl halophenyl, allyl, cycloalkylalkyl, adamantylalkyl, alkylamino, alkynoylamino, arylcarbonylamino, amino, nitro, cyano, thiol, alkylthio. The aryl group can be substituted with 1, 2, or 3 of the above substituents. The aryl can also be substituted in the ring with 1, 2 or 3 heteroatoms, in which case the group is referred to as a "heteroaryl" or "heterocycle".

The term "benzoyl" as used herein refers to an arylcarbonyl group, wherein the aryl group is as defined above.

The term "aralkyl", "aryl-alkyl", or "alkaryl", as used herein refers to a lower alkyl group having an aryl substituent as defined above, such as benzyl.

The term "lower alkoxy", "alkoxy", "aralkylthio", refers to a lower alkyl, aralkyl, or aryl group linked to an oxygen atom.

The term "lower alkylthio", "alkylthio", "arylthio" or "aralkylthio", refers to a lower alkyl, alkyl, aryl, or aralkyl group linked to a sulfur atom.

The term "lower alkylamino", "alkylamino", "arylamino" or "aralkylamino", refers to a lower alkyl, alkyl, aryl or aralkyl group linked to an nitrogen atom.

A "halogen" or "halo" as used herein refers to a halogen atom or halogen-containing group, such as or CF₃, F, Cl, Br or I.

A "heteroatom" as used herein refers to O, N, or S.

In another preferred aspect of the invention, a D residue of a member of an instant chemical library is an α or β isomer of a D or L form of a glucopyranoside, a galactoside, a mannopyranoside, a fucopyranoside, or an epimer thereof. More preferably, the D residue has a formula selected from among the following structures:

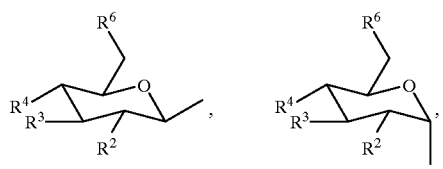

-continued

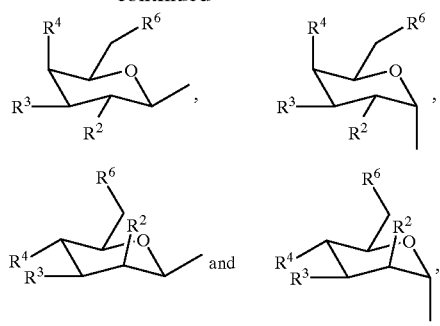

wherein

- $R^2$ is X—Y, where X is O— or NH—, and Y is H, alkyl, cycloalkyl, alkenyl, aryl, aralkyl, C(O)R, C(O)NHR, C(O)OR, or $SO_2R$, where R is H, alkyl, cycloalkyl, alkenyl, aryl, aralkyl, or heterocycle, or X—Y combine to form $N_3$, or phthalimido;
- $R^3$ is X—Y, where X is O— or NH—, and Y is H, alkyl, cycloalkyl, alkenyl, aryl, aralkyl, C(O)R, C(O)NHR, C(O)OR, or $SO_2R$, where R is H, alkyl, cycloalkyl, alkenyl, aryl, aralkyl, or heterocycle, or X—Y combine to form $N_3$, phthalimido, or a monosaccharide residue;
- $R^4$ is X—Y, where X is O— or NH—, and Y is H, alkyl, cycloalkyl, alkenyl, aryl, aralkyl, C(O)R, C(O)NHR, C(O)OR, or $SO_2R$, where R is H, alkyl, cycloalkyl, alkenyl, aryl, aralkyl, or heterocycle, or X—Y combine to form $N_3$, phthalimido, or a monosaccharide residue, or $R^3$ and $R^4$ combine to form carbonato; and
- $R^6$ is H or X—Y, where X is O— or NH—, and Y is H, alkyl, cycloalkyl, alkenyl, aryl, aralkyl, C(O)R, C(O)NHR, C(O)OR, or $SO_2R$, where R is H, alkyl, cycloalkyl, alkenyl, aryl, aralkyl, or heterocycle, or X—Y combine to form $N_3$, phthalimido, or a monosaccharide residue.

In a further preferred aspect of the invention, the P—R group of a member of an instant library contains at least two of the same or different electronegative functionalities. At least two of the electronegative functionalities are separated by a distance approximating that between the phosphate and carboxylate groups in moenomycin A, which is about 5.27 angstroms. Thus, a preferred lipophosphoglycerate mimetic (P—R) has a through-space charge separation in the range of 2.5 to 10 angstroms, more preferably 5–6 angstroms. An alternative formulation of this distance is expressed in terms of the number of contiguous chemical bonds separating the functionalities. Under this formulation, from 1 to 8 bonds separate the electronegative functionalities in the P—R group. By this convention, 3 chemical bonds separate the phosphate and carboxylate functionalities in moenomycin A.

Particularly preferred members of an instant library have a structural formula for A—P—R represented by one of the following formulas, or a position isomer thereof.

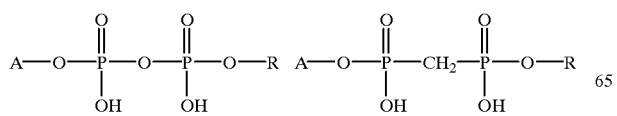

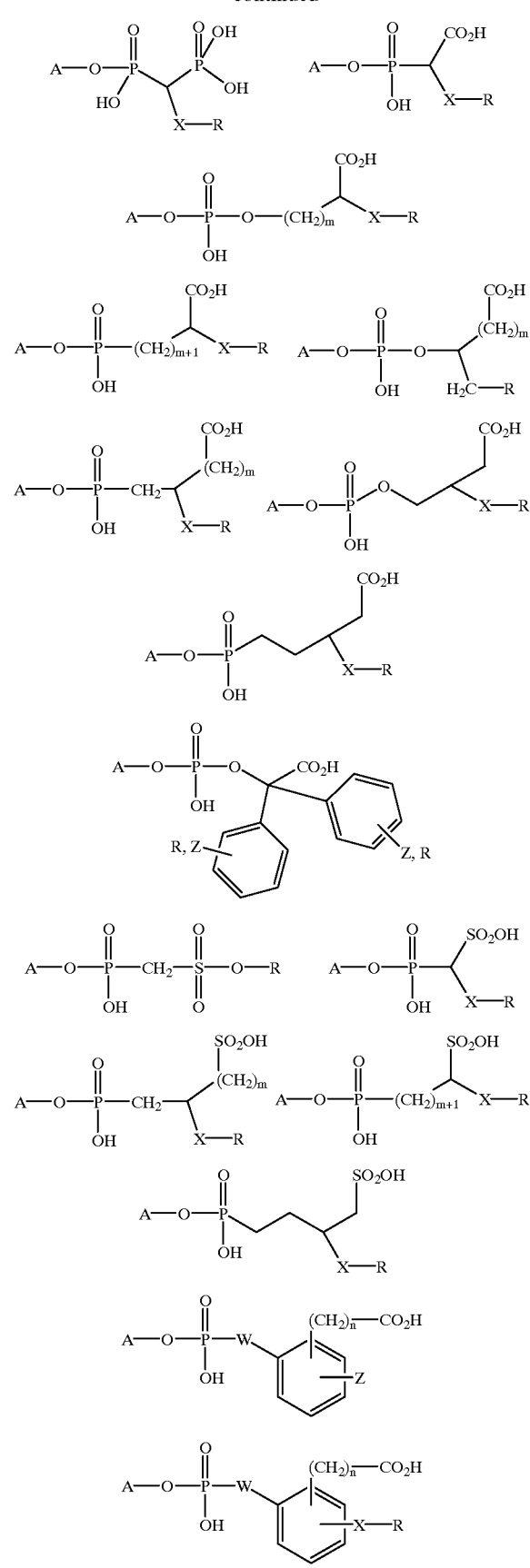

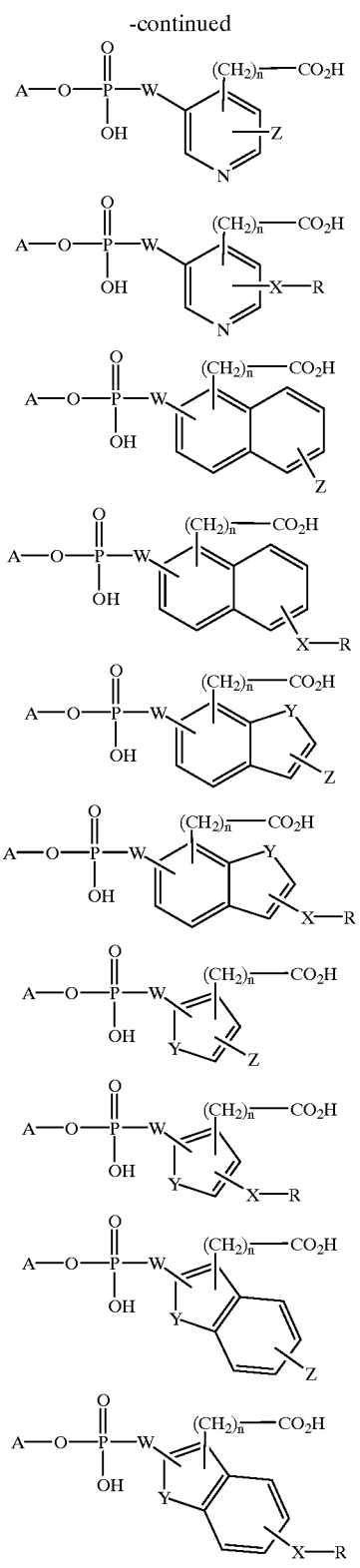

In the above formulas for a P—R group of the invention, the following designations have the indicated meanings:

W represents O, CH₂, O—CH₂—, or —CH₂—CH₂— and is a spacer between the negative charges presented by the oxidized phosphorus atom and the negatively charged functional group of the P—R moiety;

X represents a single bond, CH₂, O, NH, or S, and is an optional spacer between the backbone of the lipophosphoglycerate moiety and an R group, as defined hereinbelow;

Y is O, NH, S, or CH and is an atom (with the exception of CH) in an aromatic ring, which affords a "lipid" moiety of the P—R group;

Z is H, halogen, or NO₂, and represents a non-alkyl or non-aryl substituent on an aromatic ring, which affords a lipid moiety of the P—R group;

R is H, alkyl, cycloalkyl, alkenyl, acyl, aryl, benzoyl, aralkyl, or other such group substituted with one or more heteroatom. Preferred aliphatic R groups include (CH₂)₂CH(CH₃)₂, (CH₂)₁₁CH₃, and (CH₂)₂₁CH₃;

m is an integer of 0, 1, or 2 that indicates the number of methylene groups in the alkyl spacer group, which separates the oxidized phosphorus atom and the negatively charged functional group of the P—R unit; and n is an integer of 0, 1, or 2 that indicates the number of methylene groups separating the negatively charged functional group, e.g., COOH, from an aromatic ring in a P—R unit.

Exemplary of the above formulas are mandelic acid derivatives (in which m=0, X is absent, and R is aryl), phthalide phosphoric acids (in which W=CH₂, n=0, Z=H) and salicylic acid derivatives (in which W=O, m=0, and n=0), to name a few. These compounds are available from commercial sources or accessible by well-known methods.

Also contemplated within the invention is a phenyl 1-thio saccharide that can be used as an acceptor molecule for constructing moenomycin analogs of the present invention. Preferred acceptor molecules are among the following compounds:

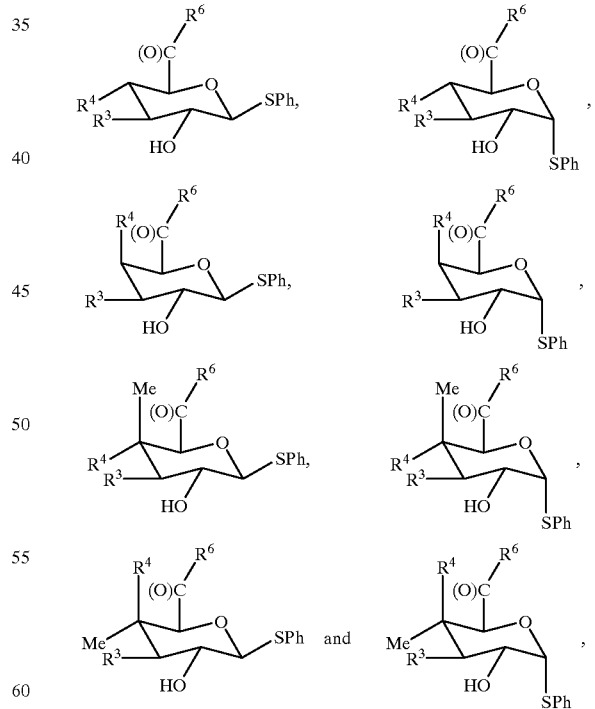

wherein

R³ is X—Y, where X is O— or NH—, and Y is alkyl, cycloalkyl, alkenyl, C(O)R, C(O)NHR, C(O)OR, or SO₂R, where R is alkyl, cycloalkyl, alkenyl, aryl, aralkyl, or heterocycle, or X—Y combine to form N₃;

$R^4$ is O—X, where X is H, alkyl, cycloalkyl, alkenyl, acyl, benzoyl, aryl or aralkyl; and $R^6$ is OH, $NH_2$, or NHMe.

Also contemplated are donor molecules that can be used in assembling the moenomycin analogs of the present invention. The donor molecules are typically prepared first as protected phenyl 1-thio saccharides, and are then converted by previously known methods, such as described in U.S. Ser. No. 08/281,167 and 60/013,800, and by the instant methods into their phenylsulfenyl counterparts, as described hereinbelow. Thus, preferred donor molecules have a formula selected from among the following:

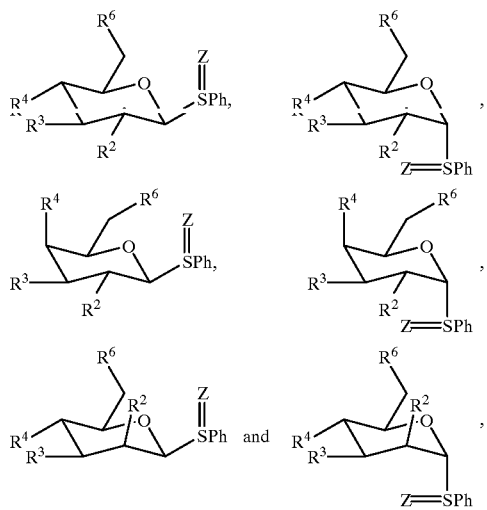

wherein

Z is O or is absent;

$R^2$ is X—Y, where X is O— or NH—, and Y is alkyl, cycloalkyl, alkenyl, C(O)R, C(O)NHR, C(O)OR, or $SO_2R$, where R is alkyl, cycloalkyl, alkenyl, aryl, aralkyl, or heterocycle, or X—Y combine to form $N_3$ or phthalimido;

$R^3$ is X—Y, where X is O— or NH—, and Y is alkyl, cycloalkyl, alkenyl, C(O)R, C(O)NHR, C(O)OR, or $SO_2R$, where R is alkyl, cycloalkyl, alkenyl, aryl, aralkyl, or heterocycle, or X—Y combine to form $N_3$, phthalimido, or a protected monosaccharide residue;

$R^4$ is X—Y, where X is O— or NH—, and Y is alkyl, cycloalkyl, alkenyl, C(O)R, C(O)NHR, C(O)OR, or $SO_2R$, where R is alkyl, cycloalkyl, alkenyl, aryl, aralkyl, or heterocycle, or X—Y combine to form $N_3$, phthalimido, or a protected monosaccharide residue, or $R^3$ and $R^4$ combine to form carbonato; and $R^6$ is H or X—Y, where X is O— or NH—, and Y is alkyl, cycloalkyl, alkenyl, C(O)R, C(O)NHR, C(O)OR, or $SO_2R$, where R is alkyl, cycloalkyl, alkenyl, aryl, aralkyl, or heterocycle, or X—Y combine to form $N_3$, phthalimido, or a protected monosaccharide residue.

As used herein, a "protected monosaccharide" is a monosaccharide that has had its hydroxyl and/or amino groups temporarily made non-reactive by masking groups.

Another aspect of the invention pertains to a method of synthesizing a combinatorial library of moenomycin analogs according to the principles of the present invention. Such a method involves synthesizing at least one compound having the formula:

wherein D, A, and P—R have the meanings described hereinabove. Accordingly, a preferred method of the present invention comprises the steps of:

(a) covalently linking an acceptor monosaccharide (A) to a support by forming a carboxylate or carboxyamide linkage between the C6 carbon of A and the support, wherein A is substituted at its anomeric carbon with a thiophenyl group;

(b) covalently linking the anomeric carbon of a donor saccharide (D) via an O-glycosidic linkage to the C2 carbon of A to form a D—A moiety linked to the support;

(c) coupling a lipophosphoglycerate mimetic group (P—R) to the anomeric position of the A residue of the D—A moiety to form a D—A—P—R moiety linked to the support; and (d) cleaving the D—A—P—R moiety from the support, which thereby affords the target compound.

In order to provide a wide range of structural diversity among the various members of an instant moenomycin analog library, hydroxyl groups on the acceptor and/or donor saccharide residues can be converted (derivatized) into other functionalities. For example, a hydroxyl group can be converted to an ester, carbamate, carbonate or sulfate functionality by reacting it with the appropriate compound. Alternatively, an azido group on a saccharide residue can be reduced to an amine, which can then be converted into an amide, carbamate, urea, sulfonamide, or substituted amine functionality. Reactants and reaction conditions for performing these conversions are well-known to those skilled in the art. Preferred methods of performing these functionalizations on a solid phase support have been reported by R. Liang, et al., Science, 274:1520 (1996) and are the subject of U.S. Ser. No. 08/823,328, filed Mar. 21, 1997, as well as U.S. Provisional application Serial No. 60/047946, filed May 29, 1997, the disclosures of which are incorporated herein by reference.

The above-mentioned functionalizations are preferably performed at the C3 position of residue A and/or the C2 position of residue D before or after performing the above step (b), which joins residues A and D via an O-glycosidic linkage.

The lipophosphoglycerate mimetic (P—R) group is linked to residue A after the A—D linkage has been made. The P—R group can be attached to A piecewise, that is, by attaching an oxidized phosphorus group first, followed by attaching a negatively charged functionality. However, it is generally preferable to form the P—R group separately prior to performing the above coupling step (c).

Various protecting groups, e.g., acetyl, benzoyl, levulinoyl, Nfmoc (N-fluorenylmethyloxycarbonyl), N-trifluoroacetamido, phthalimido, and the like, are used to direct the desired bond formations, as illustrated herein. These protecting groups will usually have been removed in the final moenomycin analog compound in order to restore the underlying chemical functionality, e.g., a hydroxyl group or an amino group. Generally, the protecting groups will be removed from the assembled D—A—P—R moiety after final assembly of the target molecule. Whenever the assembly is performed on a support, the removal of protecting groups is usually performed prior to cleaving the molecule from the support in step (d).

Although the above-described assembly steps can be performed without a support, i.e., in solution phase, use of a support is preferred since it permits the use of excess reactants to drive a reaction to completion and since physical separation of excess reactants and side products from the target compound can be performed through convenient wash steps. Solid phase supports are preferred, such as resins having a photo- or acid-cleavable linker, e.g., Rink amine resins, as well as silica, controlled porosity glass, polystyrene, and grafted polymers. Polyethylene glycol (PEG) is another type of support that can be employed.

A method of screening an instant library of compounds for anti-microbial activity is also contemplated. Such method comprises contacting a member of the library with a culture of target microbes and monitoring their rate of growth, such as after a predefined incubation period. Alternatively, a direct assay of anti-microbial activity entails determining peptidoglycan synthesis of the microbes is inhibited in the presence of the compound, as is discussed hereinafter.

The invention will now be described with reference to certain Schemes (shown in the Figures) and Examples. These Schemes and Examples illustrate but do not limit the invention. The compounds described hereinbelow are assigned numerical designations corresponding to the number of the scheme in which they are depicted and the compound number within that scheme.

PART I. SYNTHESIS OF ACCEPTOR SACCHARIDES

Example I-1
Synthesis of Phenyl 3-azido-3-deoxy-4-O-benzoyl-1-thio-β-D-glucopyranosiduronic acid (compound 1.11)

As shown in Scheme 1, trifluoromethanesulfonic anhydride (25 mL; 41.9 g; 148.7 mmol) is added dropwise over 10 min to a stirred solution of 1,2:5,6-di-O-isopropylidene-D-allofuranose (35 g; 35.0 mmol), commercially available from Pfanstiehl Laboratories, Inc. (Waukegan, Ill.), in dry pyridine (150 mL) under argon at −20° C. The reaction mixture is allowed to warm to room temperature over 2 h, then diluted with ethyl acetate (250 mL) and washed with ice-cold brine (800 mL). The aqueous layer is extracted once with a further portion of ethyl acetate (250 mL), then the combined organic layers are washed with 3N citric acid (2×500 mL) and brine (100 mL), then dried over $Na_2SO_4$ and evaporated to give compound 1.1 as a yellow brown oil (49.3 g; 125 mmol; 93%): Rf (30% ethyl acetate-hexane): 0.39. $^1$H NMR (300 MHz, $CDCl_3$): δ 1.32, 1.36, 1.43, 1.56(12H, 4×s, isopropylidene, $CH_3$, s); 3.88(1H, dd, J=4.8 and 8.7 Hz); 4.07–4.19(3H, m); 4.75(1H, t, J=5.7 Hz); 4.89(1H, dd, J=5.1 and 6.9 Hz), 5.82(1H, d, J=3.9 Hz, H-1). MS m/e 415 [M+Na].

Compound 1.1 (49.30 g; 126 mmol) and sodium azide (16.40 g; 252 mmol) are stirred in dry DMF (200 mL) at 100° C. for 30 min. The reaction mixture is cooled to room temperature, filtered, then diluted with water (200 mL) and extracted with ethyl acetate (2×150 mL). The organic layers are washed with water (2×300 mL) then brine (100 mL), dried over $Na_2SO_4$, and concentrated under reduced pressure to give compound 1.2 as a light yellow oil (37.3 g, quantitative yield); Rf (50% ethyl acetate-hexane): 0.64. $^1$H NMR (300 MHz, $CDCl_3$): δ 1.32, 1.36, 1.43, 1.51(12H, 4×s, isopropylidene $CH_3$ s); 3.99(1H, dd); 4.08–4.25(4H, m); 4.62(1H, d, J=3.3 Hz), 5.86(1H, d, J=3.3 Hz); MS m/e 308 [M+Na].

Compound 1.2 (106 g; 372 mmol) is dissolved in a mixture of trifluoroacetic acid (50 mL), dioxane (200 mL) and 1.1 M aqueous HCl (90 mL), and heated at 50–60° C. for 21 h. The reaction mixture is neutralized with sodium hydroxide and concentrated to give a quantitative yield of compound 1.3 as a brown oil. $^1$H NMR (300 MHz, $CD_3OD$): δ 3.1–3.75(10H, m), 4.55(½H, d, H-1); 5.05(½H, d, H-1). MS FAB: m/e 228 [M+Na].

A stirred solution of compound 1.3 (38.6 g; 180 mmol) in pyridine containing a catalytic amount of DMAP (0.5 g) is treated dropwise with acetic anhydride (147 g; 1.44mol). The reaction mixture is stirred overnight at room temperature then diluted with water (600 mL). After stirring for 20 min, the reaction mixture is extracted with ethyl acetate (2×500 mL). The combined organic phases are washed with saturated sodium bicarbonate solution (2×400 mL), 2N HCl (2×300 mL) and brine (200 mL), then dried over $Na_2SO_4$ and evaporated to give compound 1.4 as a brown oil (62.5 g; 166 mmol); Rf (50% ethyl acetate-hexane): 0.45. $^1$H NMR (300 MHz, $CDCl_3$): δ (2:1 mixture of β:α anomers at C-1) 2.04–2.11(12H, 8s, 4×[$O_2CCH_3$]); 3.66(1H, dd, J=9.0 and 9.9 Hz, H-3β); 3.76(1H, m, H-5β); 3.94(1H, t, J=10.2 Hz, H-3α); 3.98–4.23(3H, m); 4.88–5.03(2H, m); 5.64(⅔H, d, J=8.1 Hz, H-1β); 6.26(⅓H, d, J=3.6 Hz, H-1α). MS FAB: m/e 396 [M+Na].

$BF_3.Et_2O$ (50 mL; 40.6 mmol) is added to a stirred solution of compound 1.4 (56.0 g; 150 mmol) and thiophenol (30 ml; 28.7 mmol) in dry dichloromethane (125 mL). The reaction mixture is heated under reflux for 6 h then kept at room temperature for 16 h. The reaction mixture is diluted with dichloromethane (300 mL) and washed with water (300 mL), saturated sodium bicarbonate solution (3×600 mL), 2N hydrochloric acid (2×500 mL), water (600 mL) and brine (2×500 mL), then dried over $Na_2SO_4$ and evaporated to a yellow solid (72 g). The crude product containing both the alpha and beta isomers is recrystallized from ethyl acetate/hexane to give compound 1.5 (37.96 g; 90 mmol; 60%) as a white solid. mp 135° C. Rf (50% ethyl acetate-hexane): 0.53. $^1$H NMR (300 MHz, $CDCl_3$): δ 2.07, 2.11 and 2.17 (9H, 3×s, 3×$O_2CCH_3$); 3.66(2H, t and m, $J_t$=9.9 Hz, H-3 and H-5), 4.17(2H, m, 2×H-6); 4.65(1H, d, J=9.8 Hz, H-1β); 4.91 and 4.93(2H, 2×t, H-4 and H-2), 7.27–7.52(5H, m, Ar—H). FAB MS: m/e 445 [M+Na].

A stirred suspension of compound 1.5 (38.0 g; 90 mmol) in dry methanol (250 mL) is treated with sodium methoxide (4.0 g; 18.5 mmol) at room temperature under argon. After 2 h, the reaction mixture is adjusted to pH=7 with Dowex 50 ($H^+$) resin, then filtered and the filtrate is evaporated to give compound 1.6 as a white solid (28.0 g; quantitative yield). mp 159–160° C. Rf (ethyl acetate): 0.44. $^1$H NMR (300 MHz, $CD_3OD$): δ 3.18–3.39(4H, m); 3.66(1H, dd, J=10.5 and 5.4 Hz, H-6); 3.84(1H, d, J=10.5 and 2.0 Hz, H-6'); 4.64(1H, d, J=9.8 Hz, H-1β); 7.27–7.33(3H, m, Ar—H); 7.53–7.56(2H, d, Ar—H); MS m/e 320 [M+Na].

Compound 1.6 (28 g; 94 mmol) and trimethyl orthobenzoate (39 mL; 230 mmol) are stirred in anhydrous acetonitrile (250 mL) containing a catalytic amount of p-TSA (1.34 g) for 3 h at room temperature. The solvent is evaporated and the residue is redissolved in fresh anhydrous acetonitrile (250 mL) and stirred for a further 2 h. Solid sodium bicarbonate is added (8.6 g) and the crude compound 1.7 is concentrated under reduced pressure to a slurry. MS m/e 438 [M+Na] and 384 [M−OMe]. The mixture is treated with acetic anhydride (17 mL; 165 mmol), pyridine (80 mL) and 4-dimethylamino pyridine (70 mg) and the reaction mixture is stirred overnight at room temperature. (TLC 10% ethyl acetate-hexane showed no starting material.) The reaction mixture is poured into water (500 mL) and extracted with ethyl acetate (200 mL). The organic phase is washed with water (2×500 mL), saturated sodium bicarbonate solution (2×500 mL), 3N citric acid solution (2×500 mL) then water (2×5 mL) and dried over sodium sulfate. The solution is concentrated at 80° C. to remove most of the remaining trimethyl orthobenzoate, giving compound 1.8 as a yellow gel (50.1 g; quantitative yield). Rf (10% ethyl acetate-hexane): 0.3 1. $^1$H NMR (300 MHz, CDCl$_3$): δ 2.18(3H, S, O$_2$CCH$_3$); 3.09(3H, s, —OCH$_3$); 3.56(1H, dt, H-5); 3.75 (1H, t, J=10.2 Hz, H-3); 4.00–4.10(2H, m, 2×H-6); 4.18(1H, t, J=10.2 Hz, H-4); 4.72(1H, d, J=10.0 Hz, H-1); 4.90(1H, t, J=10.0 Hz, H-2); 7.26–7.60(10H, m, Ar—H).

A solution of compound 1.8 (50.1 g; 94 mmol) in acetonitrile (100 mL) is treated with a 9:1 (v:v) mixture of trifluoroacetic acid and water (20 mL). The solution turns reddish and a white precipitate is formed after 1 min. The suspension is stirred for 2 h then filtered to remove the solid 6-O-benzoate product (12 g). A second crop of the 6-O-benzoate is obtained by concentration of the filtrate to 40 mL and the remainder is evaporated to a yellow oil, containing primarily compound 1.9a with a little of the 6-O-benzoate regioisomer 1.9b and methyl benzoate. The crude product is triturated from diethyl ether-hexane to give compound 1.9a as a yellow-white solid (1 8.7 g; 42.3 mmol; 45%); mp 98–99° C. Alternatively, the crude product can be purified by column chromatography eluent; 20–50% ethyl acetate-hexane followed by 10% methanol dichloromethane.

Phenyl 2-O-acetly-3-azido-3-deoxy-4-O-benzoyl-1-thio-β-D-glucopyranoside (compound 1.9a)

Rf (50% ethyl acetate-hexane): 0.33. $^1$H NMR (300 MHz, CDCl$_3$): δ 2.18 (3H, s, O$_2$CCH$_3$); 3.6–3.8 (3H, m, H-5, 2×H-6); 3.89 (1H, t, J=9.8 Hz, H-3); 4.78 (1H, d, J=10.0 Hz, H-1); 4.98 (1H, t, J=9.8 Hz, H-2); 5.12 (1H, t, J=9.5 Hz, H-4); 7.3–7.35 (3H, m, —SAr—H); 7.44–7.51 (4H, m, 2×-SPh-H$_o$, 2×-Bz-H$_m$); 7.61 (1H, t, Bz-H$_p$); 8.03 (2H, d, Bz-H$_o$). MS m/e 466 [M+Na].

Phenyl 2-O-acetyl-3-azido-3-deoxy-6-O-benzoyl-1-thio-β-D-glucopyranoside (compound 1.9b)

Rf (50% ethyl acetate-hexane): 0.48. $^1$H NMR (300 MHz, CDCl$_3$): δ 2.17 (3H, s, O$_2$CCH$_3$); 2.49 (1H, br s, OH); 3.47 (1H, t, J=9.5 Hz); 3.61 (1H, t, J=9.5 Hz); 3.67 (1H, m, H-5); 4.59 (1H, dd, J=2.2 and 12.2 Hz, H-6); 4.67 (1H, d, J=10.0 Hz, H-1); 4.68 (1H, dd, J=4.6 and 12.2 Hz, H-6); 5.36 (1H, t, J=9.8 Hz, H-4); 7.14–7.26 (3H, m, —SAr—H); 7.44–7.49 (4H, m, 2×-SPh-H$_o$, 2×-Bz-H$_m$); 7.60 (1H, t, Bz-H$_p$); 8.03 (2H, d, Bz-H$_o$). MS m/e 466 [M+Na].

Preparation of Phenyl 2-O-acetyl-3-azido-3-deoxy-4-O-benzoyl-1-thio-β-D-glucopyranosiduronic acid (compound 1.10)

To a solution of compound 1.9a (4.88 g; 11.0 mmol) in acetone (75 mL) is added Jones reagent (25 mL) [prepared from chromium trioxide 11.3 g, concentrated sulfuric acid (10 mL) and water (74 mL)] and the reaction mixture is sonicated in a sonicator bath for 1 h at a temperature of about 35° C. A further portion of Jones reagent (10 mL) is added and the reaction mixture is sonicated for a further 1 h. Isopropanol is added (10 mL) and the reaction mixture is stirred for 20 min to destroy the excess oxidant. The top layer is decanted, and the green aqueous lower layer is extracted with more acetone (3×50 mL). The combined organic layers are combined and evaporated to give a greenish-white solid. The solid is taken up in ethyl acetate (150 mL) and extracted with 2N aq. HCl (20 mL) to remove the green color. Drying over sodium sulfate and evaporation gives compound 1.10 (5.1 g, quantitative yield) as a white solid. mp 170–172° C. Rf(15% methanol-dichloromethane): 0.48. $^1$H NMR (300 MHz, CDCl$_3$): δ 2.21(3H, S, O$_2$CCH$_3$); 3.97(1H, t, J=9.8 Hz, H-3); 4.21(1H, d, J=9.8 Hz, H-5); 4.85(1H, d, J=10.1 Hz, H-1); 5.01(1H, t, J=10.0 Hz, H-2); 5.36(1H, t, J=9.8 Hz, H-4); 7.33–7.64(8H, m, Ar—H); 8.03(2H, dd, OBz ortho protons). FAB MS: m/e 480 [M+Na] and 502 [M+2Na—H].

Guanidine hydrochloride (2.08 g; 21.88 mmol) is dissolved in ethanol (60 mL) and treated with sodium methoxide (1.16 g; 21.88 mmol). Sodium chloride is filtered off, and the filter cake is washed once with ethanol (60 mL) which is combined with the filtrate. This solution is added to a suspension of compound 1.10 (2.0 g; 4.37 mmol) in 9:1 ethanol-dichloromethane (20 mL) and stirred at room temperature for 4 h, at which time the reaction is shown to be complete by thin layer chromatography. Dowex 50 H$^+$ resin is added to neutralize the base, the resin is filtered off, and the filtrate is concentrated. Chromatography on silica eluent 2–15% methanol-DCM gives compound 1.11 as a white solid (1.72 g; 91%) mp 93–95° C. Rf (15% methanol-DCM): 0.41. $^1$H NMR (300 MHz, CDCl$_3$-CD$_3$OD): δ 3.30(1H, m, OH); 3.50(1H, t, J=9.8 Hz); 3.75(1H, t, J=9.5 Hz); 3.96(1H, d, J=9.8 Hz, H-5); 4.73(1H, d, J=9.8 Hz, H-1); 5.15(1H, t, J=9.8 Hz, H-4); 7.22–7.57(8H, m, Ar—H); 7.98–8.03(2H, d, OBz ortho protons); FAB MS: m/e 438 [M+Na] and 460 [M+2Na—H].

Example I-2
Synthesis of Phenyl 3-azido-3-deoxy-4-O-methyl-1-thio-β-D-gluco-pyranosiduronic acid (compound 2.4).

As is depicted in Scheme 2, to a solution of compound 2.1 (16 g; 0.037 mol) in anhydrous DMF (200 mL) is added silver oxide (16 g) with stirring. (The preparation of compound 2.1, which is also compound 1.9b, is described hereinabove.) Methyl iodide (25 mL; 0.401 mol) is added to the resulting suspension and the mixture is stirred at room temperature for 24 h. The reaction mixture is diluted with ethyl acetate (400 mL), filtered, washed with water, washed with brine, dried (Na$_2$SO$_4$) and concentrated. The crude compound is purified by flash column chromatography eluting with 20% EtOAc/hexane to afford compound 2.2 (15 g; 91%) as a white solid; mp 75–77 ° C.; $^1$H NMR (300 MHz, CDCl$_3$): δ 8.01(d, J=8.1 Hz, 2H, ArH), 7.5–7.4(m, 5H, ArH), 7.3–7.1(m, 3H, ArH), 4.84(t, J=10.2 Hz, 1H, H-2), 4.71(dd, J=12, 2.1 Hz, 1H, H-6 pseudo equatorial), 4.64(d, J=9 Hz, 1H, H-1), 4.44(dd, J=12, 6 Hz, 1H, H-6 pseudo axial), 3.71–3.53(m, 2H, H-3 and H-5, containing a singlet at 3.55, OMe), 3.21(t, J=9.3 Hz, 1H, H-4), 2.18(s, 3H, OAc). $^{13}$C NMR (75 MHz, CDCl$_3$): δ 169.15, 165.85, 133.15, 132.68, 132.65, 131.76, 129.56, 129.54, 129.52, 128.66, 128.35, 128.33, 127.94, 88.67, 78.46, 69.90, 67.84, 63.00, 60.66, 60.63, 20.75; FAB MS: m/z 480 (M+Na].

To a stirred solution of compound 2.2 (15 g; 0.033 mol) in anhydrous methanol (200 mL) is added sodium methoxide (3.65 g; 0.067 mol). The reaction mixture is stirred for 4 h at room temperature by which time all the starting material has been consumed (TLC analysis). Excess base is neutralized with Amberlite-H$^+$ resin, filtered and concentrated to afford compound 2.3 as a white solid in quantitative yield (mp 182–185° C.).

Jones reagent (0.7M; 36 mL) is added to a solution of compound 2.3 (9.67 g; 0.033 mol) in acetone (150 mL) and the mixture is sonicated. After one hour, another portion (0.7M; 30 mL) of Jones reagent is added and the sonication is continued for 45 mins. After TLC analysis, excess reagent is quenched with isopropanol (100 mL) and the chromate salt is filtered off through a pad of Celite. The green solid residue obtained after concentration is purified by flash chromatography eluting with 5% methanol/methylene chloride to afford compound 2.4 as a white foamy solid (mp 182–185° C.). $^1$H NMR (300 MHz, CDCl$_3$): δ 7.21–7.75(m, 5H, ArH), 4.58(d, J=9.3 Hz, 1H, H-1), 3.93(d, J=9.3 Hz, H-5), 3.44–3.62(m, 1H, H-3, containing a singlet at 3.54-OMe), 3.26–3.42(m, 2H, H-2,4); $^{13}$C NMR (75 MHz, CDCl$_3$): δ 171.56, 132.91, 132.42, 130.80, 129.11, 128.48, 88.72, 79.23, 77.66, 70.61, 68.72, 60.50; FAB MS: calcd for C$_{13}$O$_5$SH$_{15}$N$_3$ 325. Found 324 (–ve mode), 343 (+ve mode, M+18 (NH$_4$)).

Example I-3
Synthesis of Phenyl 3-azido-3-deoxy-4-O-benzoyl-1-thio-β-D-galactopyranosiduronic acid (compound 3.9) and Phenyl 3-azido-3-deoxy-4-O-methyl-1-thio-β-D-galactopyranosiduronic acid (compound 3.14)

As depicted in Scheme 3, phenyl 3-azido-3-deoxy-1-thio-β-D-glucopyranoside (compound 3.1) is prepared from 1,2-5,6-di-O-isopropylidene-α-D-allofuranose following the procedure described in Example I-1 for the preparation of compound 1.6.

To a stirred solution of compound 3.1 (5.0 g; 16.8 mmol) in DMF (50 mL) are added p-toluenesulfonic acid (0.5 g) and anisaldehyde dimethyl acetal (10 mL). The stirring is continued for 3 h at room temperature. The acid is neutralized with triethylamine, and the solution is concentrated under reduced pressure. The residue is dissolved in ethyl acetate and washed with aq. NaHCO$_3$ solution, water and concentrated. Treatment of the residue with ether-hexane gives pure compound 3.2 (5.9 g; 87% yield); $^1$H NMR (300 MHz, CDCl$_3$): δ 7.41–6.87(m, 9H, arom.), 5.51(s, 1H, acetal H), 4.61 (d, J=9.6 Hz, 1H, H-1), 4.37(dd, 1H, H-3), 3.79(s, 3H, OMe), 3.72(t, 1H, H-2), 3.48(d, J=9.3 Hz, 1H, H-5).

To an ice-cooled solution of compound 3.2 (5.7 g; 14.2 mmol) in pyridine (50 mL) containing DMAP (0.2 g) is added acetic anhydride (25 mL) and stirring is continued for 3 h at room temperature. The solvent is evaporated under reduced pressure and the last traces of solvent are removed by co-evaporation with toluene. The residue is dissolved in ethyl acetate and washed with aq. NaHCO$_3$ solution, water, dried over Na$_2$SO$_4$ and concentrated in vacuo. The residue gives compound 3.3 as a white amorphous solid (6.0 g; 95% yield) from ether-hexane; $^1$H NMR (300 MHz, CDCl$_3$): δ 7.45–6.87(m, 9H, arom.), 5.53(s, 1H, acetal H), 4.89(t, 1H, H-2), 4.73(d, J=9.9 Hz, 1H, H-1), 4.37(dd, 1H, H-3), 3.79(s, 3H, OMe), 2.18(s, 3H, OAc).

To a cold (0° C. bath) stirred mixture of compound 3.3 (5.5 g; 12.5 mmol), sodium cyanoborohydride (3.8 g; 52 mmol) and powdered 3A molecular sieves (10 g) in dry DMF (80 mL) is added dropwise a TFA solution (9.0 mL; 117 mmol) in DMF (20 mL). Stirring is continued at room temperature for 72 h. The mixture is diluted with ethyl acetate, and the solids are filtered through Celite and washed with ethyl acetate. The combined filtrate is washed with aq. NaHCO$_3$ solution, water, dried and concentrated under reduced pressure. The residue is purified on a column of silica gel and eluted with hexane-ethyl acetate (4:1→1:1 v/v) to afford compound 3.4 as an amorphous solid (5.1 g; 90%); $^1$H NMR (300 MHz, CDCl$_3$): δ 7.43–6.81(m, 9H, arom.), 4.81(t, 1H, H-2), 4.60(d, J=9.9 Hz, 1H, H-1), 4.43 (dd, 1H,H-3), 3.73 (s, 3H, OMe), 2.11(s, 3H, OAc); $^{13}$C NMR: δ 132.39–127.79(aromatic C), 86.05(C-1), 78.51(C-5), 73.23(OCH$_2$), 70.40(C-3), 70.36(C-6), 70.10 (C-2), 67.92(C-4), 55.06(OCH$_3$), 20.68(COCH$_3$).

To a stirred solution of triflic anhydride (3.0 mL; 18 mmol) in CH$_2$Cl$_2$ (120 mL) at a temperature of –15° C. is added dropwise pyridine (3.5 mL; 43 mmol) followed by a solution of compound 3.4 (5.0 g; 10.9 mmol) in CH$_2$Cl$_2$ (100 mL). After 3 h at the same temperature, the solution is diluted with DCM, washed with 10% aq. citric acid, aq. NaHCO$_3$ solution, water, dried over Na$_2$SO$_4$ and concentrated under reduced pressure. To a solution of this triflate (compound 3.5) in dry toluene (150 mL) is added tetrabutyl ammonium benzoate (6.0 g; 1.5 equivalent). The reaction is stirred at room temperature for 0.5 h. The solvent is evaporated in vacuo and the residue is purified on a silica gel column by using hexane-ethyl acetate (4:1→3:1; v/v) as eluent to give compound 3.6 (5.3 g; 92%); $^1$H NMR (300 MHz, CDCl$_3$): δ 7.89–6.75(m, 14H, arom.), 5.73(d, J=2.7 Hz, 1H, H-4), 5.22(t, 1H, H-2), 4.71(d, J=9.9 Hz, 1H, H-1), 3.92(t, 1H, H-3), 3.72(s, 3H, OMe), 2.15(s, 3H, OAc); $^{13}$C NMR: δ 133.39–128.11(aromatic C), 85.77(C-1), 77.43(C-5), 73.25(OCH$_2$), 68.44(C-3 & C-6), 67.64(C-2), 63.68(C-4), 55.11(OMe), 20.82(COCH$_3$).

To a solution of compound 3.6 (5.2 g; 9.3 mmol) in CH$_2$Cl$_2$ (150 mL) saturated with water is added DDQ (5.2 g; 23 mmol) and stirring is continued for 2 h. The organic layer is washed with cold aq. NaHCO$_3$ solution, water, dried and concentrated under reduced pressure. The residue is purified by column chromatography using a solvent gradient consisting of (4:1→1:1, v/v) hexane-ethyl acetate to give compound 3.7 (3.7 g; 90%); $^1$H NMR (300 MHz, CDCl$_3$): δ 7.89–7.32(m, 10H, arom.), 5.59(d, J=3.0 Hz, 1H, H-4), 5.32(t, 1H, H-2), 4.73(d, J=9.6 Hz, 1H, H-1), 3.83(t, 1H, H-3), 2.18(s, 3H, OAc); $^{13}$C NMR: δ 169.24 & 166.57(2× CO), 133.39–128.35(aromatic C), 85.77(C-1), 78.25(C-5), 69.22(C-3), 68.38(C-2), 63.01(C-4), 60.36 (C-6), 20.85 (COCH$_3$).

A mixture of compound 3.7 (3.6 g; 8.1 mmol) in acetone (100 mL) containing Jones reagent (13.8 mL) is sonicated for 1 h. Then, another batch of Jones reagent (13.8 mL) is added to the reaction mixture and sonication is performed for another 1 h. Isopropanol is added to decompose the excess of reagent. The reaction mixture is filtered through Celite and the solid is washed with an excess of acetone. The solvent is removed under reduced pressure and the residue is dissolved in ethyl acetate and washed with aq. NaCl solution, dried over Na$_2$SO$_4$, and concentrated. It is purified on a silica gel column using CH$_2$Cl$_2$-acetone (4:1→1:1, v/v) as eluent to give compound 3.8 (2.9 g; 78%); $^1$H NMR (300 MHz, CD$_3$OD): δ 7.87–7.38(m, 10H, arom.), 6.025(dd, J=1.2 Hz, 1H, H-4), 5.13(t, 1H, H-2), 4.95(d, J=9.9 Hz, 1H, H-1), 4.67(d, J=1.2 Hz, 1H, H-5), 4.19(dd, 1H, H-3), 2.18(s, 3H, OAc); $^{13}$C NMR: δ 171.01, 169.53 & 166.51(3×CO), 135.32–129.54(aromatic C), 86.17(C-1), 77.07(C-5), 71.23 (C-3), 69.21(C-2), 64.23(C-4), 20.86(COCH$_3$).

To a solution of compound 3.8 (1.9 g) in methanol (100 mL) is added 7.4% (w/v)mg(OMe)$_2$ solution in methanol (8 mL; 1 equiv.), which is stirred at room temperature for 16 h. Excess base is neutralized with glacial acetic acid and concentrated under reduced pressure. The residue is dissolved in ethyl acetate and washed with aq. NaCl solution, dried over Na$_2$SO$_4$ and evaporated in vacuo. The residue is purified on a silica gel column using a solvent gradient consisting of 10–15% MeOH in CH$_2$Cl$_2$ to give compound 3.9 (1.6 g; 93%); $^1$H NMR (300 MHz, CD$_3$OD): δ 7.87–7.38 (m, 10H, arom.), 5.95(d, J=2.4 Hz, 1H, H-4), 4.75(d, J=9.6 Hz, 1H,H-1), 4.54(bs, 1H, H-5), 3.92(dd, 1H, H-3), 3.68(t, 1H, H-2); $^{13}$C NMR: δ 166.51 & 166.52(2×CO), 135.12–129.18(aromatic C), 88.87(C-1), 71.69(C-3), 69.07 (C-2), 66.72(C-4): IR(KBr): 2111.97(N$_3$), 1727.61(CO). ESMS: Calcd. For C$_{19}$H$_{17}$N$_3$SO$_6$(415); Found: 414[M–1]$^-$.

To a solution of triflate 3.5 in dry DMF (100 mL) is added NaNO$_2$ (12 g; 8 equiv.). The reaction mixture is stirred at room temperature for 1 h and is diluted with ethyl acetate and washed with water, aq. NaHCO$_3$ solution, dried over Na$_2$SO$_4$ and concentrated in vacuo. The residue is purified on a silica gel column using hexane-ethyl acetate (4:1→3:2;

v/v) as eluent to give compound 3.10 (7.1 g; 75%); $^1$H NMR (300 MHz, CDCl$_3$): δ 7.50–6.87(m, 9H, arom.), 5.33(t, 1H, H-2), 4.67(d, J=9.9 Hz, 1H, H-1), 4.50(d, J=1.5 Hz, 1H, H-4), 4.15(t, 1H, H-3), 3.81(s, 3H, OMe), 2.16(s, 3H, OAc); $^{13}$C NMR: δ 132.83–127.86(aromatic C), 86.85(C-1), 77.54 (C-5), 73.47(OCH$_2$Ph), 69.21(C-6), 69.00(C-3), 68.37(C-2), 64.92(C-4), 55.26(OCH$_3$), 20.87(COCH$_3$).

A mixture of compound 3.10 (7.0 g; 15.2 mmol), Ag$_2$O (28 g), and CH$_3$I (21 mL) in dry DMF (100 mL) is stirred for 24 h at room temperature. The mixture is diluted with ethyl acetate, and the solids are removed by filtration through a Celite bed and thoroughly washed with ethyl acetate. The combined filtrate is washed with aq. sodium thiosulfate, water, dried over Na$_2$SO$_4$ and evaporated under reduced pressure. The residue gives compound 3.11 (5.0 g; 69%) as an amorphous solid from ether-hexane. $^1$H NMR (300 MHz, CDCl$_3$): δ 7.48–6.87(m, 9H, arom.), 5.3 1(t, 1H, H-2), 4.65(d, J=10.2 Hz, 1H, H-1), 4.47(d, J=1.8 Hz, 1H, H-4), 3.81(s, 3H, OMe), 3.72(dd, 1H, H-3), 3.54(s, 3H, OMe), 2.14(s, 3H, OAc); $^{13}$C NMR: δ 133.51–127.60 (aromatic C), 87.14(C-1), 77.78(C-4), 77.60(C-5), 73.24 (OCH$_2$Ph), 68.53(C-6), 67.53(C-3), 64.25(C-2), 61.38 (OCH$_3$), 55.24(OCH$_3$), 20.84(COCH$_3$).

To a solution of compound 3.11 (5.0 g; 10.6 mmol) in CH$_2$Cl$_2$ (150 mL) saturated with water is added DDQ (5.5 g; 24.4 mmol) and stirring is continued for 2 h. The organic layer is washed with cold aq. NaHCO$_3$, water, dried over Na$_2$SO$_4$ and concentrated in vacuo. The residue yields compound 3.12 (3.1 g; 83%) as an amorphous solid from ether-hexane. $^1$H NMR (300 MHz, CDCl$_3$): δ 7.45–7.28(m, 5H, arom.), 5.31(t, 1H, H-2), 4.68(d, J=9.9 Hz, 1H, H-1), 3.64(d, J=3.3 Hz, 1H, H-4), 3.55(s, 3H, OMe), 3.39–3.34 (dd, 1H, H-3), 2.15(s, 3H, OAc); $^{13}$C NMR: δ 169.45(CO), 133.25–127.68(aromatic C), 86.92(C-1), 79.70(C-4), 78.09 (C-5), 68.56(C-3), 64.27(C-2), 61.47(OCH$_3$), 20.84 (COCH$_3$).

A mixture of compound 3.12 (1.2 g; 3.4 mmol) in acetone (30 mL) containing Jones reagent (5 mL) is sonicated for 1 h. Then, another batch of Jones reagent (2.5 mL) is added to the reaction mixture and sonicated for another 1 h. Isopropanol is added to decompose the excess of reagent. The reaction mixture is filtered through Celite and the solid is washed with excess of acetone. The solvents are removed under reduced pressure and the residue is dissolved in ethyl acetate and washed with aq. NaCl solution, dried over Na$_2$SO$_4$ and concentrated in vacuo. It is purified by silica gel column using 10–15% MeOH in CH$_2$Cl$_2$ as eluent to give compound 3.13 (0.8 g; 64%); $^1$H NMR (300 MHz, CD$_3$OD): δ 7.58–7.33(m, 5H, arom.), 5.22(t, 1H, H-2), 4.87(d, J=9.6 Hz, 1H, H-1), 4.37(d, J=1.2 Hz 1H, H-5), 4.18–4.16(dd, J=1.2 Hz, 1H, H-4), 3.77–3.73(dd, J=3.3 Hz, 1H, H-3), 3.35(s, 3H, OMe), 2.17(s, 3H, OAc); $^{13}$C NMR: δ 171.19 & 170.81(2×CO), 133.25–128.93(aromatic C), 87.78(C-1), 80.53(C-4), 77.83(C-5), 69.52(C-3), 65.00(C-2), 61.52 (OCH$_3$), 20.84(COCH$_3$).

To a solution of compound 3.13 (1.2 g) in MeOH (100 mL) is added 1M MeONa (15 mL) and the resultant is stirred at room temperature for 3 h. The base is neutralized with IR-120 H+ resin, filtered and concentrated under reduced pressure. The residue is purified on a silica gel column using a solvent gradient consisting of 10–15% MeOH in CH$_2$Cl$_2$ to give compound 3.14 (0.9 g; 85% yield). $^1$H NMR (300 MHz, CD$_3$OD): δ 7.64–7.31(m, 5H, arom.), 4.67(d, J=9.6 Hz, 1H, H-1), 4.30(bs, 1H, H-5), 4.04(d, J=2.4 Hz, 1H, H-4), 3.78(t, 1H, H-2), 3.54(s, 3H, OMe); $^{13}$CNMR; 170.89(CO), 134.97–128.55(aromatic C), 90.41(C-1), 80.53(C-4), 77.78 (C-5), 69.20(C-3), 67.34(C-2), 61.53(OCH$_3$). ES-MS: Calcd. For C$_{13}$H$_{15}$N$_3$O$_5$S(325): Found: 324[M−1]$^-$, 343 [M+NH4]+, 348[M+Na]+.

Example I-4
Synthesis of Phenyl 4-O-benzoyl-3-O-levulinoyl-1-thio-β-D-galactopyranosiduronic acid (compound 4.10)

As shown in Scheme 4, 1,2,3,4,6-penta-O-acetyl-D-galactopyranose (compound 4.1) (58 g; 131 mmol), commercially available from Pfanstiehl Laboratories, Inc. (Waukegan, Ill.), is reacted with BF$_3$.etherate (28 mL; 233 mmol) and thiophenol (25 mL; 227 mmol) in CH$_2$Cl$_2$ (500 mL) at room temperature to give compound 4.2. De-O-acetylation with methanolic sodium methoxide provides compound 4.3 in 75% yield. To an ice-cold solution of compound 4.3 (20 g; 73.5 mmol), imidazole (17 g; 250 mmol) in dry DMF (200 mL) and tert-butyldimethylsilyl chloride (18 g; 120 mmol) are added with stirring, and stirring is continued for 3 h at 0° C. The reaction mixture is poured into an ice-water mixture and extracted with ethyl acetate, dried over Na$_2$SO$_4$ and the solvent is removed under reduced pressure. The residue is purified on a column of silica gel with 60–80% ethyl acetate in hexane as the eluent to give compound 4.4 (22.2 g; 78%); $^1$H NMR (300 MHz, CDCl$_3$): δ 7.53–7.25 (m, 5H, arom.), 4.53 (d, J=9.9 Hz, 1H, H-1), 0.89 (s, 9H, CMe$_3$), 0.085 and 0.07 (each s, 6H, Sime$_2$).

To a solution of compound 4.4 (10 g; 25.9 mmol) in dry toluene (150 mL) are added triethyl orthobenzoate (15 mL) and p-toluenesulfonic acid (0.1 g). After stirring for 1 h at room temperature, triethylamine is added and the solution is washed with water and is concentrated under reduced pressure. To a solution of this orthoester in dry DMF (100 mL) is added NaH (1.34 g, 60% mineral in oil suspension) at −20° C. After 0.5 h, allyl bromide (2.8 mL) is added and stirring is continued for 2 h at the same temperature. The reaction mixture is diluted with ethyl acetate, washed with water and solvent is removed under reduced pressure. The residue is dissolved in 80% aq. acetic acid (300 mL) and stirred for 1 h at room temperature. Acetic acid is evaporated in vacuo, and the last trace is removed by co-evaporation with toluene. The crude product is purified on a silica gel column by using a solvent gradient consisting of (3:1→1:4, v/v) hexane-ethyl acetate to give compound 4.5 (7.5 g, 44%); $^1$H NMR (300 MHz, CDCl$_3$): δ 8.04–7.32 (m, 10 H, arom.), 6.05–5.88 (m, 1H, allylic H), 5.68 (d, J=3.3 Hz, 1H, H-4), 5.27–5.15 (2d, 2H, vinylic H), 4.65 (d, J=9.6 Hz, 1H, H-1), 0.83 (s, 9H, CMe$_3$), −0.03–0.07 (each s, 6H, SiMe$_2$). The loss of a silyl group from compound 4.5 also gives compound 4.6 (4.2 g, 25%); $^1$H NMR (300 MHz, CDCl$_3$): δ 7.98–7.30 (m, 10H, arom.), 6.04–5.88 (m, 1H, allylic H), 5.51 (d, J=3.3 Hz, 1H, H-4), 5.27–5.17 (2d, 2H, vinylic H), 4.63 (d, J=9.6 Hz, 1H, H-1).

To a stirred solution of compound 4.5 (7 g; 13.2 mmol) in CH$_2$Cl$_2$ (100 mL) are added levulinic acid (3.6 mL; 41.8 mmol), DCC (5.5 g; 26.7 mmol) and DMAP (0.4 g) and stirring is continued for 3 h at room temperature. The precipitate is removed by filtration and the filtrate is washed with aq. NaHCO$_3$, water, and dried over Na$_2$SO$_4$, filtered and concentrated under reduced pressure. The residue is applied to a column of silica gel and is eluted with hexane-ethyl acetate (3:1, v/v) to give compound 4.7 (8.2 g; 98%). $^1$H NMR (300 MHz, CDCl$_3$): δ 7.98–7.33(m, 10H, arom.), 5.81–5.94(m, 1H, allylic H), 5.70(d. J=3.3 Hz, 1H, H-4), 5.25–5.10(m,3H, H-3 & vinylic H), 4.69(d, J=9.6 Hz, 1H, H-1), 2.85–2.37(m, 4H, 2×COCH$_2$), 2.11(s, 3H, COCH$_3$), 0.81(s, 9H, CMe$_3$), −0.05 and −0.10(each s, 6H, SiMe$_2$).

To a stirred solution of compound 4.7 (7.5 g; 12 mmol) in CH$_2$Cl$_2$ (120 mL) is added BF$_3$.etherate (1.8 mL; 14.3 mmol) and stirring is continued at room temperature for 4 h. The organic layer is washed with aq. NaHCO$_3$ solution, dried over Na$_2$SO$_4$ and concentrated in vacuo. The crude material is purified on a silica gel column using hexane ethyl acetate (3:2→2:3) as eluent to give compound 4.8 (5.1 g; 83%); $^1$H NMR (300 MHz, CDCl$_3$): δ 7.97–7.33 (m, 10H, arom.), 5.97–5.83 (m, 1H, allylic H), 5.60 (d, J=3.3 Hz, 1H, H-4), 5.26–5.09 (m, 3H, H-3 & vinylic H), 4.71 (d, J=9.6 Hz, 1H, H-1), 2.89–2.34 (m, 4H, 2×COCH$_2$), 2.07 (s, 3H, COCH$_3$); $^{13}$C NMR: δ 134.38–127.87(aromatic C), 117.24 (=CH), 86.97(C-1), 77.42(C-2), 74.74(C-5), 74.17(C-3), 68.93(C-4), 60.90(C-6), 37.73 and 27.82 (CH$_2$ & CH$_3$).

A mixture of compound 4.8 (5.5 g; 10.7 mmol) in acetone (100 mL) containing Jones reagent (28 mL) is sonicated for 2 h. Then, isopropanol is added to decompose excess of reagent. The reaction mixture is filtered off through Celite and the solid is washed with acetone. The solvent is removed under reduced pressure and the residue is dissolved in ethyl acetate and washed with aq. NaCl solution, dried over Na$_2$SO$_4$ and concentrated. The product is purified on a silica gel column using 10–15% MeOH in CH$_2$Cl$_2$ as eluent to give compound 4.9 (2.6 g; 46%); $^1$H NMR (300 MHz, CD$_3$OD): δ 7.98–7.35(m, 10H, arom.), 5.99(d, J=3.3 Hz, 1H, H-4), 5.95–5.81(m, 1H, allylic H), 5.21–3.64(m, 3H, H-3 & vinylic H), 4.81 (d, J=9.6 Hz, 1H, H-1), 4.32(bs, 1H, H-5), 3.64(dd, J=9.6 Hz, 1H, H-2), 2.78–2.35(m, 4H, 2×COCH$_2$), 2.05(s, 3H, COCH$_3$); $^{13}$C NMR: δ 136.09–128.80(aromatic C), 117.25(=CH), 87.75(C-1), 78.29(C-5), 76.29(C-2), 75.54(C-3), 72.13(C-4), 38.42, 29.59 & 28.97(CH$_2$ & CH$_3$).

A mixture of compound 4.9 (1.0 g; 1.9 mmol), 10% Pd—C (1.0 g) and p-oluenesulfonic acid monohydrate (0.25 g) in MeOH (43 mL) and water (8 mL) is refluxed with stirring for 72 h. The solid material is then filtered off through Celite and the filtrate is concentrated under reduced pressure. The residue is dissolved in ethyl acetate and washed with aq. NaCl solution, dried and evaporated under pressure. Column chromatographic purification on silica gel with 15–20% MeOH in CH$_2$Cl$_2$ gives compound 4.10 (0.3 g; 40%); $^1$H NMR (300 MHz, CD$_3$OD): δ 7.98–7.35(m, 10H, arom.), 5.99(d, J=2.7 Hz, 1H, H4), 5.09(dd, 1H, H3), 4.78(d, J=9.9 Hz, 1H, H-1), 4.37(bs, 1H, H-5), 2.73–2.34(m, 4H, 2×COCH$_2$), 2.07(s, 3H, COCH$_3$); $^{13}$C NMR: δ 134.69–126.95(aromatic C), 88.53(C-1), 78.31(C-5), 76.57 (C-3), 72.03(C-4), 67.61(C-2), 38.52, 29.60 & 28.93(CH$_2$ & CH$_3$). FAB-MS: Calcd. For C$_{24}$H$_{24}$O$_9$S(488); Found: 487 [M–H]$^-$ and 533 [M+2Na]$^+$.

Example I-5
Synthesis of Phenyl 3-O-levulinoyl-4-O-benzoyl-1-thio-β-D-glucopyranosiduronic acid (compound 5.14)

As depicted in Scheme 5, 1,2,3,4,6-penta-O-acetyl-D-glucopyranose (compound 5.1) (100 g; 255 mmol), commercially available from Pfanstiehl or Aldrich Chemical (Milwaukee, Wis.), is reacted with BF$_3$.etherate (62.5 mL; 492 mmol) and thiophenol (55 mL; 534 mmol) in CH$_2$Cl$_2$ (500 mL) at room temperature for 16 h to give compound 5.2 (92.5 g; 82%); $^1$H NMR (300 MHz, CDCl$_3$): δ 7.48–7.30 (m, 5H, arom.), 5.21 (t, J=9.3 Hz, 1H, H-4), 5.03 (t, J=10.2 Hz, 1H, H-3), 4.96 (t, J=10.2 Hz, 1H, H-2), 4.70 d, J=10.2 Hz, 1H, H-1), 2.08, 2.07, 2.01 & 1.98 (each s, 12H, 4×OAc).

De-O-acetylation of 5.2 (50 g) with methanolic sodium methoxide provides compound 5.3 (28 g; 91% yield); $^1$H NMR (300 MHz, CD$_3$OD): δ 7.57–7.23 (m, 5H, arom.), 4.60 (d, J=9.6 Hz, 1H, H-1), 3.84 (dd, 1H, H-4), 3.59 (dd, 1H, H-3); $^{13}$C NMR: δ 132.64–128.27 (aromatic C) 89.35 (C-1), 81.97(C-5), 79.63(C-3), 73.72(C-2), 71.29(C-4), 62.83(C-6).

To a stirred solution of compound 5.3 (20 g; 73.5 mmol) in DMF (150 mL) are added p-toluenesulfonic acid (0.8 g) and anisaldehyde dimethyl acetal (30 mL; 176 mmol). Stirring is continued for 3 h at room temperature. The acid is neutralized with triethylamine, and the solution is concentrated under reduced pressure. The residue is dissolved in ethyl acetate and washed with aq. NaHCO$_3$ solution, water, dried and concentrated. Treatment of the residue with ether-hexane gives compound 5.4 (23 g; 80%); $^1$H NMR (300 MHz, CDCl$_3$): δ 7.53–7.30(m, 7H, arom.), 6.87(d, J=8.7 Hz, 2H, arom.), 5.51 (s, 1H, acetal H), 4.69(d, J=9.9 Hz, 1H, H-1), 4.25(t, J=10.2 Hz, 1H, H-4), 3.77(s, 3H, OMe), 3.72(t, J=9.9 Hz, 1H, H-3), 3.67(dd, 1H, H-2).

A mixture of compound 5.4 (7.0 g; 18 mmol) in CH$_2$Cl$_2$ (300 mL), 5% aq. NaOH solution (30 mL), allyl bromide (2.7 mL; 31 mmol) and tetrabutylammonium hydrogen sulfate (2.0 g; 6.0 mmol) is refluxed for 72 h, and the two layers are separated. The organic layer is washed with water, dried over Na$_2$SO$_4$, and evaporated to give a crude product which is purified by column chromatography using hexane-ethyl acetate (4:1→3:2, v/v) to afford di-O-allyl derivative 5.5 (1.2 g; 14%), 3-O-allyl compound 5.6 (0.7 g; 9%) and the desired 2-O-allyl compound 5.7 (5.1 g; 66%); $^1$H NMR (300 MHz, CDCl$_3$): δ 7.54–7.31 (m, 7H, arom.), 6.88 (d, J=8.1 Hz, 2H, arom.), 6.12–5.82 (m, 1H, allylic H), 5.48 (s, 1H, acetal H), 5.34–5.19 (m, 2H, vinylic H), 4.68 (d, J=9.3 Hz, 1H, H-1), 3.78(s, 3H, OMe); $^{13}$C NMR: δ 134.60–127.54 (aromatic C), 117.51(=CH), 101.66 (acetal C),87.83(C-1), 80.42(C-5), 80.16(C-2), 75.24(C-4), 74.30 (OCH$_2$), 70.01(C-3), 68.51(C-6), 55.22(OMe).

To a stirred solution of compound 5.7 (5.0 g; 11.7 mmol) in CH$_2$Cl$_2$ (50 mL) are added levulinic acid (4.0 mL; 46.5 mmol), DCC (5.5 g; 26.7 mmol) and DMAP (0.6 g). Stirring is continued for 2 h at room temperature. The precipitate is removed by filtration and the filtrate is washed with aq. NaHCO$_3$, water and dried over Na$_2$SO$_4$, filtered and concentrated under reduced pressure. The residue is applied to a column of silica gel and is eluted with hexane-ethyl acetate (4:1→3:2, v/v) to give compound 5.8 (5.1 g; 83%); $^1$H NMR (300 MHz, CDCl$_3$): δ 7.54–7.31(m, 7H, arom.), 6.86(d, J=9.0 Hz, 2H, arom.), 6.02–5.87(m, 1H, allylic H), 5.43(s, 1H, acetal H), 5.31(t, J=9.0 Hz, 1H, H-3), 5.29–5.17(m, 2H, vinylic H), 4.75(d, J=8.7 Hz, 1H, H-1), 3.78(s, 3H, OMe), 2.81–2.61(m, 4H, COCH$_2$), 2.14(s, 3H, COCH$_3$); $^{13}$C NMR: δ 134.30–127.42(aromatic C), 117.51(=CH), 101.21(acetal C), 88.30(C-1), 78.73(C-5), 78.36(C-2), 74.71(C-4), 74.09 (OCH$_2$), 70.31(C-3), 68.46(C-6), 55.22(OMe), 37.83, 29.80 & 27.96(CH$_2$ & CH3).

A solution of compound 5.8 (3.5 g) in CH$_2$Cl$_2$ (50 mL) and trifluoroacetic acid (5.0 mL) is stirred at room temperature for 1 h. After the solvent is removed under reduced pressure, the residue is chromatographed using a solvent gradient consisting of CH$_2$Cl$_2$—acetone (4:1→3:2, v/v) to give compound 5.9 (1.8 g; 66%); $^1$H NMR (300 MHz, CDCl$_3$): δ 7.51–7.28(m, 5H, arom.), 5.95–5.78(m, 1H, allylic H), 5.25–5.13(m, 2H, vinylic H), 5.06(t, J=9.3 Hz, 1H, H-3), 4.70(d, J=9.6 Hz, 1H, H-1), 3.64(t, J=9.3 Hz, 1H, H-4), 3.34(t, J=9.3 Hz, 1H, H-2), 2.95–2.43(m, 4H, COCH$_2$), 2.17(s, 3H, COCH$_3$); $^{13}$C NMR: δ 34.36–127.70 (aromatic C) 117.31(=CH), 87.28(C-1), 79.32(C-5), 79.21 (C-2), 77.91(C-3), 73.78(OCH$_2$), 69.75(C-4), 62.43(C6), 38.26, 29.78 & 28.19(CH$_2$ & CH$_3$).

To an ice-cold, stirred solution of compound 5.9 (1.8 g; 4.4 mmol) and imidazole (0.68 g; 10 mmol) in dry DMF (15 mL) is added tert-butyldimethylsilyl chloride (0.72 g; 4.8 mmol), and stirring is continued for 1 h at 0° C. The reaction mixture is diluted with ethyl acetate and washed with water, dried over Na$_2$SO$_4$ and solvent is removed in vacuo. The residue is purified in a column of silica gel with hexane-ethylacetate (4:1→1:1, v/v) as an eluent to give compound 5.10 (2.1 g; 91%); $^1$H NMR (300 MHz, CDCl$_3$): δ 7.52–7.26 (m, 5H, arom.), 5.95–5.78(m, 1 H, allylic H), 5.24–5.12(m, 2H, vinylic H), 5.07(t, J=9.3 Hz, 1H, H3), 4.64(d, J=9.9 Hz, 1H, H-1), 2.85–2.53(m, 4H, COCH$_2$), 2.18(s, 3H, COCH$_3$), 0.90(s, 9H, CMe$_3$), 0.08 & 0.07(eachs, 6H, SiMe$_2$); $^{13}$C NMR: δ 134.36–127.44(aromatic C), 117.20(=CH), 87.31 (C-1), 79.04(C-5 & C-2), 77.63(C-3), 73.70(OCH$_2$), 70.55 (C-4), 63.73(C-6), 38.19, 29.80 & 28.18(CH$_3$ & CH$_2$).

To an ice cold solution of compound 5.10 (2.0 g; 3.8 mmol) in pyridine (30 mL) containing DMAP (0.1 g) is added benzoyl chloride (1.1 mL; 9.8 mmol) and stirring is continued for 16 h at room temperature. The solvent is evaporated under reduced pressure and the last traces are removed by co-evaporation with toluene. The residue is dissolved in ethyl acetate and washed with aq. NaHCO$_3$ solution, water, dried over Na$_2$SO$_4$ and concentrated in vacuo. Chromatographic purifaction with a solvent gradient consisting of hexane-ethyl acetate (4:1→3:1, v/v) as an eluent gives compound 5.11 (2.1 g; 88%) as a syrup; $^1$H NMR (300 MHz, CDCl$_3$): δ 7.98–7.28(m, 10H, arom.), 5.98–5.81(m, 1H, allylic H), 5.37(dd, J=9.6 & 9.0 Hz, 1H, H-4), 5.22(dd, J=9.6 & 9.0 Hz, 1H, H-3), 5.24–5.13(m, 2H, vinylic H), 4.71(d, J=9.6 Hz, 1H, H-1), 3.46(t, J=9.0 Hz, 1H, H-2), 2.58–2.35 (m, 4H, COCH$_2$), 2.00(s, 3H, COCH$_3$), 0.85(s, 9H, CMe$_3$), −0.01–0.04 (each s, 6H, SiMe$_2$); $^{13}$C NMR: δ 134.29–127.56(aromatic C), 117.47(=CH), 87.33 (C-1), 78.93(C-5), 77.69(C-2), 77.42(C-3), 73.84(OCH$_2$), 69.24(C-4), 62.58(C-6), 37.70, 27.98 & 25.77(CH$_2$ & CH$_3$).

To a stirred solution of compound 5.11 (1.9 g; 3 mmol) in CH$_2$Cl$_2$ (20 mL) is added BF$_3$.etherate (0.45 mL; 3.6 mmol) and stirring is continued at room temperature for 2 h. The organic layer is washed with aq. NaHCO$_3$ solution, dried over Na$_2$SO$_4$ and concentrated in vacuo. The product is purified on a silica gel column by using hexane-ethyl acetate (3:2→2:3, v/v) as eluent to give compound 5.12 (1.3 g; 84%); $^1$H NMR (300 MHz, CDCl$_3$): δ 7.96–7.28(m, 10H, arom.), 5.94–5.81(m, 1H, allylic H), 5.41(t, J=9.6 Hz, 1H, H-4), 5.25–5.11(m, 3H, H-3 & vinylic H), 4.72(d, J=9.9 Hz, 1H, H-1), 3.45(t, 1H, H-2), 2.76–2.28(m, 4H, 2×COCH$_2$), 1.96(s, 3H, COCH$_3$); $^{13}$C NMR: δ 134.09–127.71(aromatic C), 117.45(=CH), 87.25(C-1), 78.18(C-5), 77.78(C-2), 75.28(C-3), 73.78(OCH$_2$), 69.16(C-4), 61.30(C-6), 37.56, 29.35 & 27.80(CH$_2$ & CH$_3$).

A mixture of compound 5.12 (1.5 g; 2.9 mmol) in acetone (50 mL) containing Jones reagent (7.0 mL) is sonicated for 2 h. Isopropanol is then added to decompose the excess of reagent. The solid is filtered off through Celite and the solid is washed with an excess of acetone. The solvent is removed under reduced pressure and the residue is dissolved in ethyl acetate and washed with aq. NaCl solution, dried over Na$_2$SO$_4$, and concentrated. The product is purified on a silica gel column using 10–15% methanol in CH$_2$Cl$_2$ as eluent to give compound 5.13 (0.8 g; 52%); $^1$H NMR (300 MHz, CD$_3$OD): δ 7.96–7.32(m, 10H, arom.), 5.98–5.85(m, 1H, allylic H), 5.49(t, J=9.6 Hz, 1H, H-4), 5.31(t, J=9.6 Hz, 1H, H-3), 5.26–5.11(m, 2H, vinylic H), 4.94(d, J=9.6 Hz, 1H, H-1), 4.34(d, J=9.6 Hz, 1H, H-5), 2.62–2.34(m, 4H, 2×COCH$_2$), 1.97(s, 3H, COCH$_3$); $^{13}$C NMR: δ 135.82 (aromatic C), 117.62(=CH), 88.26(C-1), 78.99(C-5), 76.62 (C-2), 76.40(C-3), 74.88(OCH$_2$), 71.59(C-4), 38.36, 29.49 & 28.99(CH$_2$ & CH$_3$).

A mixture of compound 5.13 (0.4 g; 0.8 mmol), 10% Pd—C (0.4 g), p-toluenesulfonic acid (0.13 g), methanol (20 mL) and water (4.0 mL) is refluxed with stirring for 16 h. The solid material is then filtered off through Celite and the filtrate is concentrated under reduced pressure. The residue is dissolved in ethyl acetate and washed with aq. NaCl solution, dried over Na$_2$SO$_4$ and concentrated. The residue is purified on a silica gel column using a solvent gradient consisting of 15–20% methanol in CH$_2$Cl$_2$ to give compound 5.14 (0.06 g; 16%); $^1$H NMR (300 MHz, CD$_3$OD): δ 7.96–7.32(m, 10H, arom.), 5.35(t, J=9.3 Hz, 1H, H-4), 5.25(t, J=9.6 Hz, 1H, H-3), 4.85(d, J=9.9 Hz, 1H, H-1), 4.29(d, J=9.6 Hz, 1H, H-5), 3.53(t, J=9.6 Hz, 1H, H-2), 2.63–2.42(m, 4H, 2×COCH$_2$), 1.97(s, 3H, COCH$_3$); $^{13}$C NMR: δ 134.47–129.04(aromatic C), 89.20(C-1), 77.29(C-5 & C-3), 71.69(C-2), 71.46(C-4), 38.56, 29.58 & 28.99 (CH$_2$ & CH$_3$). ESMS: Calcd. For C$_{24}$H$_{24}$O$_9$S (488); Found: 487[M−H]$^-$.

Example I-6

Synthesis of Phenyl 3-O-levulinoyl-4-O-benzoyl-1-thio-α-D-glucopyranosiduronic acid (compound 6.18)

Methyl 2-O-allyl-4,6-O-benzylidene-α-D-glucopyranoside (compound 6.2)

As depicted in Scheme 6, compound 6.1, methyl 4,6-O-benzylidene-α-D-glucopyranoside (100 g; 354 mmol), which is obtained from reaction of methyl α-D-glucopyranoside and benzaldehyde dimethyl acetal according to the procedure of M. E. Evans, *Carbohydr. Res.*, 21:473 (1972), and dibutyltin oxide (88.0 g, 354 mmol) in toluene (400 mL) are heated to reflux with a Dean-Stark trap overnight. The solvent is evaporated and the residue is dissolved in allyl bromide (250 mL) and heated at refluxing for 20 h. Solvent is removed and the residue is precipitated in ethyl acetate/hexane to give the product (49 g). The oil portion is purified with column chromatography to give additional product (25 g). The two portions of product are combined to give compound 6.2 (74 g; 64.5%): TLC (40% ethyl acetate in hexane): Rf 0.47. $^1$H NMR (300 MHz, CDCl$_3$): δ 7.85(m, 2H), 7.35(m, 3H), 5.95(m, 1H), 5.53(s, 1H), 5.35–5.20(m, 2H), 4.84(d, 1H, J=3.9 Hz,), 4.30–4.05 (m, 3H), 3.90–3.70(m, 2H), 3.50(t, 1H), 3.45(s, 3H), 2.58(d, 1H, J=2.1 Hz), 1.59(bs, 1H).

Compound 6.2 (45 g; 140 mmol), levulinic acid (24.5 g; 210 mmol), DCC (46 g; 224 mmol) and DMAP (1 g) in DCM (400 mL) are stirred at RT for 16 h. The reaction mixture is filtered and concentrated. The residue is re-dissolved in DCM, filtered and concentrated to give a solid product, which is re-crystallized from ethyl acetate/hexane to give product 6.4c as a white solid (50 g; 85%). TLC (50% ethyl acetate in hexane): Rf 0.53. $^1$H NMR (300 MHz, CDCl$_3$): δ 7.42–7.31(m, 5H), 5.90(m, 1H), 5.47(s, 1H), 5.35–5.20(m, 2H), 4.84(d, 1H, J=3.9 Hz,), 4.30–4.05 (m, 3H), 3.90–3.70(m, 2H), 3.50(t, 1H), 3.43(s, 3H), 2.72(m, 2H), 2.63(m, 2H), 2.16(s, 3H).

To a solution of compound 6.4c (50 g; 120 mmol) and triethylsilane (90 mL) in DCM (400 mL) at 0° C. is added dropwise TFA (48 mL) over 20 min. The reaction mixture is stirred at RT for 1 h, washed with cold saturated Na$_2$CO$_3$ solution, and dried overmgSO$_4$. The solvent is removed to give product 6.6c as an oil, which is used for the next reaction without purification. TLC (50% ethyl acetate in hexane): Rf 0.23. $^1$H NMR (300 MHz, CDCl$_3$): δ 7.34(m, 5H), 5.90(m, 1H), 5.35–5.10(m, 2H), 4.84(d, 1H, J=3.9 Hz,), 4.60(m, 2H), 4.10–4.05(m, 3H), 3.70(m, 2H), 3.50(t, 1H), 3.42(s, 3H), 2.72(m, 2H), 2.63(m, 2H), 2.18(s, 3H).

To a solution of compound 6.6c (crude product) in pyridine containing DMAP (1 g) at 0° C. is added dropwise benzoyl chloride. The reaction mixture is stirred at RT overnight. Solvent is evaporated and the residue is washed with 2M aq. HCl and saturated NaHCO$_3$ in DCM, dried, then purified with column chromatography (10–50% ethyl acetate in hexane) to give compound 6.8c as an oil (41 g; 65% based on 6.4c). TLC (50% ethyl acetate in hexane): 0.55. $^1$H NMR (300 MHz, CDCl$_3$): δ 8.0(m, 2H), 7.60–7.10 (m, 9H), 5.90(m, 1H), 5.60(t, 1H, J=9.6 Hz), 5.40–5.15(m, 3H), 4.90(d, 2H, J=3.9 Hz), 4.50(m, 2H), 4.05(m, 2H), 3.60(m, 2H), 3.48(s, 3H), 2.60–2.40(m, 4H), 2.01(s, 3H).

NaBH4 (610 mg) is added portionwise to a solution of compound 6.8c (9.7 g; 16.8 mmol) in methanol (45 mL) at 0° C. The solution is stirred at RT for 0.5 h., diluted with ethyl acetate (100 mL), washed with 2.5% aq. AcOH, and dried over Na$_2$SO$_4$. The solvent is removed and the residue is re-dissolved in ethyl acetate, dried, and evaporated to give compound 6.12 as an oil (10 g; 100%). TLC (50% ethyl acetate in hexane): Rf 0.46. $^1$H NMR (300 MHz, CDCl$_3$): δ 8.0(m, 2H), 7.60–7.10(m, 8H), 5.90(m, 1H), 5.60(m, 1H), 5.60(t, 1H), 5.40–5.15(m, 3H), 4.90(d, 2H, J=3.9 Hz), 4.50(m, 2H), 4.05(m, 2H), 3.60(m, 2H), 3.48(s, 3H), 2.35(m, 2H), 1.60(m, 2H), 0.99 (m, 3H). FAB MS: 551 (M+Na).

To a mixture of ZnI$_2$ (138 g; 432 mmol) and Bu$_4$NI (80 g; 216 mmol), which is dried at 60° C. under vacuum for 2 h, is added a solution of compound 6.12 (43 g; 72 mmol) in 1,2-dichloroethane (450 mL), followed by phenylthiotrimethylsilane (109.2 g; 114 mL; 600 mmol). The mixture is stirred at 60° C. for 6 h, cooled, diluted with DCM, washed with water, and dried. Column chromatography (5%–60% ethyl acetate in hexane) gives compound 6.14 (20 g; 54%). TLC (50% ethyl acetate in hexane): Rf 0.28. $^1$H NMR (300 MHz, CDCl$_3$): δ 8.0(m, 2H), 7.60–7.10(m, 8H), 5.90(m, 1H), 5.80(d, 0.91H, J=5.1 Hz), 5.65(t, 1H), 5.33–5.18(m, 3H), 4.75(d, 0.09H, J=7 Hz), 4.40(m, 1H), 4.25–4.05(m, 2H), 3.95(m, 1H), 3.65(bs, 2H), 2.35(m, 2H), 1.60(m, 2H), 0.99(m, 3H). FAB MS: 539 (M+Na).

Compound 6.14 (20 g; 39 mmol) and pyridinium dichromate (126 g; 335 mmol) are stirred in DMF (300 mL) at RT for 24 h, poured into H$_2$O (1.5 L), and extracted with ether (10×40 mL). The organic layer is dried and evaporated, and the residue is purified with column chromatography (50% ethyl acetate in hexane, then 5%–10% methanol in DCM) to give compound 6.16 (10 g; 48.5%). TLC (10% methanol in DCM): Rf 0.33. $^1$H NMR (300 MHz, CD$_3$OD): δ 7.86(m, 2H), 7.47–7.10(m, 9H), 5.85(m, 1H), 5.81(d, 1H, J=5.1 Hz), 5.40–5.05(m, 4H), 4.20–3.85(m, 4H), 2.54(m, 2H), 2.37(m, 2H), 1.88(s, 3H). FAB MS: 573 (M+2Na-1).

Compound 6.16 (400 mg; 0.75 mmol), Pd on carbon (10%), p-toluenesulfonic acid (100 mg) in methanol (20 mL) and water (3 mL) are heated at reflux for 20 h, filtered, concentrated and purified with a column chromatograph (5–10% methanol in DCM) to give compound 6.18 (80 mg; 22%). TLC (10% methanol in DCM): Rf 0.23. $^1$H NMR (300 MHz, CD$_3$OD): δ 7.86(m, 2H), 7.45–7.15(m, 9H), 5.69(d, 0.91H, J=5.4 Hz), 5.26(m, 2H), 4.70(m, 1H), 4.10 (m, 1H), 2.49–2.30(m, 4H), 1.85(s, 3H). FAB MS: 533 (M+2Na-1).

Other C3 Substituents for 2-O-allyl Glucopyranosides (1) To a solution of compound 6.2 (9.0 g; 28 mmol), triethylamine (19 mL), DMAP (1.1 g) in DCM (120 mL) at −15° C. is added formic acid (2.2 mL) followed by acetic anhydride (14 mL) dropwise over 0.5 h. The mixture is stirred at 0° C. for 0.5 h. Methanol (10 mL) is added and the reaction mixture is concentrated, redissolved in ethyl acetate, washed with 1 M aq. HCl and saturated Na$_2$CO$_3$, and dried. The crude product containing compound 6.4a is treated with TFA and triethylsilane in DCM to give compound 6.6a in the same manner as described above for compound 6.6c. The crude product containing compound 6.6a is dissolved in pyridine (120 mL) containing DMAP (500 mg). To this solution at 0° C. is added dropwise benzoyl chloride (5 mL). The mixture is stirred at RT overnight, concentrated, dissolved in DCM, washed with 1M aq. HCl and saturated Na$_2$CO$_3$, and dried. Column chromatography (10–30% ethyl acetate in hexane) gives compound 6.8a (9.9 g, 77% from compound 6.2). TLC (30% ethyl acetate in hexane): Rf 0.45. $^1$H NMR (300 MHz, CDCl$_3$): δ 8.05(s, 1H), 7.96(m, 2H), 7.44–7.19(m, 9H), 5.90(m, 1H), 5.60(t, 1H, J=9.6 Hz), 5.40(t, 1H, J=9.6 Hz), 5.30–5.20(m, 2H), 4.92(d, 2H, J=3.6 Hz), 4.50(m, 2H), 4.10(m, 3H), 3.60(m, 2H), 3.49(s, 3H). FAB MS: 479 (M+Na).

(2) To a solution of compound 6.2 (30 g; 93.7 mmol) in pyridine (200 mL) containing DMAP (1 g) at 0° C. is added dropwise benzoyl chloride (19.6 g; 16 mL; 140 mmol). The mixture is stirred at RT overnight, concentrated, washed with 1M aq. HCl and saturated NaHCO$_3$ in ethyl acetate, and dried. The crude product 6.4b is treated with TFA and triethylsilane in DCM to give compound 6.6b in the same manner as described above for compound 6.6c. The crude product (20 g) is treated with benzoyl chloride (9.9 g; 70.4 mmol) in pyridine (250 mL) containing DMAP (585 mg ) in the same manner as described above for compound 6.8a to give compound 6.8b (22 g, 88.4%). TLC (30% ethyl acetate in hexane): Rf 0.36. $^1$H NMR (300 MHz, CDCl$_3$): δ 8.15–7.15(m, 15H), 5.88(t, 1H, J=9.7 Hz), 5.75(m, 1H), 5.52(t, 1H, J=9.7), 5.14(m, 2H), 4.97(d, 1H, J=3.3 Hz), 4.53(m, 2H), 4.20–4.06(m, 3H), 3.78(m, 1H), 3.62(m, 1H), 3.52(s, 3H).

Methyl 2-O-benzyl-4,6-O-benzylidene-α-D-glucopyranoside (compound 6.3)

Compound 6.3 is prepared from compound 6.1 in the same manner as described above for compound 6.2 with benzyl bromide replacing allyl bromide. The benzylation reaction is carried out at 80–90° C. for 30 h. (75%). TLC (40% ethyl acetate in hexane): Rf 0.5. $^1$H NMR (300 MHz, CDCl$_3$): δ 7.50–7.33(m, 10H), 5.51(s, 1H), 4.73(dd, 2H, J=14.7, 12.0 Hz), 4.60(d, 1H, J=3.9 Hz), 4.25(m, 1H), 3.90–3.70(m, 2H), 3.50(m, 2H), 3.36(s, 1H).

Compound 6.9a, and intermediate compounds 6.5a and 6.7a, are prepared from compound 6.3 in the same manner as described above for synthesizing compound 6.8a. Compound 6.9a: TLC (30% ethyl acetate in hexane): Rf 0.5. $^1$H NMR (300 MHz, CDCl$_3$): δ 7.99(m, 3H), 7.60–7.10(m, 13H), 5.65(t, 1H, J=9.6 Hz), 5.35(t, 1H, J=9.6 Hz), 4.75–4.47(m, 6H), 4.02(m, 1H), 3.70–3.50(m, 2H), 3.43(s, 3H). FAB MS: 529 (M+Na).

Compound 6.13, and intermediate compounds 6.5b, 6.7b, 6.9b, are prepared from compound 6.3 in the same manner as described above for preparing the corresponding 2-O-allyl compounds from compound 6.2. Compound 6.13: TLC (40% ethyl acetate in hexane) Rf 0.27. $^1$H NMR (300 MHz, CDCl$_3$): δ 8.0(m, 2H), 7.60–7.10(m, 13H), 5.65(t, 1H, J=9.6 Hz), 5.30(t, 1H, J=9.6 Hz), 4.70–4.40(m, 5H), 3.70–3.50(m, 4H), 3.48(s, 3H), 2.3α5(m, 2H), 1.60(m, 2H), 0.99(m, 3H).

Compounds 6.10a, 6.10b, 6.11a, and 6.15 are prepared from compounds 6.8a, 6.8b, 6.9a, and 6.13, respectively, as described above for converting compound 6.12 to compound 6.14, i.e., in 1,2-dichloroethane at 60–65° C. Reactant equivalents, reaction times, and yields are shown in Table I hereinafter. The compounds were characterized as follows:

Compound 6.10a: TLC (20% ethyl acetate in hexane): Rf 0.11. $^1$H NMR (300 MHz, CDCl$_3$): δ 8.10(s, 1H), 8.03(m, 2H), 7.70–7.20(m, 8H), 5.90(m, 1H), 5.85(d, 0.91H, J=5.4 Hz), 5.70(t, 1H, J=9.6 Hz), 5.30–5.20(m, 3H), 4.75(d, 0.09H, J=7 Hz), 4.40(m, 2H), 4.30–3.90(m, 4H). FAB MS 539 (M+Na).

Compound 6.10b: TLC (30% ethyl acetate in hexane): Rf 0.26. $^1$H NMR (300 MHz, CDCl$_3$): δ 7.90(m, 2H), 7.55–7.20(m, 11H), 5.95–5.65(m, 3H), 5.40(t, 1H, J=9.6 Hz), 5.25–5.05(m, 2H), 4.50(m, 1H), 4.10(m, 3H), 3.70(m, 2H).

Compound 6.11a: TLC (20% ethyl acetate in hexane): Rf 0.40. $^1$H NMR (300 MHz, 30% ethyl acetate in hexane): δ 8.06–8.10(m, 3H), 7.60–7.20(m, 13H), 5.75–5.65(m, 2H), 5.22(t, 1H, J=9.6 Hz), 4.70(m, 2H), 4.40(m, 1H), 3.95(m, 1H), 3.61(m, 2H). FAB MS 517 (M+Na).

Compound 6.15: $^1$H NMR (300 MHZ, CDCl$_3$): δ 8.05(m, 2H), 7.60–7.20(m, 13H), 5.75–5.60(m, 2H), 5.08(t, 1H, J=9.6 Hz), 4.70(m, 2H), 4.40(m, 1H), 3.95(m, 1H), 3.61(m, 2H). FAB MS 589 (M+Na).

Compound 6.17 is prepared in the same manner as described above for synthesizing compound 6.16. TLC (10% methanol in DCM): Rf 0.35. $^1$H NMR (300 MHz, CD$_3$OD): 8.02 (m, 2H), 7.60–7.15 (m, 13H), 5.73 (d, J=4.5 Hz, 1H), 4.86(d, J=9 Hz), 4.64 (m, 2H), 4.20–3.85 (m, 3H), 2.54 (m, 2H), 2.37(m, 2H) 1.88(s, 3H). FAB MS: 623 (M+2Na−1).

Example I-7
Synthesis of Phenyl 2,5-di-O-acetyl-1-thio-α-D-glucofuranosiduronic acid (compound 7.3).

As shown in Scheme 7, 3,6-glucuronolactone (5.0 g; 28.4 mmol) is dissolved in acetic anhydride (30 mL) and acetic acid (20 ml+0.5 ml conc. sulfuric acid), and stirred for 3 h at RT. In 15 min the starting material is completely dissolved and in 30 min the product precipitates. The reaction mixture is chilled, and compound 7.1 (3.6 g; 40%) is filtered off. IR: 1806 cm$^{-1}$ (lactone carbonyl), 1745 cm$^{-1}$ (Ac), no absorbance in range 3000–3600 cm$^{-1}$.

Compound 7.1 (2.8 g; 9.27 mmol), thiophenol (1.53 g; 14 mmol), and BF$_3$.Et$_2$O (2.0 g; 14 mmol) are stirred in dichloromethane (30 mL) for 12 h. The reaction mixture is washed with sodium bicarbonate, brine, dried and purified on a column (EA-Hexane, 20% of EA) to give compound 7.2 (Phenyl 2,5-di-O-acetyl-1-thio-α-D-glucofuranosidurono-6,3-lactone) (1.8 g; 52%) and compound 7.3 (0.8 g, 23%), which are then eluted with 100% EA.

Compound 7.2: TLC (EA/Hex 1:1): Rf=0.55. MS: 352 (M+). $^1$H NMR (300 MHz, CDCl$_3$): δ 7.38–7.20(5H, m, arom.), 5.60(1H, s, H-5), 5.41(1H, s, H-2), 5.34(1H, d, J=4Hs, H-1), 5.20(1H, m, H-3), 5.05(1H, m, H-4), 2.05 (3H, s, AcO), 2.03(3H, s, AcO).

Compound 7.3: TLC (EA/Hex. 4:1): Rf=0.15. MS: 393 (M+Na+).

Example I-8
Synthesis of Phenyl 3-O-levulinoyl-4-C-methyl-1-thio-β-D-glucopyranosiduronic acid (compound 8.10).

TABLE 1

| Starting Material | Reaction Condition Mol. Equiv.; (h). | Product | α/β | Yield |
|---|---|---|---|---|
| 8a | Me$_3$SiSPh, 5.2; ZnI$_2$, 3; Bu$_4$NI, 1.3 (3) | 10a | 10:1 | 46% |
| 8b | Me$_3$SiSPh, 5; ZnI$_2$, 3.5; Bu$_4$NI, 1.5 (2) | 10b | 10:1 | 69% |
| 9a | Me$_3$SiSPh, 5; ZnI$_2$, 3; Bu$_4$NI, 1.5 (3) | 11a | 10:1 | 41% |
| 13 | Me$_3$SiSPh, 8.3; ZnI$_2$, 6; Bu$_4$NI, 3 (6) | 15 | 10:1 | 54% |

As shown in Scheme 8, phenyl 1-thio-β-D-galactoside (compound 4.3) (335 g; 1.23 mol) is reacted with trityl chloride (357 g; 1.28 mol) and DMAP (5 g) in anhydrous pyridine (1 L) at reflux temperature for 6 h. The reaction mixture is poured into ice-cold water (4 L) and stirred for 10 min then filtered. The precipitate is dissolved in CH$_2$Cl$_2$ (1 L), washed with water (2×1 L), dried over sodium sulfate (200 g) and the solvent is evaporated to give compound 8.1

(632.2 g; quantitative yield); $^1$H NMR (300 MHz, CDCl$_3$+2 drops D$_2$O): δ 7.62–7.15 (m, 5H, arom.), 4.52 (d, J=9.6 Hz, 1H, H-1), 3.85 (d, J=3 Hz, 1H, H-4), 3.66 (t, J=9.6 Hz, 1H, H-2), 3.52–3.45 (m, 3H, H-3, -6a and -6b) and 3.33–3.26 (m, 1H, H-5).

To a solution of compound 8.1 (350 g; 0.68 mol) in anhydrous DMF under argon are added imidazole (53.6 g; 0.8 mol) and tert-butyldimethylsilyl chloride (108 g; 0.72 mol). After stirring for 2 h at RT, the reaction mixture is poured into ice-cold water (6 L) and stirred for 15 min and filtered. The precipitate is washed with water (2×1 L), dissolved in CH$_2$Cl$_2$ (1 L), dried over sodium sulfate (200 g) and the solvent is evaporated. The oily residue is purified using flash silica gel chromatography with a solvent gradient of 5 to 10% ethyl acetate in hexane to give compound 8.2 (299.5 g; 70% yield); $^1$H NMR (300 MHz, CDCl$_3$+2 drops D$_2$O): δ 7.62–7.10 (m, 5H, arom.), 4.53 (d, J=9.6 Hz, 1H, H-1), 3.72–3.52 (m, 5H, H-2, H-3, H-4, -6a and -6b), 3.30–3.24 (m, 1H, H-5), 0.88 (s, 9H, Si—CMe$_3$), 0.12 and 0.10 (each s, 6H, SiMe$_2$).

To a solution of compound 8.2 (226.5 g; 0.36 mol) in anhydrous pyridine under argon at 5° C. are added acetic anhydride (35.63 mL; 0.375 mol) and DMAP (5 g). After stirring for 3 h between 5–10° C., the reaction mixture is poured into ice-cold water (6 L) and stirred for 15 min, then filtered. The precipitate is washed with water (2×1 L), dissolved in CH$_2$Cl$_2$ (1 L), dried over sodium sulfate (200 g) and the solvent is evaporated to give compound 8.3 (252 g; quantitative yield); $^1$H NMR (300 MHz, CDCl$_3$+2 drops D$_2$O): δ 7.60–7.10 (m, 5H, arom.), 5.16 (t, J=9.6 Hz, 1H, H-2), 4.54 (d, J=9.6 Hz, 1H, H-1), 3.75–3.50 (m, 4H, H-3, H-4, -6a and -6b), 3.28–3.20 (m, 1H, H-5), 2.10 (s, 3H, OCOCH$_3$), 0.85 (s, 9H, Si—CMe$_3$), 0.06 and 0.05 (each s, 6H, SiMe$_2$).

To a stirred mixture of pyridinium dichromate (112.9 g; 0.3 mol) and compound 8.3 (179 g; 0.267 mol) in anhydrous CH$_2$Cl$_2$ (700 mL) at 45° C. is added acetic anhydride (90 mL; 0.9 mol) dropwise. After stirring for 2 h at 45° C., the reaction mixture is poured into hexane (2 L) and stirred for 15 min. The hexane-CH$_2$Cl$_2$ layer is passed through a plug of silica (1 kg) and is further eluted with 20% CH$_2$Cl$_2$ in hexane to furnish 8.4 (125 g; 70% yield) as a white foam; $^1$H NMR (300 MHz, CDCl$_3$): δ 7.62–7.10 (m, 5H, arom.), 5.18 (t, J=9.6 Hz, 1H, H-2), 5.01 (d, J=9.6 Hz, 1H, H-3), 4.18 (d, J=9.6 Hz, 1H, H-1), 3.96–3.92 (m, 1H, H-5), 3.60–3.55 (m, 2H, H-6a and -6b), 2.14 (s, 3H, OCOCH$_3$), 0.84 (s, 9H, Si—CMe$_3$), 0.07 and 0.04 (each s, 6H, SiMe$_2$).

To a solution of compound 8.4 (103.7 g; 0.155 mol) in anhydrous toluene under argon at −78° C. are added cerium chloride (10 g) and methylmagnesium chloride in THF (207 mL; 0.621 mol; dropwise addition). The cooling bath is removed and the reaction mixture is stirred for 36 hours at RT. The reaction mixture is cooled to −10° C. (ice-salt bath) and a saturated aqueous sodium chloride solution (250 mL) is added dropwise. After filtering, the precipitate is washed with CH$_2$Cl$_2$ (2×200 mL), the filtrate is evaporated and the residue is purified on a flash silica column using eluants of 5–8% ethyl acetate in hexane to give compound 8.5 (39.16 g; 40% yield); $^1$H NMR (300 MHz, CDCl$_3$): δ 7.70–7.20 (m, 5H, arom.), 4.61 (d, J=9.6 Hz, 1H, H-1), 3.52–3.40 (m, 3H), 3.26–3.16 (m, 2H), 2.79 (s, 1H, C$_4$—OH), 2.27 (d, J=2.4 Hz, C$_2$—OH), 0.90 (s, 3H, 4-C—Me). $^{13}$C NMR (75 MHz, CDCl$_3$+2 drops D$_2$O): δ 20.7 (4-C—$\underline{C}$H$_3$), 0.85 (s, 9H, Si—CMe$_3$), 0.09 and 0.07 (each s, 6H, SiMe$_2$).

Further elution with ethyl acetate/hexane (3:1) affords C4 epimer 8.6 (21.3 g; 26%); $^1$H NMR (300 MHz, CDCl$_3$+2 drops D$_2$O): δ 7.69–7.22 (m, 5H, arom.), 4.56 (d, J=9.6 Hz, 1H, H-1), 3.65 (t, J=9.6 Hz, 1H, H-2), 3.57–3.25 (m, 3H, H-5, -6a and -6b), 3.17 (d, J=9.6 Hz, 1H, H-3), 0.95 (s, 3H, 4-C—Me). $^{13}$C NMR (75 MHz, CDCl$_3$+2 drops D$_2$O): δ 20.7 (4-C—$\underline{C}$H$_3$).

To a solution of compound 8.5 (27.4 g; 42.67 mmol) in anhydrous THF (42 mL) is added dropwise a solution of Bu$_4$NF in THF (42 mL; 1.0 M, 42 mmol). The reaction mixture is stirred for 25 min at RT, concentrated at reduced pressure, and the gummy yellow liquid obtained is purified by silica gel chromatography eluting with 15% EA/hexane to afford compound 8.7 (19 g; 70% yield) as a foamy solid; $^1$H NMR (300 MHz, CDCl$_3$): δ 7.45–7.05 (m, 20H, arom), 4.51 (d, J=9.6 Hz, 1H, H-1), 3.4–3.1 (m, 5H, H-2, H-3, H-5, H-6), 2.78 (brs, 1H, OH), 2.45 (brs, 1H, OH), 0.9 (s, 3H, 4-C—Me), 0.84 (s, 9H, Si—CMe$_3$), 0.11 and 0.05 (each s, 6H, SiMe$_2$); $^{13}$C NMR (75 MHz, CDCl$_3$): δ −4.22, 3.79, 15.23, 18.39, 26.06, 62.71, 72.89, 79.96, 81.21, 87.43, 89.62, 126.92, 127.12, 127.90, 128.52, 128.82, 130.60, 134.89, 143.46.

To a solution of levulinic acid (4 mL) in anhydrous CH$_2$Cl$_2$ (40 mL) are added DCC (8 g; 39.2 mmol) and DMAP (1.2 g) followed by addition of compound 8.7 (6.3 g; 9.8 mmol) in anhydrous CH$_2$Cl$_2$ (20 mL). After 16 h at reflux the byproduct is filtered off, and washed with CH$_2$Cl$_2$. The combined organic layers are washed with water, brine, dried over NaSO$_4$, and concentrated. The organic residue is purified using silica-gel chromatography eluting with 30% EA/hexane to afford compound 8.8 (4.75 g, 65% yield) as a foamy solid; $^1$H NMR (300 MHz, CDCl$_3$): δ 7.62–7.11 (m, 20 H, arom), 4.94 (d, J=9 Hz, 1H, H-3), 4.75 (d, J=9.3 Hz, 1H, H-1), 3.65–3.55 (m, 2H, H-2, H-5), 3.35 (d, J=5.4 Hz, 2H, H-6), 2.91–2.39 (m, 4H, lev CH$_2$'s), 2.14 (s, 3H, COCH$_3$), 1.04(s, 3H, 4-C—Me), 0.88 (s, 9H, Si—CMe$_3$), 0.22 and 0.05 (each s, 6H, SiMe$_2$); $^{13}$C NMR (75 MHz, CDCl$_3$): δ −3.84, 16.21, 18.07, 25.85, 29.70, 29.71, 38.52, 62.38, 71.05, 72.95, 81.60, 82.42, 86.92, 88.91, 126.92, 126.98, 127.77, 128.65, 128.95, 130.53, 143.81, 173.37, 207.67.

To a solution of compound 8.8 (2.5 g, 3.36 mmol) in CHCN:H$_2$O (9:1; 25 mL) is added DDQ (470 mg, 2.06 mmol) under argon and refluxed for 3 h. TLC indicates the formation of a mixture of two compounds, due to deprotection of trityl and tert-butyldimethylsilyl groups as well as deprotection of the trityl group alone. An additional amount of DDQ (470 mg) is added, and reflux is continued for 2 h. The reaction mixture is concentrated under reduced pressure, and the residue is passed through a pad of NaHCO$_3$ and then chromatographed (silica-gel) and eluted with 10% methanol/ethyl acetate to afford compound 8.9 as a dark brown colored solid (1.25 g; 91% yield); $^1$H NMR (300 MHz, CDCl$_3$): δ 7.54–7.28 (m, 5H, arom), 4.99 (d, J=9.6 Hz, 1H, H-3), 4.66 (d, J=9.6 Hz, 1H, H-1), 4.01–3.11(m, 7H, H-2, H-5, H-6, two OH), 2.75 (m, 2H, lev group CH$_2$), 2.11 (s, 3H, COCH$_3$), 1.04 (s, 3H, 4-C—CH$_3$); $^{13}$C NMR (75 MHz, CDCl$_3$); δ 13.93, 15.14, 27.93, 29.57, 37.97, 60.26, 60.53, 69.32, 69.31, 72.31, 80.85, 82.33, 87.09, 127.60, 127.74, 127.86, 128.72, 131.31, 131.70, 173.29, 208.61.

To a solution of compound 8.9 (1 g; 2.6 mmol) in acetone (10 mL) is added Jones reagent (5.5 mL; 0.7 M), the resulting mixture is sonicated for 30 mins, and then quenched with isopropanol (20 mL). The reaction mixture is filtered, concentrated and purified by silica-gel chromatography eluting with 20% MeOH-DCM to afford compound 8.10 as a foamy solid (400 mg; 40% yield); $^1$H NMR (300 MHz, CDCl$_3$): δ 7.61–7.21 (m, 5H, arom), 4.82 (d, J=9.6 Hz, 1H, H-3), 4.61 (d, J=9.6 Hz, 1H, H-1), 3.27–3.22 (m, 1H, H-5), 3.18 (t, J=9.6 Hz, 1H, H-2), 2.80–2.52 (m, 4H, lev group CH$_2$), 2.10 (s, 3H, COCH$_3$), 1.06 (s, 3H, 4-C—CH$_3$). $^{13}$C NMR (75 MHz, CDCl$_3$): δ 16.73, 29.05, 29.78, 38.73, 70.4, 81.55, 89.05, 129.08, 130.10, 132.36, 133.54, 134.35, 173.87, 208.61.

PART II. SYNTHESIS OF DONOR SACCHARIDES

Example II-1

Synthesis of Phenyl 2,3,4,6-tetra-O-pivaloyl-1-thio-D-mannopyranoside (compound 9.3).

As depicted in Scheme 9, to a stirred solution of D-mannose 9.1 (20 g; 0.11 mol) in anhydrous pyridine (150 mL) is added a catalytic amount of DMAP (200 mg). The resulting solution is cooled to 0° C. and pivaloyl chloride (109 mL; 0.88 mol) is added dropwise over 30 min. The reaction mixture is stirred at 80° C. (oil-bath) for 48 h, and then poured into 800 mL of water to obtain a gummy solid. This semi-solid mass is filtered, washed several times with water, and dissolved in methylene chloride (500 mL). The methylene chloride layer is washed with NaHCO$_3$ solution (400 mL), water, brine, and concentrated. The crude compound is crystallized from EtOH/H$_2$O to afford compound 9.2 (47.5 g; 71% yield) as a white solid, mp 118–120° C.; $^1$H NMR (300 MHz, CDCl$_3$): δ 5.83(d, J=1.2 Hz, 1H, H-1), 5.45–5.52(m, 2H, H-2 and H-4), 5.17(dd, J=10.2, 3.3 Hz, 1H, H-3), 4.15–4.25(m, 2H, H-6), 3.85 (ddd, J=10.2, 3.9, 2.1 Hz, 1H, H-5), 1.12, 1.16, 1.17, 1.24, 1.31 (5s, 45H, pivaloyl).

Treatment of compound 9.2 with thiophenol in the presence of BF$_3$-etherate at 50° C. provides the thiophenyl derivative 9.3 in 77% yield. The amount of compound 9.3 obtained is 35 g (the α-anomer is the major product). Thus, to a stirred solution of compound 9.2 (46.5 g; 0.077 mol) in anhydrous methylene chloride (150 mL) is added thiophenol (17 mL; 0.17 mol) and BF$_3$-etherate (9 mL; 0.076 mol). The reaction is allowed to stir overnight at 50° C., by which time all the starting material has been consumed (TLC analysis). The reaction mixture is diluted with methylene chloride (250 mL), washed with 10% Na$_2$CO$_3$ solution (200 mL), water, brine and dried (Na$_2$SO$_4$). The residue is purified by flash column chromatography eluting with 7% EtOAc/hexane to afford two fractions of compound 9.3 (first fraction: 35 g, 60% yield, >99% pure by NMR; second fraction: 10 g, 17%, >95% pure by NMR) as a foamy solid (mp 88–90° C.); IR (KBr): 2973, 2874, 1738, 1479 cm$^{-1}$, $^1$H NMR (300 MHz, CDCl$_3$): δ 7.2–7.6(m, 5H, ArH), 5.59–5.51(m, 2H, H-2 and H-4), 5.44(d, J=1.5 Hz, 1H, H-1), 5.33(dd, J=10.2, 3.3 Hz, H-3), 4.55–4.65(m, 1H, H-5), 4.25(dd, J=12.9, 4.8 Hz, 1H, H-6), 4.11(dd, 10.8, 1.5 Hz, 1H, H-6), 1.26, 1.21, 1.16, 1.14, 1.13 (5s, 45H, pivaloyl). $^{13}$C NMR (75 MHz, CDCl$_3$): δ 178.06, 177.12, 176.91, 176.61, 132.93, 131.98, 129.19, 129.01, 128.92, 128.86, 128.02, 86.31, 70.88, 69.97, 69.76, 65.17, 62.08, 38.90, 38.81, 38.79, 38.72, 27.08, 27.04. FAB MS: for C$_{32}$O$_9$SH$_{48}$Na 631, 499 (MH-SPh).

Example II-2

Synthesis of Phenyl 2,3,4-tri-O-acetyl-1-thio-L-fucopyranoside (compound 10.3), Phenyl-1-thio-L-fucopyranoside (compound 10.4), and Phenyl 2,3,4-tri-O-pivaloyl-1-thio-L-fucopyranoside (compound 10.5):

As shown in Scheme 10, treatment of L-fucose (compound 10.1) with acetic anhydride and pyridine provides compound 10.2, which upon treatment with thiophenol in the presence of BF$_3$-etherate affords the thiophenyl derivative 10.3.

To a stirred solution of compound 10.3 (46 g; 0.12 mol) in anhydrous methanol (200 mL) is added sodium methoxide (7.1 g; 0.13 mol), and the mixture is stirred at room temperature for 2 h. The resulting solution is neutralized with H$^+$ resin (Amberlite IR-120), filtered, washed with methanol (200 mL), and dried. The crude compound 10.4 (31 g; 0.12 mol) is dissolved in anhydrous pyridine (200 mL), and then charged with pivaloyl chloride (119 mL; 0.97 mol), followed by a catalytic amount of DMAP (200 mg). The reaction mixture is stirred at 80° C. for 48 h, poured into 800 mL of water, and then extracted with methylene chloride (2×300 mL). The methylene chloride extract is washed with water (2×300 mL), saturated NaHCO$_3$ solution (500 mL), water, brine, and dried (Na$_2$SO$_4$). The crude product is purified by flash chromatography, eluting with 10% EtOAc/hexane, to afford compound 10.5 as a colorless liquid (44 g; 72%), IR (neat): 2972, 1738, 1479 cm$^{-1}$; $^1$H NMR (300 MHz, CDCl$_3$): δ 7.51–7.56(m, 2H, ArH), 7.30–7.32(m, ArH, 3H, ArH), 5.91(d, j=4.5 Hz, 1Hα), 5.31–5.36(m, H-4α, H-3α, H-2α), 5.24(d, J=3.3 Hz, 1H, H-4β), 5.19(t, J=10.2 Hz, H-2β), 5.09(dd, J=10.2, 3.3 Hz, 1H, H-3β), 4.68(d, J=9.3 Hz, 1H, H-1β), 3.90(dd, J=12.6, 6.3 Hz, 1H, H-5β), 1.21, 1.17, 1.08 (3s, 27H, pivaloyl); $^{13}$C NMR (75 MHz, CDCl$_3$): δ 177.28, 177.26, 176.36, 133.59, 131.24, 128.66, 128.17, 85.15, 73.40, 72.61, 70.00, 66.35, 38.94, 38.64, 27.09, 26.97, 16.40; Fab for C$_{27}$O$_7$SH$_4$Na 531, 399 (MH-SPh).

Example II-3

Synthesis of Phenyl 2-phthalimido-2-deoxy-3,4,6-tri-O-acetyl-1-thio-β-D-galactopyranoside (compound 11.5).

As depicted in Scheme 11, D-Galactosamine hydrochloride (compound 11.1) (25 g; 0.116 mol) is stirred with 200 g of a wet strong basic resin in OH-form (Aldrich, Amberlite IRA-400 (OH)) to produce compound 11.2 in 300 mL of methanol and 15 mL triethylamine for 3 h at room temperature under nitrogen. The resin is filtered and washed with MeOH (200 mL). The filtrate is transferred into a 1 L three-neck flask, phthalic anhydride (18.9 g; 0.128 mol) is added with stirring, TEA (15 mL) is poured into the reaction mixture and it is stirred under nitrogen at room temperature overnight. The solvent is evaporated under vacuum at 60° C. to a residue volume in the flask of about 100 mL. It is poured dropwise with stirring in 300 ml of EA to give a solid or oil that turns to a solid while chilling in an ice bath. This solid compound 11.3 is treated with pyridine (100 mL), acetic anhydride (100 mL), DMAP (10 g) in DCM (200 mL) and refluxed for 1 h. The reaction is quenched by pouring the mixture on ice. The reaction mixture is transferred to a separatory funnel and washed with 5% HCl (200 mL), water, sodium bicarbonate, brine, and dried. The solvent is evaporated and the residue is purified on a column in EA-hexane to give compound 11.4 (17 g; 41.6 mmol; 36% yield based on compound 11.1).

Compound 11.4 (17 g; 41.6 mmol) is dissolved in 200 mL of DCM. Thiophenol (8.3 g; 10 mL; 74.9 mmol) and BF$_3$-etherate (18 mL) are added and the reaction mixture is stirred at room temperature for 18 h, then it is refluxed for 1 h, chilled to room temperature, transferred into a separatory funnel and washed with sodium carbonate (3×300 ml), brine, and dried. The solvent is evaporated, the residue is dissolved in EA-hexane 20 ml (2:1), and is purified on a column to give 13 g of compound 11.5, as white or slightly yellow crystals, mp 91° C. Yield 86%. TLC (1:1 Ethyl acetate/Hexane): R$_f$=0.55. $^1$H NMR (300 MHz, CDCl$_3$): δ 7.2–7.9(9H, m, arom), 5.85(1H, dd, H-3), 5.72(1H, d, J=8 Hz, H-1), 5.50(1H, d, H-4), 4.63(1H, t, H-2), 4.05–4.25(3H, m, H-5+H$_2$-6). IR, neat, ν: 1746, 1722, 1379, 1229, 1073, 912, 726 cm$^{-1}$. FAB MS: m/z, 550 (M+Na$^+$). Anal. Calc. for C$_{26}$H$_{25}$NO$_9$S: C, 59.20; H, 4.74; N, 2.65; S, 6.07. Found: C, 59.83; H, 5.01; N, 2.59; S, 6.22.

Example II-4
Synthesis of Phenyl 2-azido-2-deoxy-3,4-di-O-acetyl-1-thio-D-fucopyranoside (compound 12.8).

As shown in Scheme 12, D-Fucose (compound 12.1) (25 g; 0.152 mol) is dissolved in pyridine (500 mL), chilled in an ice-water bath and acetic anhydride (125 mL) is added. The reaction mixture is kept at room temperature 18 h. Pyridine and excess of acetic anhydride are evaporated (100 mm Hg, 75° C.). The oily residue is dissolved in dichloromethane (300 mL) and washed with dilute HCl (5%, 200 mL), a saturated solution of sodium bicarbonate (200 mL×2), brine, then dried and evaporated to give compound 12.2 (48 g; 98% yield) as a thick oil. Rf is 0.4 in EA-Hex, 1:1.

Compound 12.2 (42.0 g; 0.126 mol) is dissolved in 110 mL of a AcOH-Ac$_2$O mixture (77 mL+33 mL), chilled in ice-water bath and then 140 mL of the 30% HBr in AcOH is added dropwise. The reaction mixture is kept in an ice bath for 1 hour and after 2 hours at room temperature EA (600 mL) is added. The reaction mixture is transferred to a separatory funnel, washed with ice-water (2×500 mL), sodium bicarbonate, brine, dried over sodium sulfate and then decanted to a 2-neck flask equipped with mechanical stirrer. This EA solution contains compound 12.3 in about 90% purity.

Activated Zn (85 g) and N-methylimidazole (13 mL) are added to the EA solution of compound 12.3 at room temperature. The reaction mixture is heated to reflux over 20 min and is stirred very vigorously over 30 min at reflux, chilled to room temperature, filtered through Celite, and the filter cake is washed with EA. The filtrate is washed with 2% sulfuric acid (200 mL×2), sodium bicarbonate (300 mL), brine (100 mL), dried and evaporated at +70° C. to give diacetyl fucal compound 12.4 as a thick oil (19 g; 71% yield). After 1–3 days the oil turns to crystalline product, mp 47° C. TLC (1:1 Ethylacetate/Hexane): Rf=0.50. $^1$H NMR (300 MHz, CDCl$_3$): δ 6.35(1H, d, H-1), 5.48(1H, dd, H-4), 5.18(1H, dd, H-3), 4.55(1H, m, H-5), 4.12(1H, m, H-2), 2.05(3H, s, Ac), 1.92(3H, s, Ac), 1.18(3H, d, H$_3$-6). FAB MS m/z, 215 (M+H$^+$).

Compound 12.4 (19 g; 89 mmol) is dissolved in acetone (500 mL), chilled to −16° C., then (NH$_4$)$_2$Ce(NO$_3$)$_6$ (100 g; 0.182 mol) is added. Sodium azide (10 g, 0.15 mol) is added to the suspension at −15–18° C., kept at this temperature 8 hours with good mechanical stirring. The reaction mixture is transferred to a separatory funnel containing 750 mL of water and 500 mL of ether. The water phase is extracted with ether one more time. The organic layer is separated, washed with water (4×300 mL), brine, dried and evaporated to give a thick oil (22.7 g; 85% yield). The oil is a mixture of compound 12.5 (70%) and compound 12.6 (30%). The Rf is 0.6 and 0.2, respectively (EA/Hex 1:1).

The oil is dissolved in AcOH (110 mL+2 mL of conc. H$_2$SO$_4$) and Ac$_2$O is added at +4° C. The reaction mixture is kept at 36–38° C. for 2 h, then neutralized with sodium acetate (6.5 g). The mixture is transferred into a separatory funnel with dichloromethane (400 mL) and water (500 mL). The water extraction is repeated, then the organic layer is extracted with sodium bicarbonate (2×300 mL), brine, dried, and evaporated to dryness to give a thick oil. Upon chilling and scratching the oil turns to a crystalline product, which is washed with cold ether (10 mL) and dried to give compound 12.7 (17.5 g; 62% yield relative to compound 12.4), mp 156° C. TLC (EA:Hexane 1:1): Rf=0.4. IR, neat 2116, 1753, 1372, 1220. Anal. Calc. for C$_{12}$H$_{17}$N$_3$O$_7$. C, 45.7; H, 5.39; N, 13.33. Found: C, 45.63; H, 5.38; N, 13.25.

Compound 12.7 (17.5 g; 55.7 mmol), thiophenol (6.13 g; 111.4 mmol) and BF$_3$.Et$_2$O (7.8 g; 6.8 mL; 55 mmol) are mixed in DCM (200 mL) and stirred overnight at room temperature. The reaction mixture is washed with sodium carbonate (200 mL), water, brine, dried, and evaporated at +70° C. The oily residue is purified on a column in EA-Hexane system and the product is eluted at 20% of EA. The appropriate fractions after evaporation afford compound 12.8 (18.1 g; 89% yield), which consists of the α- and β-isomers in ratio 2:1. The β-isomer is crystalline at room temperature and is isolated by recrystallization from ether, mp 55° C. The α-isomer is isolated with 90% purity as a liquid. TLC (1:1 Ethyl acetate/Hexane): Rf=0.6. $^1$H NMR (300 MHz, CDCl$_3$): δ 7.28–7.65(5H, m, arom.), 5.62(1H, d, J=3 Hz, H-1, α), 5.32(1H, d, H-4, β), 5.20(1H, m, H-3), 5.15(1H, d, H-4, α), 4.85(1H, dd, H-2, β), 4.61(1H, q, H-5, α), 4.49(1H, d, J=9 Hz, H-1, β), 4.28(1H, dd, H-2α), 3.78(1H, q, H-5, β). FAB MS m/z: 383 (M+NH$_4^+$). Anal. Calc. for C$_{16}$H$_{19}$N$_3$O$_5$S: C, 52.60; H, 5.20; N, 11.51; S, 8.76. Found: C, 52.58; H, 5.24; N, 11.40; S, 8.80.

Example II-5
Synthesis of Phenyl 2-azido-2-deoxy-3,4,-di-O-acetyl-1-thio-L-fucopyranoside (compound 13.7), Phenyl 2-azido-2-deoxy-1-thio-L-fucopyranoside (compound 13.8), and Phenyl 2-azido-2-deoxy-3,4-carbonate-1-thio-L-fucopyranoside (compound 13.9).

As depicted in Scheme 13, L-Fucose (25 g; 152 mmol) is dissolved in pyridine (300 mL) and acetic anhydride (100 mL) is added. The reaction mixture is stirred at room temperature for 24 h and then evaporated at +65° C. to afford 55 g of compound 13.1 as a thick colorless oil. Compound 13.1 (45 g crude or 41 g pure; 123 mmol) is dissolved in a mixture of 74 mL of AcOH and 30 ml of Ac$_2$O at room temperature, chilled to 0° C., and 130 ml of 30% HBr in AcOH is added dropwise while chilling. The reaction mixture is kept 1 h at 0° C. and then 3 h at room temperature, poured into a separatory funnel with water-ice (1 L) and EA (0.5 L), washed with water three times, then with a saturated solution of NaHCO$_3$ (3×300 mL), brine, and dried. This solution contains bromide derivative 13.2, which does not need to be isolated. To this solution in a 2-neck 1 L flask, activated Zn (78 g) and N-methyl-imidazole (11.5 mL) are added, and the mixture is heated under reflux with vigorous mechanical stirring for 1 h, and chilled to room temperature. The Zn is filtered through Celite and the filtrate is washed with water, NaHCO$_3$, brine, dried, and evaporated to give an oil. The weight of the crude product is 24 g (93%). After flash chromatography purification the 3,4-O-diacetyl-L-fucal compound 13.3 is isolated (13.4 g; 52% yield based on L-fucose), mp 46° C.

Compound 13.3 (13.4 g; 62.6 mmol), (NH$_4$)$_2$Ce(NO$_3$)$_6$ (67 g; 122 mmol) and sodium azide (7.0 g; 107 mmol) are mixed in 350 mL of dry acetone at −16° C. With very vigorous stirring, the reaction mixture is kept for 8 h at −16° C., poured into a separatory funnel with ice-water (1 L) and ether (0.5 L), washed with NaHCO$_3$, brine, dried, and evaporated to an oily residue. The product of the reaction is a mixture of compound 13.4 (Rf 0.3) and compound 13.5 (Rf 0.65, EA-Hex 2:8). The IR spectrum shows signals of the azido group (2116 cm$^{-1}$) and carbonyl (1750 cm$^{-1}$).

The oily mixture of compounds 13.4 and 13.5 (16.8 g) is dissolved in 80 mL of Ac$_2$O and 80 mL of 2% (vol.) sulfuric acid in AcOH at room temperature and kept for 2 h at +37° C., neutralized with sodium acetate (6.0 g) with chilling, and poured into dichloromethane—water (300mL–1.0 L). The organic layer is washed with NaHCO$_3$, brine, dried, and is evaporated to dryness. Chilled ether (10 mL) is added to the residue to give a white crystalline precipitate of compound 13.6 (10.8 g; 55% yield based on fucal 13.3), which is the α-isomer, mp 159° C. The ether soluble fraction is the β-isomer (5.1 g), which is an oil. Total yield is 70% based on fucal 13.3. TLC shows the two isomers have the same Rf 0.30.

Compound 13.6 (15.9 g; 50.4 mmol), thiophenol (11.1 g; 100 mmol) and $BF_3.Et_2O$ (6.7 mL) are mixed in DCM (200 mL) and stirred at reflux 2.5 hours, chilled and poured into 2 L separatory funnel, washed with $NaHCO_3$ (3×300 mL), brine, dried, and evaporated to a thick oily residue. Purification by flash column chromatography in a EA-hexane system affords compound 13.7 (16.7 g; 91%) as a mixture of the α- and β-isomers in a ratio 2.5:1.0. TLC Rf=0.45 (20% ethyl acetate, 80% hexane). FAB MS: found 388 (M+Na$^+$). Anal. Calc.: C, 52.60; H, 5.2; N, 11.51; S, 8.76. $C_{16}H_{19}N_3O_5S$: Found: C, 52.67; H, 5.26; N, 11.45; S, 8.65. $^1$H NMR (300 MHz, CDCl$_3$): δ 1.13(d, 3H), 2.06(s, 3H), 2.18(s, 3H), 4.20(q, 1H, H-5, β-isomer), 4.29(dd, 1H, H-2), 4.5(d, 1H, H-1, β-isomer), 4.62(q, 1H, H-5, α-isomer), 5.15–5.2(dd, 1H, H-4), 5.63(dd, 1H, H-3), 5.64(d, 1H, H-1, α-isomer), 7.3–7.6 (m, 5H, arom.)

To a solution of compound 13.7 (4.8 g; 13.1 mmol) in 120 mL of MeOH is added potassium carbonate (6.0 g; 36.2 mmol). The reaction mixture is stirred for 1.0 h at room temperature, filtered, the filtrate is acidified with AcOH to pH 6–7, and is concentrated to dryness. The crystalline residue is treated with 50 ml DCM and purified by flash chromatography in 5% MeOH-DCM. The starting material in EA-Hex (2:8) has R$_f$ 0.50 and the product (compound 13.8) has Rf 0.05. In 5% MeOH-DCM compound 13.8 has Rf 0.55. The appropriate fractions give compound 13.8 (3.3 g; 89%), m.p. 119–121° C. MS found 304 (M+Na$^+$).

Compound 13.8 (3.3 g; 11.7 mmol) and 1,1'-carbonylimidazole (3.8 g; 23.4 mmol) are dissolved in DCM (120 mL) at 0° C., kept for 15 min, and 15 min at room temperature, washed with water (2×200 mL), brine, and purified on a flash chromatography column in EA-Hexane. Three fractions of product (compound 13.9) are collected. The first at Rf 0.35 is the α-isomer (1.8 g; 5.9 mmol; 50%), the second at Rf 0.15 is the β-isomer (0.4 g; 1.3 mmol; 12%), and a mixed two isomer fraction (0.28 g; 0.9 mmol; 8%), total 2.48 g (70%). All fractions are a colorless thick oil. α-isomer, $^1$H NMR (300 MHz, CDCl$_3$): δ 1.36(3H, d, CH$_3$), 4.28(1H, t, H-2), 4.46(1H, q, H-5), 4.65(1H, dd, H-3), 4.89(1H, dd, H-4), 5.635(1H, dd, J=5.4 Hz, α H-1), 7.30–7.50 (5H, m, arom.). IR, neat, ν: 2114, 1813 cm$^{-1}$. βisomer: $^1$H NMR (300 MHz, CDCl$_3$): δ 1.43(d., 3H, CH3), 3.50(d.d., 1H, H-2), 3.84(q., 1H, H-5), 4.44(d., 1H., J=9.9 Hz, β-1-H), 4.53(d.d., 1H, H-4), 4.60(t., 1H, H-3), 7.35–7.48 (m., 5H, arom.). IR, neat: 2116(N3), 1805(C=O).

Example II-6
Synthesis of Phenyl 2-phthalimido-2-deoxy-3,4-di-O-acetyl-1-thio-β-D-fucopyranoside (compound 14.5).

As shown in Scheme 14, 1,3,4-tri-O-acetyl-2-azido-2-deoxy-D-Fucose (compound 14.1) (3.0 g; 9.5 mmol), which is prepared as described for compound 12.7, is dissolved in acetone (50 mL), and half a teaspoon of Pd/C catalyst (under nitrogen) is added. Then 3 mL of ether and saturated HCl are added and the reaction mixture is reduced with hydrogen (40 psi) for 2 h. The catalyst is filtered and washed with MeOH. The filtrate is evaporated, dissolved in 10 ml of MeOH and compound 14.2 (1.85 g; 60% yield) is precipitated with ether (20 mL). Anal. $C_{12}H_{19}NO_7.HCl$, Calc.: C, 44.2; H, 6.14; N, 4.30; CL, 10.91. Found: C, 43.97; H, 6.08; N, 4,25; CL, 11.04%.

Compound 14.2 (1.1 g; 3.38 mmol) is dissolved in MeOH (10 mL). An ion-exchange resin in OH-form (Amberlite IRA-400, 2 g) is added and the reaction mixture is stirred at room temperature for 2 h. The Rf of the base of compound 14.2 is 0.9 (EA-Hex, 1:1). The TEA (0.5 mL) is dropped to the reaction mixture, stirred for 15 min, filtered, and washed with MeOH. The filtrate is treated with phthalic anhydride (0.6 g; 4 mmol) with stirring at room temperature for 1 h to give compound 14.3, which is not isolated (Rf 0.05).

The solvent is evaporated (70° C., 120 mmHg) to give a solid semi-crystalline mass, which is treated with Ac$_2$O (8 mL) and pyridine (5 mL) for 1 h at 100° C. in a water bath to give compound 14.4, which is separated from the reaction mixture using column chromatography. The chromatography column hydrolyzes some of the product to give some compound 14.5. The compound 14.5 is reacetylated with acetic anhydride in pyridine to produce compound 14.4.

The solution containing compound 14.4 is evaporated under vacuum (120 mmHg, 80° C.). A crystalline residue is azeotroped with toluene and is dissolved in dichloromethane (30 mL) and treated with thiophenol (1.0 mL) and $BF_3.Et_2O$ (2 mL) for 1 h at reflux. The TLC of the reaction mixture shows a presence of the target product compound 14.6 (Rf 0.65). The solvent is evaporated and the residue is purified by flash-chromatography column in a EA-Hexane isocratic (30% of EA) system. The appropriate fractions are combined and evaporated to give compound 14.6 (0.55 g; 35% yield) as a crystalline yellowish powder. After washing with MeOH, the product turns to white crystals, mp 193° C. Rf 0.2 (EA-Hex 2:8); MS 492 (M+Na$^+$). $^1$H NMR (300 MHz, CDCl$_3$): δ 7.2–7.8(m, 9H, arom.), 5.75(1H, dd, H-2), 5.60(d, J 9 Hz, H-1, β-anomeric substituent), 5.25(1H, m, H-3), 4.58(1H, tr, H-4), 3.96(1H, q, H-5). Analysis: Calc.: C, 61.40; H, 4.90; N, 2.99; S, 6.82. $C_{24}H_{23}NSO_7$. Found: C, 61.28; H, 4.93; N, 2.95; S, 6.83%.

Example II-7
Synthesis of Phenyl 2-azido-2-deoxy-hexa-O-acetyl-1-thio-β-D-gentiobiopyranoside (compound 15.7).

As depicted in Scheme 15, gentiobiose (3.0 g; 8.77 mmol) is stirred overnight at room temperature in a mixture of pyridine (60 mL) and Ac$_2$O (36 mL). The pyridine and excess of acetic anhydride are evaporated at 70° C. to give a crystalline residue of compound 15.1 (6.0 g; 100%). Crystallization of 0.2 g of compound 15.1 from EA (5 mL) gives fine crystals, m.p. 188° C. MS found 701(M+Na$^+$).

Compound 15.1 is dissolved in a mixture of AcOH (12 mL), Ac$_2$O (9 mL) and a 30% solution of HBr in AcOH (20 mL) at 0° C., and is stirred 16 h at room temperature. The reaction mixture is poured into a separatory flask containing cold water (300 mL) and EA (200 mL). The organic phase is separated, washed with water (200 mL), aqueous NaHCO$_3$ (200 mL), and brine (200 mL), and is dried over sodium sulfate to give compound 15.2.

Activated Zn dust (10 g) and N-methylimidazole (1.5 mL) are added to the EA solution containing compound 15.2 and refluxed for 40 min. The reaction mixture is chilled to room temperature, decanted and the organic phase is washed with water, NaHCO$_3$, and brine, and is dried over Na$_2$SO$_4$ and evaporated to give compound 15.3 (4.6 g; 94%) as an oil. The product should be purified by flash-chromatography in EA-Hexane system. Total amount of fractions is 50, the fractions 37–50 were combined to a weight of 3.3 g (67%), mp 94° C. MS found 583 (560+Na$^+$).

Compound 15.3 (4.0 g; 7.14 mmol) is dissolved in dry acetone (100 mL), and ammonium cerium (IV) nitrate (7.8 g; 14.3 mmol) and sodium azide (0.8 g; 12.1 mmol) are added. The reaction mixture is stirred mechanically at −15 to −20° C. for 6 h and is treated with 40% aq. EA (500 mL), NaHCO$_3$, brine, dried and evaporated to give the oily residue of compounds 15.4 and 15.5 in the ratio 4:1 (4.2 g, about 95%).

The oil is hydrolyzed in a mixture of $Ac_2O$ (20 mL) and 20 mL of 2% $H_2SO_4$ for 2 h at 37° C. The sulfuric acid in the mixture is neutralized by addition of sodium acetate (1.5 g). The neutralized solution is poured into DCM-water, washed with sodium bicarbonate, brine, dried and evaporated to give a semi-crystalline compound 15.6 (2.2 g; 45% yield). The IR spectrum contains peaks of azido group (2115 $cm^{-1}$) and carbonyl groups (1752 $cm^{-1}$), with no peaks for OH groups (3000–3600 $cm^{-1}$).

Compound 15.6 (2.2 g; 3.3 mmol) is dissolved in 20 ml of DCM and thiophenol (0.76 g; 0.68 mL; 6.6 mmol) and $BF_3.Et_2O$ (3.5 mL) are added. The reaction mixture is stirred at room temperature for 18 h. The mixture is brown and is poured into a separatory funnel and washed with water, sodium bicarbonate, brine. The organic phase is dried and evaporated to give a brown oil. The oil is dissolved in EA-Hexane (20 mL, 1:1) and is purified on a column to give compound 15.7 (1.4 g; 61% yield). TLC (EA-Hexane 1:1), Rf=0.4. MS found 734 $(M+Na^+)$. $^1H$ NMR (300 MHz, $CDCl_3$): δ 7.2–7.4(5H, m, arom.), 5.40(1H, d, H'-1), 5.05 (1H, d, H-1), 5.3(1H, m, H-3), 5.1(1H, m, H'3), 4.95(1H, m, H-4), 4.5(1H, q, H'-4), 4.0–4.28(3H, m, H-6, H-6'), 3.8(1H, t, H-5), 3.6(1H, t, H'-5). IR, neat: 2110, 1750, 1370, 1228, 1042, 735 $cm^{-1}$. Compound 15.7 exists as a mixture of α and β-isomers. This mixture is separated by flash chromatography in EA-Hexane (20% EA, 80% Hexane). From 500 mg of the mixture, 350 mg of the α-isomer (Rf 0.30, m.p. 76–78° C.) and 50 mg of β-isomer (Rf 0.35, m.p. 69–70° C.) are obtained.

Example II-8

Synthesis of Phenyl 6-O-(2,3,4,6-tetra-O-acetyl-β-D-glucopyranosyl)-(1→6)-2-phthalimido-2-deoxy-3,4-di-O-acetyl-1-thio-β-D-glucopyranoside (compound 16.9) and Intermediate 2-N-phthalimido Donor Monosaccharides.

As depicted in Scheme 16, D-Glucosamine.HCl (compound 16.1) (60 g; 0.27 mol) is added to a solution of NaOMe in MeOH [prepared from Na (6.3 g; 0.27 mol) and MeOH (270 mL)] at room temperature with stirring. The mixture is stirred for 20 min. and filtered. Phthalic anhydride (19.8 g; 1.3 mmol) and triethylamine (38.6 mL) are added to the filtrate and stirred for 30 min., then another batch of phthalic anhydride (21.6 g; 1.4 mmol) is added. A mass of solid is separated out. Ether is added to the reaction mixture and the solid is filtered off and treated with pyridine (350 mL) and acetic anhydride (200 mL) for 16 h. The product is evaporated under reduced pressure. The residue is dissolved in $CH_2Cl_2$ and washed with aq. $NaHCO_3$ solution, dried over $Na_2SO_4$ and evaporated under reduced pressure. It is purified on silica gel by using hexane-ethyl acetate (1:1→2:3, v/v) as an eluent to give compound 16.2 (69 g; 52%).

Compound 16.2 (67 g; 140.5 mmol) is reacted with $BF_3$.etherate (34.6 mL; 281 mmol) and thiophenol (28.8 mL; 282.3 mmol) in $CH_2Cl_2$ (500 mL) at room temperature for 16 h. The reaction mixture is washed with aq. $NaHCO_3$ solution and dried over $Na_2SO_4$, filtered, and solvent is removed under reduced pressure. Addition of ether to the residue gives compound 16.3 as an amorphous solid (57.1 g; 77%); $^1H$ NMR (300 MHz, $CDCl_3$): δ 7.86–7.24(m, 9H, arom.), 5.77(dd, J=9.3 Hz, 1H, H-4), 5.70(d, J=10.5 Hz, 1H, H-1), 5.12(dd, J=9.3 Hz, 1H, H-3), 4.33(dd, J=10.5 Hz, 1H, H-2), 2.07, 2.00, 1.81(each s, 9H, 3×OAc).

De-O-acetylation of compound 16.3 (4.5 g) with MeOH-MeONa for 4 h gives compound 16.4 (2.5 g; 73%); $^1H$ NMR (300 MHz, $CD_3OD$): δ 7.98–7.19(m, 9H,arom.), 5.58(d, J=10.5 Hz, 1-H, H-1), 4.27(dd, 1H, H-4), 4.16(dd, 1H, H-3).

To an ice cooled, stirred solution of compound 16.4 (2.4 g; 6 mmol) and imidazole(1.02 g; 15 mmol) in dry DMF (25 mL) is added tert-butyldimethylsilyl chloride (1.1 g; 7.3 mmol) and stirring is continued for 1 h at 0° C. The reaction mixture is poured into an ice-water mixture and the resulting solid is filtered and washed with hexane to give compound 16.5 (3.0 g; 97%); $^1H$ NMR (300 MHz, $CDCl_3$): δ 7.86–7.24 (m, 9H, arom.), 5.64(d, J=10.5 Hz, 1-H, H-1), 4.36(dd, J=8.1 Hz, 1-H, H-4), 4.20(dd, 1-H, H-2), 0.93(s, 9H, $CMe_3$), 0.13 & 0.12(each s, 6H, $SiMe_2$).

Compound 16.5 (3.2 g) is dissolved in pyridine-acetic anhydride (2:1; 75 mL) and stirred for 16 h at room temperature. The solvents are removed under reduced pressure and the residue is dissolved in $CH_2Cl_2$ and washed with aq. $NaHCO_3$ solution, water, dried and concentrated in vacuo to give compound 16.6 (3.4 g; 91%) as an amorphous solid from ether-hexane; $^1H$ NMR (300 MHz, $CDCl_3$): δ 7.88–7.25(m, 9H, arom.), 5.80(dd, J=9.3 Hz, 1H, H-4), 5.72(d, J=10.5 Hz, 1 H, H-1), 5.18(dd, 1H, H-3), 4.33(dd, J=10.5 Hz, 1H, H-2), 2.02 & 1.84(each s, 6H, 2×OAc), 0.92(s, 9H, $CMe_3$), 0.099 & 0.064(each s, 6H, $SiMe_2$).

To a solution of compound 16.6 (3.0 g; 5 mmol) in $CH_2Cl_2$ (50 mL) is added $BF_3$.etherate (0.75 mL; 6.1 mmol) and stirring is continued at room temperature for 1 h. The organic layer is washed with aq. $NaHCO_3$ solution, dried over $Na_2SO_4$ and concentrated in vacuo. This residue from ether gives compound 16.7 (2.4 g; 99%) as a white solid compound; $^1H$ NMR (300 MHz, $CDCl_3$): δ 7.89–7.27(m, 9H, arom.), 5.84(dd, J=9.3 Hz, 1H, H-4), 5.76(d, J=10.5 Hz, 1H, H-1), 5.10(dd, J=9.3 Hz, 1H, H-3), 4.35(dd, J=10.5 Hz, 1H, H-2), 2.05 & 1.85(each s, 6H, 2×OAc); $^{13}C$ NMR: δ 133.11–123.68(aromatic C), 82.95(C-1), 78.26(C-5), 71.43 (C-3), 68.99(C-4), 61.56(C-6), 53.69(C-2), 20.64 & 20.40 ($COCH_3$).

A solution of compound 16.7(0.5 g; 1.03 mmol) and acetobromoglucose (compound 16.8) (0.62 g; 1.5 mmol), obtained from Sigma Chemical Co. (St. Louis, Mo.), in 3:2 (v/v) $CH_2Cl_2$-toluene (25 mL) is stirred for 0.5 h with 4A° molecular sieves (3 g) under protection of light and moisture. Then, silver triflate (0.4 g; 1.5 mmol) and 2,6-di-tert-butyl-4-methyl pyridine (0.15 g; 0.73 mmol) is added to the reaction mixture at −20° C. The reaction mixture is warmed to −10° C. and stirred at the same temperature for 1.5 h. The saturated aq. $NaHCO_3$ solution is added to reaction mixture and filtered through Celite. The filtrate is washed with aq. $NaHCO_3$, water, dried over $Na_2SO_4$, and concentrated to a small volume. The concentrate is applied to a column of silica gel and elution is performed with hexane-ethyl acetate (1:1→1:4; v/v) to give compound 16.9 (0.55 g; 65%) as an amorphous solid. $^1H$ NMR (300 MHz, $CDCl_3$): δ 7.86(m, 9H, arom.), 5.76(dd, J=9.3 Hz, 1H, H-4), 5.70(d, J=10.5 Hz, 1H, H-1), 5.18–4.91(m, 4H, H-3, H-4', H-3', H-2', 4.57(d, J=8.1 Hz, 1H, H-1'), 2.09, 2.02, 2.01, 1.99, 1.97 & 1.81(each s, 18H, 6×OAc); $^{13}C$ NMR: δ [GlcNPhth residue] 132.69–123.65(aromatic C), 82.93(C-1), 77.63(C-5), 71.43 (C-3), 68.27(C-6), 68.19(C-4), 53.53(C-2); [Glc residue]: 100.56(C-1), 72.78(C-3), 71.81(C-2), 69.23(C-5), 68.19(C-4), 61.72(C-6). FAB MS: calcd. For $C_{38}H_{41}NO_{17}S$(815): m/z 838$[M+Na]^+$.

Example II-9

Synthesis of Phenyl 2,3,6-tri-O-pivaloyl-4-O-(tetra-O-pivaloyl-β-D-glucopyranosyl)-1-thio-β-D-glucopyranoside (compound 17.4).

As shown in Scheme 17, Octa-O-acetyl-D-cellobiose (compound 17.1) (58 g; 85.5 mmol), is dissolved in thiophenol (10 mL; 97.3 mmol) and $CH_2Cl_2$(180 mL). The system is cooled to 0° C., and $BF_3.OEt_2$ (25 mL; 198 mmol) is added dropwise. The reaction mixture is stirred at room temperature for 18 hours, then cooled to 0° C., and more thiophenol (5 mL; 48.7 mmol) and $BF_3.OEt_2$ (5 mL; 39 mmol) are added. The solution is stirred at room temperature for 66 hours more and poured into aqueous saturated $NaHCO_3$ solution (500 mL). The organic phase is washed with a saturated $NaHCO_3$ solution (1×250 mL) and brine (1×250 mL), dried over anhydrous $Na_2SO_4$ and concentrated to yield a yellowish solid. The solid is powdered, treated with boiling hexane (500 mL) and filtered. The solid consists of nearly pure compound 17.2 (58.1 g; 79.7 mmol; 93.3% yield). $^1H$ NMR (300 MHz, $CDCl_3$): δ 7.49–7.33(m; 2H), 7.31–7.25(m; 3H), 5.21–5.02(m; 3H), 4.94–4.87(m; 2H), 4.65(d; J=10.5 Hz; 1H), 4.55(dd; J=1.8 Hz, 12.0 Hz; 1H), 4.48(d; J=8.1 Hz; 1H), 4.37(dd; J=4.5 Hz, 12.6 Hz; 1H), 4.12–3.99(m; 2H), 3.75–3.60(m; 3H), 2.11(s; 3H), 2.09(s; 3H), 2.08(s; 3H); 2.02(s, 3H); 2.00(s; 3H), 1.98(s; 3H). $^{13}C$ NMR (75.4 MHz, $CDCl_3$): δ 179.04, 178.81, 178.35, 178.13, 177.91, 177.63, 141.67, 140.35, 137.50, 136.93, 109.36, 94.11, 85.35, 84.96, 82.19, 81.52, 80.58, 80.19, 78.76, 76.35, 70.61, 70.13, 29.44–29.15 (br). TLC $R_f$=0.64 (60% ethyl acetate-hexane). FAB MS: for $C_{32}H_{40}SO_{17}$ [MNa] calcd m/z 751, found m/z 751.

Compound 17.2 is dissolved in MeOH (800 mL) and THF (600 mL). The yellowish solution is cooled to 0° C., and NaOMe (3.0 g; 55.6 mmol) is added under stirring. The reaction mixture is allowed to reach room temperature over a 90 min period, then more NaOMe (0.3 g; 5.6 mmol) is added. After 3 hours of reaction, acidic resin (Dowex 500w8 200 resin, previously washed with water and methanol) is added until a pH 7 is obtained. The resin is filtered and the solution is concentrated under vacuum. Compound 17.3 is isolated as a light yellow solid in nearly quantitative yield and used in the next step without further purification. $^1H$ NMR (300 MHz, $CD_3OD$): δ 7.57–7.54(m; 2H), 7.32–7.25 (m; 3H), 4.61(d; J=9.6 Hz; 1H), 4.41(d; J=7.8 Hz; 1H), 3.86(m; 2H), 3.64(dd; J=5.4 Hz, 12.0 Hz; 1H), 3.55(t; J=7.2 Hz; 1H), 3.45–3.19(m; 8H). $^{13}C$ NMR (75.4 MHz, $CD_3OD$): δ 142.15, 140.19, 137.16, 135.71, 111.71, 96.35, 87.73, 87.42, 85.32, 85.17, 85.05, 82.12, 80.76, 78.60, 69.69, 69.19. TLC $R_f$=0.54 (30% methanol-methylene chloride). FAB MS: for $C_{18}H_{26}SO_{10}$ [MNa] calcd m/z 457, found m/z 457.

Compound 17.3 is azeotroped twice with toluene, dissolved in dry pyridine (150 mL; 1.86 mol), and DMAP (2.0 g; 16.4 mmol) and pivaloyl chloride (140 mL; 1.14 mol) are added. The reaction mixture is heated at 80° C. for 48 hours. The reaction mixture is poured into aqueous saturated $NaHCO_3$ solution (500 mL) and agitated for 30 minutes. $CH_2Cl_2$ (250 mL) is added and the organic phase is separated. The aqueous phase is back-extracted with $CH_2Cl_2$ (100 mL), and the combined organic layers are concentrated to dryness. The dark brown residue is dissolved in $CH_2Cl_2$ (250 mL), washed with HCl 2N (1×250 mL), saturated $NaHCO_3$ solution (1×250 mL) and brine (1×100 mL), dried over anhydrous $Na_2SO_4$ and concentrated to an oily residue. The crude product is loaded on a silica gel plug (1.2 L) and eluted with a gradient of 0% to 10% ethyl acetate-hexane. Fractions containing the product (as judged by TLC) are combined and concentrated. The residue (90 g) is immobilized onto silica gel 60 (160 g) and purified by flash chromatography using a gradient of 0% to 12% ethyl acetate-hexane to afford compound 17.4 as a pale-yellow foam (60 g; 58.6 mmol; 73% yield based on compound 17.2). $^1H$ NMR (300 MHz, $CDCl_3$—$CCl_4$): δ 7.42–7.38(m; 2H), 7.31–7.20(m; 3H), 5.22(t; J=9.9 Hz; 1H), 5.19(t; J=9.3 Hz; 1H), 4.92–4.82(m; 2H), 4.77(t; J=9.3 Hz; 1H), 4.62(d; J=6.9 Hz; 1H), 4.51–4.45(m; 2H), 4.12(m; 1H), 4.07(d; J=11.7 Hz; 1H), 3.94(dd; J=7.8 Hz, 12.3 Hz; 1H), 3.77(t; J=9.6 Hz; 1H), 3.67(t; J=8.7 Hz; 1H), 3.54(m; 1H); 1.21(s; 9H), 1.15(s; 9H), 1.14(s; 9H), 1.13(s; 9H), 1.09(s; 9H), 1.07(s; 9H), 1.04(s; 9H). $^{13}C$ NMR (75.4 MHz, $CDCl_3$—$CCl_4$): δ 186.38, 186.15, 185.61, 185.14, 184.97, 184.47, 141.85, 140.38, 137.47, 136.89, 107.97, 94.67, 85.88, 81.92, 81.21, 81.02, 79.88, 78.46, 77.10, 70.93, 70.68, 47.45, 47.39, 47.35, 47.30, 47.25, 35.90, 35.85, 35.76, 35.70, 35.60. IR (neat): 2972.35 (s), 2935.99 (m), 2908.41 (m), 2873.15 (m), 1742.63 (s), 1479.99 (s) 1279.66 (s), 1141.22 (s). TLC $R_f$=0.61 (20% ethyl acetate-hexane). FAB MS: for $C_{53}H_{82}SO_{17}$ [M+Na] calcd. m/z 1046, found m/z 1046. Anal. Calcd. for $C_{53}H_{82}SO_{17}$ (1023.29): C, 62.21%; H, 8.08%; S, 3.13%. Found: C, 62.09%; H, 8.16%; S, 3.02%.

Example II-10

Synthesis of Phenyl 2-azido-2-deoxy-3,6-di-O-acetyl-4-O-(tetra-O-acetyl-β-D-glucopyranosyl)-1-thio-α-D-glucopyranoside (compound 18.4).

As depicted in Scheme 18, compound 18.1 (30 g; 53.5 mmol) is dissolved in acetonitrile (210 mL, HPLC grade) and transferred to a 3-neck, 1-liter round bottom flask equipped with a condenser and a mechanical stirrer. Hexa-O-acetyl-cellobial (compound 17.1) is prepared in two steps from commercially available α-D-cellobiose octaacetate. α-D-cellobiose octaacetate is quantitatively converted to hepta-O-acetyl cellobiosidyl bromide using a solution of hydrobromic acid in acetic acid [Zemplén, G., Csürös, Z., Bruckner, Z. *Ber.* (1928), 61: 927]. The bromide is then reduced to the lactal using zinc dust, aqueous acetic acid and chloroplatinic acid (promoter) in nearly quantitative yield [Haworth, W. N., Hirst, E. L., Streight, H. R. L., Thomas, H. A., Webb, J. I. *J Chem. Soc.* (1930), 2639].

The system is cooled to −25° C. in an ethylene glycol-dioxane bath. Under intense stirring, cerium ammonium nitrate (90 g; 164 mmol) is added to the system in small portions, followed by sodium azide (5.3 g; 81.5 mmol). The reaction is kept at −25° C. until all starting material has been consumed (6–7 hours of reaction), as judged by TLC (compound 18.1 has $R_f$=0.33 in 50% ethyl acetate-hexane). The reaction mixture is then filtered and the residue is washed with toluene (500 mL). The filtrate is treated with water (500 mL), the organic layer is reserved and the aqueous layer is backwashed with ethyl acetate (200 mL). The combined organic layers are washed with brine (3×100 mL), dried over anhydrous $Na_2SO_4$ and concentrated under vacuum to afford crude compound 18.2 as a white foam (40 g).

Compound 18.2 is dissolved in a solution of glacial acetic acid (110 mL), concentrated sulfuric acid (2 mL) and acetic anhydride (25 mL). The mixture is kept at 40° C. for two hours, cooled to room temperature and poured into a mixture of ice and water (1 L) under agitation. The white solid formed is collected by filtration and washed with cold water (250 mL). The solid is dissolved in methylene chloride (250 mL), washed with saturated $NaHCO_3$ solution (2×100 mL) and brine (1×100 mL), dried over anhydrous $Na_2SO_4$ and concentrated under vacuum to afford compound 18.3(31 g).

Compound 18.3 (31.2 g; 47.2 mmol) is azeotroped twice from toluene, dissolved in methylene chloride (anhydrous, 100 mL) and treated with thiophenol (10 mL; 97.1 mmol) and $BF_3$-etherate (60 mL; 473 mmol). The system is refluxed at 50° C. for 2 hours, cooled to room temperature and poured into saturated aqueous $NaHCO_3$ (500 mL). The organic layer is washed with saturated aqueous $NaHCO_3$ (2×100 mL) and brine (2×100 mL), dried over anhydrous $Na_2SO_4$ and concentrated to dryness. The crude product (42 g) is purified by flash chromatography using 40% ethyl acetate-hexane as eluent. Recrystallization from hexane affords analytically pure compound 18.4 (10 g; 14.1 mmol) as a white solid. mp 198–200° C., dec. $^1$H NMR (300 MHz, CDCl$_3$): δ 7.49–7.46(m; 2H), 7.31–7.26(m; 3H), 5.58(d; J=5.4 Hz; 1H), 5.29(dd; J=9.3 Hz, 10.5 Hz; 1H), 5.15(t; J=9.3 Hz; 1H), 5.09(t; J=9.6 Hz; 1H), 4.94(t; J=9.0 Hz; 1H), 4.51(d; J=8.1 Hz; 1H), 4.47(m; 1H), 4.40(m; 2H), 4.17(dd; J=5.7 Hz, 12.0 Hz; 1H), 4.05(dd; J=2.1 Hz, 12.3 Hz; 1H), 3.96(dd; J=5.4 Hz, 10.5 Hz; 1H), 3.74–3.64(m; 2H), 2.11(s; 3H), 2.08(s; 3H), 2.05(s; 3H), 2.04(s; 3H), 2.00(s; 3H), 1.98(s; 3H). $^{13}$C NMR (75.4 MHz, CDCl$_3$): δ 179.13, 178.91, 178.84, 177.91, 177.64, 141.40, 140.66, 137.81, 136.59, 109.42, 95.21, 81.61, 80.66, 80.26, 79.78, 78.19, 76.36, 70.56, 70.19, 29.43–29.20 (br). IR (neat): 2953.58 (w), 2110.57 (s), 1750.57 (s), 1370.48 (m), 1223.18 (s), 1038.58 (m). TLC R$_f$=0.29 (50% ethyl acetate-hexane). Anal. Calcd. for C$_{30}$H$_{37}$N$_3$SO$_{15}$ (711.70): C, 50.63%; H, 5.24%; N, 5.90%; S, 4.50%. Found: C, 50.90%; H, 5.36%; N, 5.62%; S, 4.43%. FAB+ for C$_{30}$H$_{37}$N$_3$SO$_{15}$ [MNa] calcd m/z 734, found m/z 734.

Example II-11
Synthesis of Phenyl 2-deoxy-2-N-trifluoroacetamido-3,4,6-tri-O-acetyl-1-thio-β-D-glucopyranose (compound 19.5) and Phenylsulfenyl-2-deoxy-2-N-trifluoroacetamido-3,4,6-tri-O-acetyl-β-D-glucopyranose (compound 19.6)

As depicted in Scheme 19, D-glucosamine hydrochloride is converted into compound 19.1 according to a procedure adapted from Bergman, M, et al., *Chem. Ber.*, 975 (1931). Glucosamine hydrochloride (50 g; 0.232 mol) is dissolved in 240 mL of 1M aqueous sodium hydroxide, forming a colorless solution. Anisaldehyde (28.5 mL; 0.235 mol) is added via syringe under intense stirring, forming a turbid solution. After several minutes of agitation, a white precipitate is formed. The system is kept in an ice bath for one hour to ensure complete precipitation. The solid is then collected by filtration and washed with water (2×200 mL) and a 1:1 mixture of methanol and ether (2×200 mL). The precipitate is dried overnight under vacuum, affording compound 19.1 (50 g; 72% yield). $^1$H NMR (300 MHz, DMSO-d$_6$): δ 8.17 (s, 1H), 7.74 (d, 2H, J=8.1 Hz), 7.04(d, 2H, J=7.8 Hz), 6.60 (d, 1H, J=6.6 Hz), 4.99 (d, 1H, J=4.5 Hz), 4.88 (d, 1H, J=4.8 Hz), 4.75 (d, 1H, J=7.2 Hz), 4.62 (t, 1H, J=5.4 Hz), 3.85 (s, 3H), 3.69(dd, 1H, J=5.4, 11.1 Hz), 3.58–3.42 (m, 2H), 3.32–3.16 (m, 2H), 2.85 (t, 1H, J=8.7 Hz). $^{13}$C NMR (75.4 MHz, DMSO-d$_6$): δ 161.24, 161.06, 129.65, 129.11, 113.91, 95.64, 78.21, 76.88, 74.61, 70.36, 61.27, 55.29. Anal. Calcd. for C$_{14}$H$_{19}$NO$_6$ (297.31): C, 56.56%; H, 6.44%; N, 4.71%. Found: C, 55.97%; H, 6.38%; N, 4.56%. mp 148–150° C. (dec).

Compound 19.1 (50 g; 0.168 mol) is treated with acetic anhydride (150 mL; 1.59 mol), pyridine (79.10 g/mol; 3.34 mol) and DMAP (0.5 g) in an ice-water bath. The solid slowly goes into solution and the reaction mixture is kept at room temperature overnight. The solution is poured into 1.5 L of ice, forming a white crystalline solid. The crystals are collected by filtration, washed with water (2×100 mL) and ether (2×100 mL) and dried under vacuum to afford compound 19.2 (60 g; 77% yield). TLC R$_f$=0.45 (50% ethyl acetate-hexane). $^1$H NMR (300 MHz, CDCl$_3$): δ 8.15 (s, 1H), 7.64 (d, 2H, J=8.4 Hz), 6.91 (d, 2H, J=8.7 Hz), 5.94 (d, 1H, J=8.1 Hz), 5.42 (t, 1H, J=9.3 Hz), 5.14 (t, 1H, J=9.6 Hz), 4.37 (dd, 1H, J=4.5, 12.3 Hz), 4.12 (dd, 1H, J=2.1, 12.6 Hz), 3.97 (ddd, 1H, J=2.4, 4.8, 9.6 Hz), 3.84 (s, 3H), 3.44 (t, 1H, J=9.6 Hz), 2.10 (s, 3H), 2.03 (s, 3H), 2.01 (s, 3H), 1.88 (s, 3H). $^{13}$C NMR (75.4 MHz, CDCl$_3$): δ 170.69, 169.89, 169.54, 168.77, 164.27, 162.26, 130.22, 128.24, 114.02, 93.12, 73.20, 72.91, 72.72, 67.98, 61.78, 55.39, 20.79, 20.67, 20.49 (br). IR (neat, cm$^{-1}$): 2948, 2869, 1752, 1640, 1606, 1508, 1372, 1223, 1039. FAB+ for C$_{22}$H$_{27}$NO$_{10}$: [MH] calcd m/z 466, found m/z 466; [MNa] calcd m/z 488, found m/z 488. Anal. Calcd. for C$_{22}$H$_{27}$NO$_{10}$ (465.46): C, 56.77%; H, 5.85%; N, 3.01%. Found: C, 56.56%; H, 5.90%; N, 2.99%. mp 168–172° C. (dec.).

Compound 19.2 (50 g; 0.108 mol) is dissolved in 250 mL of refluxing acetone and to this solution is added dropwise 25 mL of 5N HCl. After five minutes a white thick precipitate forms and the system is cooled to room temperature. The precipitate is filtered and washed with acetone (100 mL) and ether (2×250 mL). The resulting product, compound 19.3 is dried under vacuum overnight (41.8 g, quantitative). $^1$H NMR (300 MHz, DMSO-d$_6$): δ 8.93 (s, br, 2.6H), 5.97 (d, 1H, J=8.7 Hz), 5.42 (t, 1H, J=9.9 Hz), 4.99 (t, 1H, J=9.3 Hz), 4.25 (dd, 1H, J=3.9, 12 Hz), 4.11–4.03 (m, 2H), 3.62 (t, 1H, J=9.3 Hz), 2.23 (s, 3H), 2.09 (s, 3H), 2.05 (s, 3H), 2.03 (s, 3H). $^{13}$C NMR (75.4 MHz, DMSO-d$_6$): δ 169.98, 169.78, 169.32, 168.67, 90.08, 71.59, 70.31, 67.76, 61.25, 52.11, 20.97, 20.88, 20.51, 20.37. IR (neat, cm$^{-1}$): 2805, 2745, 2683, 1757, 1595, 1519, 1366, 1247, 1208, 1084, 1060, 1040. FAB+ for C14H$_{27}$NO$_9$Cl: [M—Cl] calcd m/z 348, found m/z 348; [MNa—HCl] calcd m/z 370, found m/z 370. Anal. Calcd. for C$_{14}$H$_{22}$NO$_9$Cl (383.78): C, 43.81%; H, 5.78%; N, 3.65%; Cl, 9.24%. Found: C, 43.80%; H, 5.80%; N, 3.57%; Cl, 9.15%. mp >200° C.

Compound 19.3 (41.6 g; 0.108 mol) is suspended in pyridine (90 mL; 1.11 mol) and methylene chloride (90 mL). Trifluoroacetic anhydride (18.5 mL; 0.131 mol) is slowly added via syringe. The solid slowly goes into solution with a slight rise in temperature. The reaction mixture is concentrated in vacuo to dryness. The residue is dissolved in 100 mL methylene chloride and washed with 2N HCl (1×100 mL), aqueous NaHCO$_3$ (2×100 mL) and brine (1×50 mL), and dried over anhydrous Na$_2$SO$_4$. The clear solution is concentrated to dryness affording compound 19.4 (48.5 g; 0.109 mol; quantitative) as an off-yellow solid. TLC R$_f$=0.47 (50% ethyl acetate-hexane). $^1$H NMR (300 MHz, CDCl$_3$): δ 7.24 (d, 1H, J=9.0 Hz), 5.75 (d, 1H, J=9.0 Hz), 5.31 (t, 1H, J=10.0 Hz), 5.13 (t, 1H, J=9.6 Hz), 4.35 (q, 1H, J=9.9 Hz), 4.27 (dd, 1H, J=4.8, 12.6 Hz), 4.15 (dd, 1H, J=2.1, 12.6 Hz), 3.90 (ddd, 1H, J=2.1, 4.8, 9.9 Hz), 2.12 (s, 3H), 2.10 (s, 3H), 2.06 (s, 3H), 2.05 (s, 3H). $^{13}$C NMR (75.4 MHz, CDCl$_3$): δ 171.40, 170.63, 169.74, 169.23, 157.12 (q, J=38 Hz), 133.46, 131.10, 129.03, 128.77, 115.54 (J=288 Hz), 85.95, 75.90, 73.31, 68.209, 62.20, 53.20, 20.72, 20.42, 20.37 (br). IR (neat, cm$^{-1}$): 3326, 3100, 2952; 1748, 1560, 1374, 1219, 1079, 1042. FAB+ for C$_{16}$H$_{20}$NO$_{10}$F$_3$: [MNa] calcd m/z 466, found m/z 466. Anal. Calcd. for C$_{16}$H$_{20}$NO$_{10}$F$_3$ (443.33): C, 43.35%; H, 4.55%; N, 3.16%. Found: C, 43.16%; H, 4.51%; N, 3.15%.

Compound 19.4 (48.25 g; 0.109 mol) is dissolved in 400 mL anhydrous methylene chloride and treated with thiophenol (17 mL; 0.166 mol) and boron trifluoride etherate (42 mL; 0.331 mol). The reaction mixture is left overnight at room temperature and then poured into a solution of 100 mL saturated aqueous NaHCO$_3$, 100 mL aqueous Na$_2$CO$_3$ and 50 mL brine. The organic layer is further washed with a mixture of 50 mL saturated aqueous NaHCO$_3$ and 50 mL aqueous Na$_2$CO$_3$. The organic layer is dried over anhydrous Na$_2$SO$_4$ and concentrated under vacuum. The resulting solid is washed with 300 mL boiling hexane and filtered. The filtrate is further washed with 300 mL ice-cold hexane and dried under vacuum to yield compound 19.5 (49.2 g; 0.099 mol; 92% yield). TLC R$_f$=0.54 (50% ethyl acetate-hexane). $^1$H NMR (300 MHz, CDCl$_3$): δ 7.51–7.48 (m, 2H), 7.33–7.26 (m, 3H), 7.02 (d, 1H, J=9.3 Hz), 5.28 (t, 1H, J=9.9 Hz), 5.03 (t, 1H, J=9.6 Hz), 4.78 (d, 1H, J=10.2 Hz), 4.22–4.13 (m, 2H), 4.08 (q, 1H, J=10.2 Hz), 3.78 (m, 1H), 2.08 (s, 3H), 2.00 (s, 3H), 1.93 (s, 3H). $^{13}$C NMR (75.4 MHz, CDCl$_3$): δ 168.32, 167.55, 166.15, 154.03 (q, J=38 Hz), 130.38, 128.02, 125.95, 125.68, 112.46 (q, J=288 Hz), 82.87, 72.82, 70.23, 65.13, 59.12, 50.12, 17.64, 17.34, 17.29. IR (neat, cm$^{-1}$): 3302, 3103, 2951, 2879, 1748, 1706, 1557, 1371, 1217, 1178, 1077, 1037. FAB+ for C$_{20}$H$_{22}$NSO$_8$F$_3$: [MNa] calcd m/z 516, found m/z 516. mp 178–180° C. (dec).

Compound 19.5 (49 g; 0.099 mol) is dissolved in DCM (500 mL) and cooled to −78° C. Sodium bicarbonate (0.5 g) and mCPBA (26.3 g; 68.7% pure; 0.104 mol) is added, and the temperature is slowly raised to −25° C. As the reaction progresses, the product precipitates out of solution. When the reaction is complete by TLC, it is quenched with 1 mL dimethyl sulfide and allowed to reach room temperature. The reaction mixture is diluted with 200 mL water, 200 mL aqueous NaHCO$_3$ and 100 mL CH$_2$Cl$_2$. The organic layer is washed with a mixture of 100 mL aqueous Na$_2$CO$_3$ and 100 mL brine, dried over anhydrous Na$_2$SO$_4$ and concentrated under vacuum. The solid is washed with 300 mL hot ether, filtered, and further washed with 300 mL of ice-cold ether and dried under vacuum, yielding compound 19.6 (48 g; 509 g/mol; 0.094 mol; 95% yield). TLC R$_f$=0.15–0.26 (50% ethyl acetate-hexane). $^1$H NMR (300 MHz, CDCl$_3$, diastereoisomers in 5:1 ratio): δ 8.37 (d, 0.16H, J=7.8 Hz), 7.83 (d, 0.84H, J=8.7 Hz), 7.68–7.41 (m, 5H), 5.65 (t, 0.16H, J=9.9 Hz), 5.45 (t, 0.84H, J=9.6 Hz), 5.02 (t, 0.16H, J=9.9 Hz), 4.96–4.88 (m, 1.84H), 4.21–3.94 (m, 3H), 3.81 (ddd, 0.84H, J=2.7, 3.9, 10.2 Hz), 3.68 (ddd, 0.16H, J=2.4, 6.0, 9.6 Hz), 2.22–1.93 (m, 9H). $^{13}$C NMR (75.4 MHz, CDCl$_3$, diastereoisomers in 5:1 ratio): δ 170.76, 170.42, 169.33, 157.27 (q, J=38 Hz), 137.42, 137.00, 131.970, 131.88, 129.08, 125.60, 125.40, 115.23 (q, J=288 Hz), 92.03, 88.52, 76.75, 76.28, 72.30, 71.53, 68.23, 67.58, 61.81, 61.33, 51.51, 50.17, 20.60, 20.49, 20.37. IR (neat, cm$^{-1}$): 3232, 3070, 2955, 1750, 1372, 1222, 1182, 1110, 1037. FAB+ for C$_{20}$H$_{27}$NSO$_9$F$_3$: [MNa] calcd m/z 532, found m/z 532. Anal. Calcd. for C$_{20}$H$_{22}$NSO$_9$F$_3$ (509.45): C, 47.15%; H, 4.35%; N, 2.75%; S, 6.29%. Found: C, 47.02%; H, 4.34%; N, 2.70%; S, 6,.21%. mp 134–140° C. (dec).

Example II-12

Synthesis of Sulfoxides from the Corresponding Thiophenyl Compounds

Phenyl 1-thio saccharides of the present invention can be converted into the corresponding sulfoxides by methods described elsewhere and by Methods A and B described hereinbelow. For instance, the sulfoxide compounds M, N and O depicted in Table 2 hereinbelow can be prepared using the methods described in U.S. Ser. Nos. 08/281,167 and 08/822,131, the disclosures of which are incorporated herein by reference. The thiophenyl (sulfide) starting material for sulfoxide K is synthesized by literature methods [see, e.g., Alper, P. B., et al., *Tetrahedron Lett.*, 34: 6029 (1996); Ferrier, R. J., et al., *Carbohydrate Res.*, 52: 63 (1976)]. The starting material (sulfide) for sulfoxide L is synthesized using literature methods [see, e.g., Anisuzzaman, A. K. M., et al., *Carbohydrate Res.*, 169: 258 (1987); Broddefalk, J., et al., *J. Carbohydrate Chem.*, 13(1):129 (1994); Ferrier, R. J., et al., *Carbohydrate Res.*, 52: 63 (1976)]. Other sulfoxide donor molecules are prepared by the following methods:

Method A: To a stirred mixture of appropriate sulfide (0.005 M), Ac$_2$O (0.0055 M), and silica gel (1 g, 230–400 mesh) in CH$_2$Cl$_2$ (100 mL) is added aqueous 30% H$_2$O$_2$ solution (0.006 M). After being stirred at RT between 2 and 24 h, with the reaction progress being monitored by TLC, the reaction mixture is filtered through a fine frit sintered funnel and the filtrate is washed with aqueous sodium bisulfite (200 mL), aqueous NaHCO$_3$ (200 mL) and brine (200 mL). The organic layer is dried over Na$_2$SO$_4$ and concentrated under vacuum to furnish a mixture of R and S sulfoxides.

Method B: To a cooled (−78° C.) solution of the appropriate sulfide (0.005 M) in CH$_2$Cl$_2$ (100 mL), m-CPBA (0.0055 M) is added, and the temperature is slowly raised to −25° C. over a 2 h period. After filtering, the filtrate is washed with aqueous sodium bisulfite (200 mL), aqueous NaHCO$_3$ (200 mL) and brine (200 mL). The organic layer is dried over Na$_2$SO$_4$ and concentrated under vacuum to furnish a mixture of R and S sulfoxides.

TABLE 2

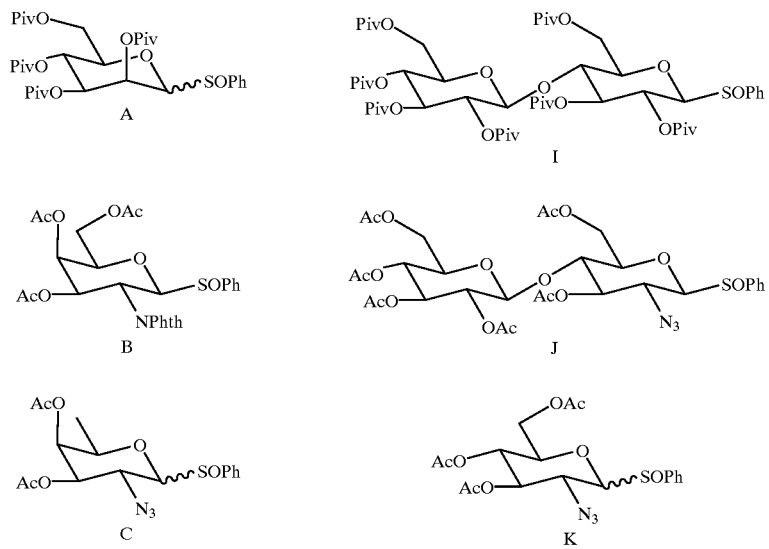

TABLE 2-continued

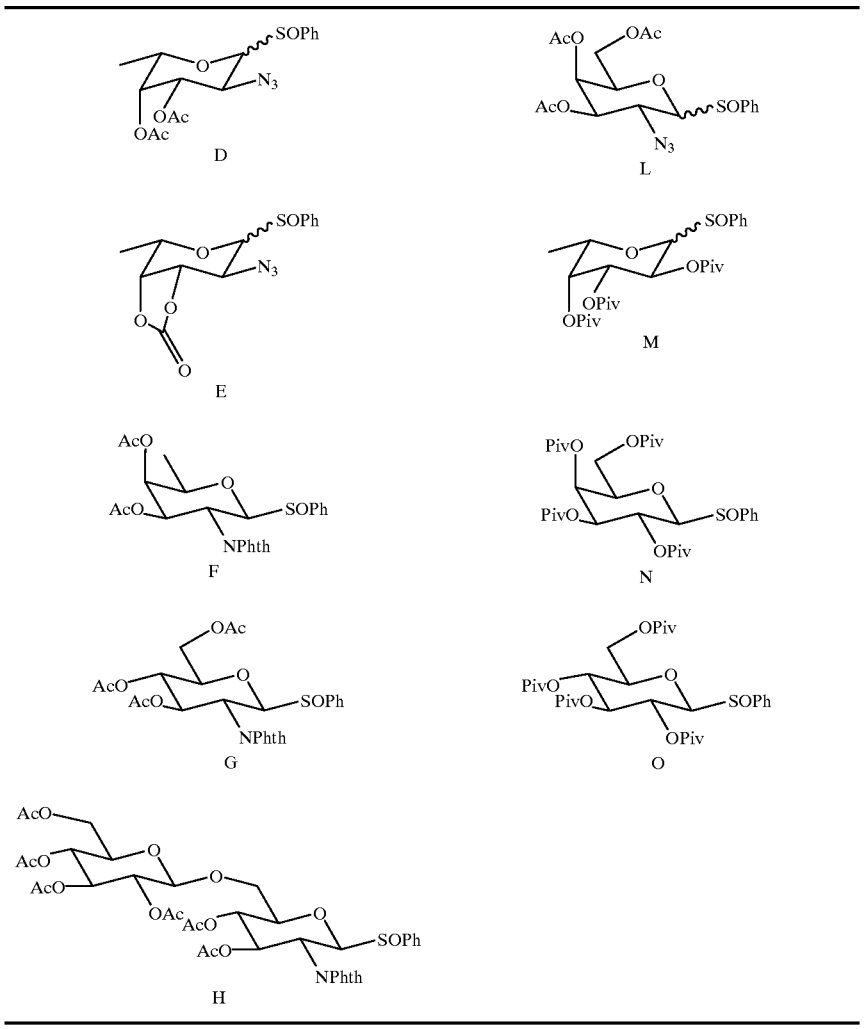

Reaction yield, TLC, $^1$H NMR, and mass spectral data for the compounds appearing in Table 2 are given below:

Phenylsulfenyl 2,3,4,6,-tetra-O-pivaloyl-α-D-mannopyranoside (A): 90% Yield, TLC R$_f$0.4 (1:2 EtOAc/hexane); $^1$H NMR (300 MHz, CDCl$_3$): δ 7.65 (m, 2H), 7.54 (m, 3H), 5.80–5.54 (m, 3H), 4.80–4.60 (m, 1H), 4.52 (d, 0.6H, J=3.3 Hz), 4.42 (d, 0.4H, J=3.3 Hz), 4.20–4.00 (m, 2H), 1.10–1.02 (m, 36H); MS (fab): 647 (M+Na)$^+$.

Phenylsulfenyl 2-phthalimido-2-deoxy-3,4,6-tri-O-acetyl-β-D-galactopyranoside (B): 90% Yield, TLC R$_f$0.25 (1:1 EtOAc/hexane); $^1$H NMR (300 MHz, CDCl$_3$): δ 7.90–7.20 (m, 9H), 5.84 and 5.72 (each dd, 1H, J=10.2 and 3.5 Hz), 5.47 ( d, 1H, J=3.5 Hz), 5.20 and 5.27 (each d, 1H, J=10.2 Hz), 5.60 and 4.88 (each t, 1H, J=10.2 Hz), 4.20–4.02 (m, 3H), 2.18–1.95 (m, 9H). MS (fab): 566 (M+Na)$^+$.

Phenylsulfenyl 2-azido-2-deoxy-3,4-di-O-acetyl-α,β-D-fucopyranoside (C): 93% Yield, TLC R$_f$0.45 (1:2 EtOAc/hexane); $^1$H NMR (300 MHz, CDCl$_3$): δ 7.72–7.54 (m, 5H), 5.71 and 5.67 (two d, each 0.3H, J=3.3 Hz), 4.71 (d, 0.4H, J=5.7 Hz), 4.55–4.16 (m, 3H), 2.14–2.07 (m, 6H), 1.04–0.92 (m, 3H). MS (fab): 404 (M+Na)$^+$.

Phenylsulfenyl 2-azido-2-deoxy-3,4-di-O-acetyl-α,β-L-fucopyranoside (D): 83% Yield, TLC R$_f$0.40 (1:2 EtOAc/hexane); $^1$H NMR (300 MHz, CDCl$_3$): δ 7.75–7.50 (m, 5H), 5.65 and 5.62 (each d, 1H, J=9.6 Hz and 3.6 Hz), 5.38 and 5.20 (each d, 1H, J=6.3 Hz), 4.72 (m, 1H), 4.42 (m, 1H), 4.24 (m, 1H), 2.15–2.02 (m, 6H). MS (fab): 404 (M+Na)$^+$.

Phenylsulfenyl 2-azido-2-deoxy-3,4-di-O-carbonyl-α,β-L-fucopyranoside (E): 93% Yield, TLC R$_f$0.30 (1:2 EtOAc/hexane); $^1$H NMR (300 MHz, CDCl$_3$): δ 7.72–7.54 (m, 5H), 5.18 and 5.05 (each dd, 1H, J=8.4 Hz and 3.6 Hz), 4.95 (d, 0.6H, J=3.3 Hz), 4.80–4.65 (m, 3H), 4.59 (d, 0.4H, J=4.8 Hz), 1.04–0.92 (m, 3H). MS (fab): 350 (M+Na)$^+$.

Phenylsulfenyl 2-phthalimido-2-deoxy-3,4-di-O-acetyl-β-D-fucopyranoside (F): 93% Yield, TLC R$_f$0.22 (1:2 EtOAc/hexane); $^1$H NMR (300 MHz, CDCl$_3$): δ 7.80–7.24 (m, 5H), 5.82 and 5.65 (each dd, 1H, J=10.2 Hz and 3.6 Hz), 5.42 and 5.35 (each d, 1H, J=10.2 Hz), 5.25 (m, 1H), 5.02 and 4.81 (each t, 1H, J=10.2 Hz), 4.02 (m, 1H), 1.10–1.02 (m, 3H). MS: 485 (M+NH$_4$)$^+$.

Phenylsulfenyl 2-phthalimido-2-deoxy-3,4,6-tri-O-acetyl-β-D-glucopyranoside (G): 95% Yield, TLC R$_f$0.30 (1:1 EtOAc/hexane); $^1$H NMR (300 MHz, CDCl$_3$) δ 7.86–7.06 (m, 9H), 5.80 and 5.76 (2t, 1H, J=9.6 Hz), 5.46 and 5.43 (2d, 1H, J=9.6 Hz), 5.16 and 5.08 (2t, 1H, J=9.6 Hz), 4.91 and 4.68 (2t, 1H, J=9.6 Hz), 4.10–4.06 (m, 2H), 3.95 and 3.84 (2m, 1H), 2.05–1.85 (m, 9H). MS (fab): 566 (M+Na)$^+$.

Phenylsulfenyl 6-O-(2,3,4,6-tetra-O-acetyl-β-D-glucopyranosyl)-(1→6)-2-phthalimido-2-deoxy-3,4-di-O- acetyl-β-D-glucopyranoside (H): 85% Yield, TLC $R_f$ 0.15 (2:1 EtOAc/hexane); $^1$H NMR (300 MHz, CDCl$_3$): δ 7.95–7.40 (m, 9H), 5.82–5.65 (m, 2H), 5.46 and 5.42 (each d, 1H, J=10.2 Hz), 5.30–5.20 (m, 4H), 5.02 (t, 1H, J=10.2 Hz), 4.81 (t, 1H, J=10.2 Hz), 4.10–3.95 (m, 4H), 2.23–1.90 (m, 18H). MS: 849 (M+NH$_4$)$^+$.

Phenylsulfenyl 4-O-(2,3,4,6-tetra-O-pivaloyl-β-D-glucopyranosyl)-(1→4)-2,3,6-tri-O-pivaloyl-β-D-glucopyranoside (I): 80% Yield, TLC $R_f$ 0.35 (1:2 EtOAc/hexane); $^1$H NMR (300 MHz, CDCl$_3$): δ 7.70–7.50 (m, 5H), 5.40–5.18 (m, 3H), 4.96–4.82 (m, 3H), 4.52–4.42 (m, 2H), 4.10–3.85 (m, 4H), 3.78–3.40 (m, 2H), 1.35–1.07 (m, 63H). MS: 1056 (M+NH$_4$)$^+$.

Phenylsulfenyl 4-O-(2,3,4,6-tetra-O-acetyl-β-D-glucopyranosyl)-(1→4)-2-azido-2-deoxy-3,6-di-O-acetyl-β-D-glucopyranoside (J): 85% Yield, TLC $R_f$ 0.15 (1:1 EtOAc/hexane); $^1$H NMR (300 MHz, CDCl$_3$): δ 7.75–7.60 (m, 5H), 5.78 and 5.77 (each d, 1H, J=5.4 Hz), 5.08 (m, 2H), 5.01 (t, 1H, J=9.6 Hz), 4.65 (d, 1H, J=9.6 Hz), 4.43 (m, 2H), 4.35–4.15 (m, 3H), 3.90–3.50 (m, 4H), 2.05–1.95 (m, 18H). MS: 729 (M+NH$_4$)$^+$.

Phenylsulfenyl 2-azido-2-deoxy-3,4,6-tri-O-acetyl-α,β-D-glucopyranoside (K): 92% Yield, TLC $R_f$ 0.25 (1:1 EtOAc/hexane); $^1$H NMR (300 MHz, CDCl$_3$): δ 7.65–7.45 (m, 5H), 5.15 (t, J=10 Hz), 4.97 (t, J=10 Hz), 4.23–4.18 (m, 3H), 3.90 (t, J=10 Hz), 3.75–3.70 (m, 1H), 2.10 (s, 6H), 2.00 (s, 3H), MS (fab): 462 (M+Na)$^+$.

Phenylsulfenyl 2-azido-2-deoxy-3,4,6-tri-O-acetyl-α,β-D-galactopyranoside (L): 90% Yield, TLC $R_f$ 0.35 (1:1 EtOAc/hexane); $^1$H NMR (300 MHz, CDCl$_3$): δ 7.74–7.53 (m, 5H), 5.71 and 5.78 (each d, 0.5H, J=3.3 Hz), 5.29 (t, 0.5H, J=5.7 Hz), 5.36 (d, 0.5H, J=3.3 Hz), 4.98 (dd, 0.5H, J=10.2 Hz and 3.3 Hz), 4.71 (d, 0.5H, J=4.8 Hz), 4.50–3.70 (m, 4.5H), 2.15–1.94 (m, 9H). MS (fab): 462 (M+Na)$^+$.

Phenylsulfenyl 2,3,4-tri-O-pivaloyl-α,β-L-fucopyranoside (M): 73% Yield, TLC $R_f$ 0.3 (1:2 EtOAc/hexane); $^1$H NMR (300 MHz, CDCl$_3$): δ 7.82–7.50 (m, 5H), 5.18 and 4.98 (m, 3H), 4.63 and 4.42 (each d, 1H, J=9.9 Hz), 3.94–3.80 (m, 1H), 1.20–0.93 (m, 27H). MS (fab): 547 (M+Na)$^+$.

Phenylsulfenyl 2,3,4,6,-tetra-O-pivaloyl-β-D-galactopyranoside (N): 80% Yield, TLC $R_f$ 0.4 (1:2 EtOAc/hexane); $^1$H NMR (300 MHz, CDCl$_3$): δ 7.80–7.50 (m, 5H), 5.58–5.06 (m, 3H), 4.65 and 4.43 (each d, 1H, J=9.6 Hz), 4.12–3.70 (m, 3H), 1.15–0.93 (m, 36H); MS (fab): 647 (M+Na)$^+$.

Phenylsulfenyl 2,3,4,6,-tetra-O-pivaloyl-β-D-glucopyranoside (O): 88% Yield, TLC $R_f$ 0.3 (1:2 EtOAc/hexane); $^1$H NMR (300 MHz, CDCl$_3$): δ 7.65–7.54 (m, 5H), 5.38–5.18 (m, 2H), 5.04–4.92 (m, 1H), 4.46 and 4.28 (each d, 1H, J=9.6 Hz), 4.20–4.00 (m, 2H), 3.76 and 3.60 (each m, 1H), 1.18–0.92 (m, 36H); MS (fab): 647 (M+Na)$^+$.

PART III. SYNTHESIS OF LIPID GROUPS

Example III-1

Synthesis of (R)-methyl-2-isopentoxy-3-hydroxy-propionate (compound 20.4a).

As shown in Scheme 20, compound 20.1 (1,3;4,6-di-O-benzylidene-D-mannitol [Baggett, N., *J. Chem. Soc., Perkins Trans.*, 1:1123 (1977)]) (270 g; 0.753 mol), is added to DMF (anhydrous, 4 L) in a 12-liter, 3-neck round bottom flask under a N$_2$ atmosphere. Sodium hydride (54.4 g; 2.27 mol) is slowly added to the stirred mixture (the temperature is kept under 25° C. throughout the addition). 1-bromo-3-methylbutane (252.7 g; 1.673 mol) and DMF (400 mL) are sequentially added. The system is stirred at 70° C. for 3 hours and cooled to room temperature overnight. The reaction mixture is diluted with ethyl ether (10 L) and transferred to a 10-gallon separatory funnel containing a mechanical stirrer. Aqueous HCl solution (3 M; 3 L) is slowly added to the system. After 30 minutes of intense stirring, the layers are separated and the organic layer is washed with water (3 L). The aqueous layers are combined and extracted with ethyl ether (3 L). All the organic layers are combined, washed with brine (3 L), dried over anhydrous Na$_2$SO$_4$ (1 kg) and concentrated under vacuum. The dry solid is treated with warm ethyl acetate (1.5 L) and silica gel 60 (600 g), and concentrated under vacuum. The immobilized crude product is then purified on a Biotage Flash 75 system (using a stepwise gradient of 5% to 100% ethyl acetate-hexane) to afford compound 20.2a (180 g; 0.361 mol; 48% yield). $^1$H NMR (300 MHz, CDCl$_3$): δ 7.51–7.49(m; 4H), 7.39–7.25 (m; 6H), 5.48 (s; 2H), 4.42(dd; J=4.8 Hz, 10.5 Hz; 2H), 3.98 (d; J=9.0 Hz; 2H), 3.85(m; J=5.1 Hz, 9.0 Hz, 10.2 Hz; 2H), 3.70–3.55(m; 4H), 3.48(m; 2H), 1.70(m; J=6.6 Hz; 2H), 1.42(m; J=6.6 Hz; 4H), 0.88(d; J=6.6 Hz; 12H). TLC $R_f$=0.35 (10% ethyl acetate-hexane). FAB MS: for C$_{30}$H42O$_6$ [MH] calcd m/z 499, found m/z 499.

Compound 20.2a (176 g; 0.353 mol) is dissolved in ethyl alcohol (2 L) and water (0.48 L) at 40° C., and concentrated HCl (37.6%; 313 mL) is added dropwise. The system is refluxed (80° C.) overnight and cooled to room temperature. Saturated NaHCO$_3$ solution (4 L) is added dropwise to obtain a final pH of 7, and the mixture is evaporated to dryness. The solid is triturated with boiling ethyl acetate (2×3 L) and the resulting solutions are filtered through a heated sintered funnel. The combined organic phases are dried over anhydrous Na$_2$SO$_4$ and concentrated under vacuum, yielding a yellow oil (126 g). The oil is treated with hot hexane (2 L) and silica gel 60 (250 g) and dried under vacuum. The immobilized crude product is loaded onto a Biotage Flash 75 system and sequentially eluted with 80% ethyl acetate-hexane, 100% ethyl acetate and 20% methanol-methylene chloride. The fractions containing product are concentrated to afford compound 20.3a (65.7 g; 0.20 mol; 58% yield). TLC $R_f$=0.25 (80% ethyl acetate-hexane). FAB MS: for C$_{16}$H$_{34}$O$_6$ [M+Na] calcd m/z 345, found m/z 345.

To a solution of compound 20.3a (65 g; 0.202 mol) in THF (3 L) is added a solution of NaIO$_4$ (107 g; 0.500 mol) in water (1.5 L) over the period of 40 minutes. The suspension is cooled to 10° C. and bromine (43.3 mL; 0.840 mol) is added dropwise over the period of 20 minutes. The reaction mixture is warmed to room temperature and stirred for 2 hours. Diethyl ether (3 L) and 5% aqueous sulfuric acid (1 L) are added. The organic layer is reserved and the aqueous layer is back-extracted with ether (2×1.5 L). The red organic layers are combined and treated with an aqueous saturated NaHSO$_3$ solution until a light yellow color is obtained (ca. 0.5 l of saturated NaHSO$_3$ solution). The organic layer is washed with water (1.5 L) and brine (2 L), dried over anhydrous Na$_2$SO$_4$, filtered and concentrated under vacuum to an oil (79.4 g). The oil is dissolved in methanol (1 L) and treated with concentrated HCl (12 M; 75.6 mL). The solution is stirred at 50° C. overnight, cooled to room temperature, neutralized with aqueous saturated NaHCO$_3$ solution (250 mL) and concentrated under vacuum. The residue is treated with methylene chloride (500 mL) and filtered. The filtrate is dried over anhydrous Na$_2$SO$_4$, filtered and concentrated under vacuum, affording a dark oil (62.3 g). The oil is directly loaded onto a Biotage Flash 75 system and eluted with a stepwise gradient of 20% to 30% ethyl acetate-hexane, affording compound 20.4a as a clear oil (58 g; 0.305 mol; 76% yield). $^1$H NMR (300 MHz, CDCl$_3$): δ 3.99(dd; J=3.6 Hz, 6.3 Hz; 1H), 3.88(dd; J=3.6 Hz, 11.7 Hz; 1H), 3.82–3.70(m; 5H), 3.45(m; 1H), 1.70(m; J=6.6 Hz; 1H), 1.50(m; J=6.6 Hz; 2H), 0.88(d; J=6.6 Hz; 6H). $^{13}$C NMR (75.4 MHz, CDCl$_3$): δ 179.96, 88.35, 78.30, 71.96, 60.61, 46.97, 33.51, 31.18, 31.08. IR (neat): 3466.1 (br), 2897.2 (s), 1738.6 (s), 1163.3 (s). TLC R$_f$=0.65 (50% ethyl acetate-hexane). FAB MS: for C$_9$H$_{18}$O$_4$ [MNa] calcd m/z 213; found m/z 213. Anal. Calcd. for C$_9$H$_{18}$O$_4$ (190.24): C, 9.54%; H, 56.82%. Found: C, 9.44%; H, 56.83%.

Example III-2

Synthesis of (R)-methyl 2-dodecoxy-3-hydroxy-propionate (compound 20.4b).

Compound 20.1 (290 g; 0.809 mol) is added to DMF (anhydrous, 4 L) in a 12-liter, 3-neck round bottom flask under a N$_2$ atmosphere. Sodium hydride (58 g; 2.42 mol) is slowly added to the stirred mixture, and the temperature is kept under 25° C. 1-bromo-dodecane (448 g; 1.798 mol) and DMF (1,220 mL) are sequentially added. The system is stirred at 70° C. for 4 hours and cooled to room temperature overnight. The dark brown reaction mixture is diluted with ethyl ether (10 L) and transferred to a 10-gallon separatory funnel containing a mechanical stirrer. Aqueous HCl solution (3 M; 4 L) is added to the system. After 30 minutes of intense stirring, methylene chloride (6 L) and water (3 L) are added and the layers are separated. The aqueous layer is backwashed with methylene chloride (2 L). The combined organic layers are washed with water (1×4 L) and brine (1×4 L). These aqueous washes are extracted with ethyl ether (2 L). The combined organic layers are dried over Na$_2$SO$_4$ (1 kg) and concentrated under vacuum, affording the crude product (622 g). The dry solid is dissolved in ethyl ether (2.0 L), treated with silica gel 60 (600 g) and concentrated under vacuum. The crude mixture is then purified on a Biotage Flash 75 system using a stepwise gradient of 0% to 10% ethyl acetate-hexane as eluent. The fractions containing pure compound are combined and concentrated, yielding compound 20.2b (209 g; 0.300 mol; 37% yield). $^1$H NMR (300 MHz, CDCl$_3$): δ 7.51–7.49(m; 4H), 7.39–7.25(m; 6H), 5.48(s; 2H), 4.42(dd; J=4.8 Hz, 10.5 Hz; 2H), 3.98(d; J=9.0 Hz; 2H), 3.85(td; J=5.1 Hz, 9.0 Hz, 10.2 Hz; 2H), 3.70–3.55 (m; 4H), 3.48(m; 2H), 1.55(m; 4H), 1.30(m; 36H), 0.85 (t; J=6.3 Hz; 6H). TLC R$_f$=0.58 (10% ethyl acetate-hexane).

Compound 20.2b (208 g; 0.300 mol) is dissolved in ethyl alcohol (2 L) and water (400 mL) at 40° C., and concentrated HCl (37.6%; 275 mL) is added dropwise. The system is refluxed at 80° C. overnight and cooled to room temperature. Saturated NaHCO$_3$ solution (3 L) is added dropwise to obtain a final pH of 7, and the mixture is evaporated to dryness. The solid is triturated with boiling ethyl acetate (4 L in the first round; 2 L in the second round) and the resulting solutions are filtered through a heated sintered funnel. The organic phases are dried over anhydrous Na$_2$SO$_4$. Since crystallization of product is observed at this stage, the system is heated to 65° C. and filtered through a warm sintered funnel. The solid is rinsed with warm ethyl acetate (2 L) and discarded. The organic phase is concentrated to a solid residue (213 g). The residue is recrystallized from 80% ethyl acetate-hexane, affording compound 20.3b as a white solid (104 g; 0.199 mol; 67% yield). TLC R$_f$=0.29 (80% ethyl acetate-hexane). FAB MS: for C$_{30}$H$_{62}$O$_6$ [MNa], calcd m/z 542, found m/z 542.

To a solution of compound 20.3b (104 g; 0.199 mol) in THF (4 L) is added a solution of sodium periodate (106 g; 0.495 mol) in water (1.5 L) over the period of 40 minutes. The resulting suspension is cooled to 5° C. and bromine (43 mL; 0.839 mol) is added dropwise over the period of 20 minutes. The reaction mixture is warmed to room temperature and left overnight under intense stirring. Diethyl ether (4 L) and a 5% sulfuric acid solution (1 L) are added. The organic layer is reserved and the aqueous layer is back-extracted with ether (3×1.5 L). The red organic layers are combined and treated with an aqueous saturated NaHSO$_3$ solution until a light yellow color is obtained (ca. 1 L of NaHSO$_3$ solution). The organic layer is washed with water (1×2 L) and brine (1×3 L), dried over anhydrous Na$_2$SO$_4$, filtered and concentrated under vacuum to an oil (118 g). The oil is dissolved in methanol (1.68 L) and treated with concentrated HCl (12M; 112 mL). The solution is stirred at 50° C. overnight, cooled to room temperature, neutralized with aqueous saturated sodium bicarbonate solution (1.25 L) and concentrated under vacuum. The residue is treated with methylene chloride (2.5 L) and filtered. The filtrate is dried over anhydrous Na$_2$SO$_4$, filtered and concentrated under vacuum, affording an oil (107 g). The oil is absorbed onto silica gel 60 (225 g) using methylene chloride as solvent, loaded onto a Biotage Flash 75 system and eluted with a stepwise gradient of 15% to 30% ethyl acetate-hexane. Compound 20.4b is isolated as a clear oil (98 g; 0.305 mol; 85% yield). $^1$H NMR (300 MHz, CDCl$_3$): δ 3.99(dd; J=3.6 Hz, 6.0 Hz; 1H), 3.88(dd; J=3.6 Hz, 11.4 Hz; 1H), 3.82–3.70 (m; 5H), 3.44 (m; 1H), 1.60(m; 2H), 1.30(br; 18H), 0.84(t; J=6.3 Hz; 3H). $^{13}$C NMR (75.4 MHz, CDCl$_3$): δ 179.96, 88.34, 79.97, 71.94, 60.58, 40.50, 38.25, 38.22, 38.17, 38.01, 37.94, 34.53, 31.27, 22.68. IR (neat): 3466.1 (br), 2897.2 (s), 1738.6 (s), 1428.0 (m), 1163.3 (s). TLC R$_f$=0.62 (50% ethyl acetate-hexane). FAB MS: for C$_{16}$H$_{32}$O$_4$ [MNa] calcd m/z 311; found m/z 311. Anal. Calcd. for C$_{16}$H$_{32}$O$_4$ (288.43): C, 66.63%; H, 11.18%. Found: C, 63.60%; H, 10.63%.

Example III-3

Synthesis of (R)-methyl-2-docosoxy-3-hydroxy-propionate (compound 20.4c).

Compound 20.1 (400 g; 1.116 mol) is added to DMF (anhydrous, 4 L) in a 12-liter, 3-neck round bottom flask under a N$_2$ atmosphere. Sodium hydride (80.6 g; 3.36 mol) is added to the stirred mixture, while the temperature is kept under 25° C. 1-bromo-docosane (965.6 g; 2.479 mol) and DMF (800 mL) are sequentially added. The system is stirred at 70° C. for 6 hours and cooled to room temperature overnight. The dark brown reaction mixture is treated with HCl (3M; 500 mL), as the temperature is kept under 40° C. The reaction mixture is diluted with methylene chloride (4 L) and saturated brine (4 L), forming a viscous emulsion. The emulsion is shaken with hexane (4 L), yielding two distinct layers. The hexane-containing top layer is reserved (fraction A; 840 g). The bottom layer is then heated to reflux and transferred to a separatory funnel. Upon cooling, two layers separate. The aqueous top layer is discarded and the bottom layer is reserved (fraction B; 1240 g). Fractions A and B are separately concentrated to dryness, dissolved in hot methylene chloride, immobilized on silica gel 60 (900 g and 1240 g, respectively), and purified on a Flash 150 Biotage system using a Flash 150 module. In each run, unreacted 1-bromodocosane is eluted with pure hexane and the product is eluted with 5% ethyl acetate-hexane to give compound 20.2c (349 g; 0.358 mol; 31.8% yield based on compound 20.1). $^1$H NMR (300 MHz, CDCl$_3$): δ 7.51–7.49 (m; 4H), 7.39–7.25(m; 6H), 5.48(s; 2H), 4.42(dd; J=4.8 Hz, 10.5 Hz; 2H), 3.98(d; J=9.0 Hz; 2H), 3.85(m; J=5.1 Hz, 9.0 Hz, 10.2 Hz; 2H), 3.70–3.55(m; 4H), 3.48(m; 2H), 1.55(m; 4H), 1.30(m; 76H), 0.85(t; J=6.3 Hz; 6H). TLC R$_f$=0.68 (10% ethyl acetate-hexane). FAB MS: for C$_{64}$H$_{110}$O$_6$ [MH], calcd m/z 976, found m/z 976; [MNa], calcd m/z 998, found m/z 998. Anal. Calcd for C$_{64}$H$_{110}$O$_6$: C, 78.80%; H, 11.36%. Found: C, 78.86%; H, 11.34%.

Compound 20.2c (346.6 g; 0.355 mol) is dissolved in ethyl alcohol (4.4 L) and water (0.97 L) at 40° C., and concentrated HCl (37.6%; 318 mL) is added dropwise. The system is refluxed at 80° C. overnight and cooled to room temperature. Saturated sodium bicarbonate solution (4 L) is added dropwise to obtain a final pH of 7, and the mixture is evaporated to dryness. The solid is triturated with boiling ethyl acetate (2×3.5 L). The resulting solutions are filtered through a heated sintered funnel, and the remaining final solids are discarded. The combined organic extracts are cooled to 0° C. for a few hours, leading to extensive crystallization. The solid is separated by filtration and reserved. The filtrate is concentrated to half volume and allowed to stand at 4° C. overnight. The resulting solid is combined with the previous solid, affording compound 20.3c (282 g; 0.353 mol; 99% yield based on compound 20.2c). TLC $R_f$=0.38 (60% ethyl acetate-hexane). FAB MS: for $C_{50}H_{102}O_6$ [MNa], calcd m/z 822, found m/z 822. Anal. Calcd for $C_{50}H_{102}O_6$: C, 75.13%; H, 12.86%. Found: C, 75.42%; H, 12.90%.

Compound 20.3c (50 g; 0.0626 mol) is dissolved in THF (1.63 L) at 40° C. To this clear solution is added a solution of $NaIO_4$ (54.3 g; 0.254 mol) in water (0.82 L) over the period of 40 minutes; throughout the addition the reaction temperature is maintained at 40° C. The resulting suspension is agitated at 40° C. for half an hour and then cooled to 20° C. Bromine (22 mL; 0.42 mol) is added dropwise over the period of 20 minutes. The reaction mixture is warmed to room temperature and left for 2 hours under intense stirring. Methylene chloride (2 L) and a 5% aqueous sulfuric acid solution (500 mL) are added. The organic layer is reserved and the aqueous layer is back-extracted with methylene chloride (2×1.5 L). The red organic layers are combined and treated with an aqueous saturated sodium bisulfite solution until a light yellow color is obtained (ca. 1 L of $NaHSO_3$ solution). The organic layer is washed with water (4 L) and brine (3 L), dried over anhydrous sodium sulfate, filtered and concentrated under vacuum to a white solid (64 g). The solid is dissolved in methanol (0.75 L) and treated with concentrated HCl (12 M; 50 mL). The suspension is stirred at 50° C. overnight, cooled to room temperature, neutralized with aqueous saturated $NaHCO_3$ solution (525 mL) and concentrated under vacuum. The residue is treated with warm methylene chloride (2 L) and filtered. The filtrate is dried over anhydrous sodium sulfate, filtered and concentrated under vacuum, affording a white solid (66 g). The solid is dissolved in methylene chloride (1 L), washed with a combination of water (1 L) and brine (1 L), dried over anhydrous $Na_2SO_4$ and concentrated under vacuum to a solid (43 g). The solid is recrystallized from hot hexane, affording pure compound 20.4c (32.3 g; 0.753 mol; 60% yield based on compound 20.3c). $^1$H NMR (300 MHz, $CDCl_3$): δ 3.98(dd; J=3.6 Hz, 6.3 Hz; 1H), 3.88(dd; J=3.9 Hz, 11.5 Hz; 1H), 3.82–3.70(m; 5H), 3.44(m; 1H), 1.60(m; 2H), 1.30 (br; 38H), 0.84(t; J=6.3 Hz; 3H). $^{13}$C NMR (75.4 MHz, $CDCl_3$): δ 179.94, 88.17, 80.08, 72.06, 60.71, 40.57, 38.35, 38.31, 38.26, 38.21, 38.06, 38.01, 34.61, 31.35, 22.77. IR (neat): 3466.1 (br), 2917.6 (s), 2854.1 (s), 1742.3 (m), 1460.5 (m), 1126.3 (m). TLC $R_f$=0.36 (40% ethyl acetate-hexane). FAB MS: for $C_{26}H_{52}O_4$ [M+Na] calcd m/z 45 1; found m/z 451. Anal. Calcd. For $C_{26}H_{52}O_4$ (428.69): C, 72.85%; H, 12.23%. Found: C, 73.06%; H, 12.01%.

PART IV. ASSEMBLY OF SACCHARIDES AND LIPOPHOSPHOGLYCERATE MIMETICS INTO MOENOMYCIN ANALOGS

Solid phase techniques for assembling the above-discussed acceptor, donor and lipid groups with phosphorus-containing groups are discussed hereinbelow and are illustrated in Scheme 21. In Scheme 21, the acceptor saccharide is represented by a phenyl 3,4-di-O-substituted-4-C-methyl-1-thio-β-D-glucopyranosiduronic acid, the donor molecule is represented by a phenylsulfenyl 3,4,6-tri-O-substituted-α, β-D-glucopyranoside, having a masked amine group represented by N*, and the lipophosphoglycerate mimetic moiety is represented generally by O—P(O)(OH)—OR, e.g., where R contains carboxyl and lipid groups.

Step 1. Linking Glucopyranosiduronic Acid to Rink Resin

A Rink amine resin is swelled in DMF-DCM (1:1 v/v) and washed twice with DMF. The solvent can be removed simply by pumping it out using a fritted glass tube (medium porosity). The Fmoc-protecting group of the resin is removed by treating the resin with 20% piperidine-DMF solution. The resin is then washed 4 times with low amine DMF. The glucopyranosiduronic acid (2 equiv.), HATU (2 equiv.) and DIPEA (2–4 equiv.) are individually dissolved in low amine DMF. The reagents are added to the resin in the above order. The resin is stirred with the coupling cocktail until it is negative to ninhydrin color test. The coupling cocktail is removed by vacuum filtration. The glycopyranosiduronic acid can be recovered by extracting the cocktail with EtOAc and dilute hydrochloric acid. The resin is washed 4 times with DMF, 4 times with EtOAc, and 4 times with DCM.

Step 2. Solid Phase Glycosylation Reactions—Coupling of Donor to Acceptor Residues Acceptor-loaded resin is swelled in anhydrous EtOAc. The EtOAc is removed and the resin is equilibrated twice with 20% EtOAc-DCM. The EtOAc-DCM wash solvent is removed. The donor phenylsulfenyl saccharide (4 equiv.) and $^tBu_2$Mepy (2 equiv., 4 equiv. can also be used except with 2-NPhth donors) are dissolved in 20% EtOAc-DCM. The donor/base solution is added to the resin. The reaction mixture is stirred under argon at room temperature for 5 minutes. The reaction mixture is cooled to −70° C. $Tf_2O$ (4 equiv.) is added in a dropwise manner and the reaction mixture is allowed to warm from −50° C. to −30° C. and is kept at that temperature for 3–16 hours. The reaction is then quenched with MeOH (10 equiv.) and DIPEA (10 equiv.) in DCM and the reaction mixture is allowed to warm to room temperature. Solvent is removed and the resin is washed (with 5 minutes of stirring) with DMF for 4 times, EtOAc for 4 times and DCM for 4 times.

Step 3. Reduction of Azide Group

The resin is swelled in THF-EtOH (1:1 v/v) with 10% v/v water. Trimethylphosphine-THF (4 equiv.) is added and the reaction mixture is stirred at room temperature for 3–4 hours. The reduction of azide can be confirmed with Diffuse Reflectance Infrared Fourier Transform Spectroscopy (DRIFTS). The resin is washed 4 times with THF, 4 times with DCM, and 2 times with DMF.

Step 4. Synthesis of Amides from Aminosaccharide and Carboxylic Acids

The amine loaded resin is swelled in DMF, carboxylic acid (4 equiv.), HATU (4 equiv.) and DIPEA (4 equiv.) are added. The reaction mixture is stirred at room temperature until it is negative to ninhydrin color test. The resin is washed 4 times with DMF, 4 times with EtOAc, and 4 times with DCM.

Step 4'. Synthesis of Ureas from Aminosaccharide and Isocyanates

The amine loaded resin is swelled in DMF. The DMF is removed by pumping it out using a fritted glass tube (medium pore). The resin is treated with a solution containing the isocyanate (5 eq per amine group) and triethylamine (5 eq per amine group) in DMF. The reaction mixture is stirred at RT for 4 hr or until the resin gives a negative Kaiser test. The supernatant is removed by pumping it out using a fritted glass tube (medium pore). The resin is washed twice with DMF, 4 times with EtOAc, and 4 times with $CH_2Cl_2$. (Diisopropylethylamine has also been used as a base, but is not preferred since it is immiscible with DMF.)

Step 5. Removal of Acyl (levulinoyl) Protecting Group and Reaction with Isocyanate The resin is swelled in DMF. The DMF is removed with a suction tube, and hydrazine acetate (4 equiv.) is dissolved in DMF with heating. The solution is added to the resin after it is cooled to room temperature. The reaction mixture is stirred at room temperature overnight. The resin is washed 4 times with DMF, 4 times with EtOAc, and 4 times with DCM. The resin appears very sticky on glass surface. The resin is swelled in DCM, and isocyanate (4 equiv.) and triethylamine (4 equiv.) are added. The resin will not stick to glass surface after a short time. The reaction mixture is stirred at room temperature for 4–6 hours. The resin is washed 4 times with DCM.

Step 6. Cleavage of 1-SPh Group Using Mercury Trifluoroacetate

The resin is swelled in $CH_2Cl_2$. $CH_2Cl_2$ is removed by pumping it out using a fritted glass tube (medium porosity). To 20 mg of resin (0.01 mmol) is added a solution of mercury trifluoroacetate (4 eq) in water-saturated DCM (1 mL), which is prepared by mixing DCM and water in a separatory funnel and shaking for a few minutes. The DCM layer is collected and use as prepared. The reaction mixture is stirred at 40° C. for 1 hour (using a condenser for reflux). The supernatant is removed by pumping it out using a fritted glass tube. The resin is washed 6 times with DMF and 2 times with either THF or DCM. The resin is now ready for the phosphorylation or P—R amidite coupling step.

Step 7. Solid-phase Phosphorylation (first step)

The resin is swelled in $CH_2Cl_2$. The $CH_2Cl_2$ is removed by pumping it out using a fritted glass tube (medium pore). To 20 mg of resin (0.1 mmol) in dry $CH_2Cl_2$ (1 mL), in a 2-neck round bottom flask under argon, are successively added DIPEA (25 eq) and 2-cyanoethyl diisopropylamino phosphorus chloride (25 eq). The reaction mixture is stirred at room temperature for 2 hours under argon. The supernatant is removed by pumping it out using a fritted glass tube. The resin is washed 2 times with dry $CH_2Cl_2$, 2 times with dry THF, and 2 times with dry (1:1) THF—$CH_3CN$. The resin is now ready for the "lipid" coupling step.

Step 7a. Synthesis of C5 Lipid Amidite

To a lipid compound, e.g., compound 20.4a (190 mg; 1 mmol), in dry $CH_2Cl_2$ (10 mL) under argon at room temperature, are successively added DIPEA (0.34 mL; 1.95 mmol; 1.95 eq) and 2-cyanoethyl diisopropylamino phosphorus chloride (0.25 mL; 1.1 mmol; 1.1 eq). The reaction mixture is stirred at room temperature for 45 min–1 hr (the reaction is monitored by TLC in (1:1) hexane-EtOAc). The reaction mixture is then diluted with $CH_2Cl_2$ and the organic layer is washed successively with ice cold 10% $NaHCO_3$, $H_2O$ and saturated NaCl. The organic layer is dried over sodium sulfate and concentrated on a rotary evaporator. It is then dried under vacuum using a vacuum pump for a few hours prior to using it as a crude mixture (a yellowish oil is obtained).

Step 7b. Synthesis of C12 Lipid Amidite

To a C12 lipid, e.g., compound 20.4b (144 mg; 0.5 mmol), in dry DCM (5 mL) under argon at room temperature are added successively DIPEA (0.17 mL; 0.975 mmol; 1.95 eq) and 2-cyanoethyl diisopropylamino phosphorus chloride (0.12 mL; 0.55 mmol; 1.1 eq). The reaction mixture is stirred at room temperature for 45 min to 1 hour, with the reaction monitored by TLC in hexane-EA (2:1). The reaction mixture is then diluted with DCM and the organic layer is washed successively with ice cold 10% sodium bicarbonate, water and saturated brine. The organic layer is dried over sodium sulfate and concentrated on a rotary evaporator. It is then dried under vacuum using a vacuum pump for a few hours prior to using it as the resulting mixture (yellowish oil).

Step 8. Lipid Coupling and Oxidation

The resin is swelled in THF. The THF is removed by pumping it out using a fritted glass tube (medium pore). To 20 mg of resin (0.01 mmol), in a 2-neck round bottom flask, are successively added a solution of the lipid (10 eq) in dry THF (1 mL) and a 0.5M solution of tetrazole in acetonitrile (50 eq, 1 mL). The reaction mixture is stirred at 60° C. overnight (use a condenser for reflux). After overnight stirring, the reaction mixture is cooled down to room temperature. The supernatant is removed by pumping it out using a fritted glass tube. The resin is washed 4 times with THF, and is swelled in 0.5 mL of THF. To the resin is added 1.5 mL of an iodine solution ($I_2$/THF-pyr-$H_2O$, from Perkin Elmer—Applied Biosystems, Inc.). The reaction mixture is stirred at room temperature for 10 minutes. The supernatant is removed by pumping it out using a fritted glass tube. The resin is washed 4 times with THF. The resin is now ready for the aqueous LiOH deprotection step.

Step 8a. Lipid Amidite Coupling and Oxidation

The resin is swelled in THF. The THF is removed by pumping it out using a fritted glass tube (medium pore). To the resin (20 mg; 0.01 mmol) in a two-neck round bottom flask is added a premixed solution of lipid amidite, e.g., C5 or C12, (crude, 15 eq) in dry THF (1 mL) and a 0.5M solution of tetrazole in acetonitrile (1 mL; 50 eq). The above reagents are premixed for 2–15 minutes prior to addition to the resin. The reaction mixture is stirred at 60° C. overnight using a condenser for reflux. After overnight stirring, the reaction mixture is cooled down to room temperature. The supernatant is removed by pumping it out using a fritted glass tube. The resin is washed 4 times with THF, and is swelled in THF (0.5 mL). To the resin is added 1.5 mL of an iodine solution ($I_2$/THF-pyr-$H_2O$, from Perkin Elmer—Applied Biosystems, Inc.). The reaction mixture is stirred at room temperature for ten minutes. The supernatant is removed by pumping it out using a fritted glass tube. The resin is washed 4 times with THF. The resin is now ready for the aqueous LiOH deprotection step.

Step 8b. Salicylic Acid Coupling and Oxidation.

The resin is swelled in $CH_2Cl_2$. The $CH_2Cl_2$ is removed by pumping it out using a fritted glass tube (medium pore). To the resin (20 mg; 0.01 mmol) in dry $CH_2Cl_2$ (1 mL) are successively added DIPEA (25 eq) and 2-chloro-4H-1,3,2-benzodioxaphosphorin-4-one (25 eq) dissolved in dry $CH_2Cl_2$ (1 mL). The reaction mixture is stirred at room temperature for 2 hours. The supernatant is removed by pumping it out using a fritted glass tube. The resin is washed 4 times with $CH_2Cl_2$ and 4 times with THF. The resin is then swelled in THF (0.5 mL). To the resin is added 1.5 mL of an iodine solution ($I_2$/THF-pyr-$H_2O$, from Perkin Elmer—Applied Biosystems, Inc.). The reaction mixture is stirred at room temperature for ten minutes. The supernatant is removed by pumping it out using a fritted glass tube. The resin is washed 4 times with THF. The resin is now ready for the nonaqueous LiOH deprotection step.

Step 9. Cleavage of Cyanoethyl, Methyl Ester and Acetyl Groups

The resin is swelled in THF. The THF is removed by pumping it out using a fritted glass tube (medium pore). To 20 mg of resin (0.01 mmol) in THF-MeOH (1:1) (2 mL) is added a 0.4M aq LiOH solution (10 eq, 0.25 mL) [2 eq/group to be cleaved]. The reaction mixture is stirred at room temperature for 2–3 hours. After overnight stirring, the supernatant is removed by pumping it out using a fritted glass tube. The resin is washed 3 times with MeOH, 3 times with THF-MeOH (1:1), and 4 times with THF. The resin in now ready for the non-aqueous LiOH deprotection step.

Step 9a. Cleavage of Benzoyl Group (final deprotection)

The resin is swelled in THF. The THF is removed by pumping it out using a fritted glass tube (medium pore). To 20 mg of resin (0.01 mmol) is added a solution of LiOH (10 eq) in THF-MeOH (1:1) (2 mL). The reaction mixture is stirred at room temperature overnight. After overnight stirring, the supernatant is removed by pumping it out using a fritted glass tube. The resin is washed three times with 20% aqueous THF, three times with MeOH, three times with THF-MeOH (1:1), three times with THF, and four times with $CH_2Cl_2$. The resin is now ready for TFA cleavage.

Step 10. Cleavage of Product from Resin

The resin is swelled in $CH_2Cl_2$. The $CH_2Cl_2$ is removed by pumping it out using a fritted glass tube (medium pore). To 20 mg of resin (0.01 mmol) is added 20% TFA/$CH_2Cl_2$ (2 mL). The reaction mixture is stirred at room temperature for 30 minutes. The resin is filtered off and the supernatant is transferred to a pre-weighed round bottom flask. The resin is washed twice with $CH_2Cl_2$, the filtrate and washes are pooled and concentrated under vacuum, and the residue is taken up in dioxane, isopropanol or 20% DMSO/water and stirred for 30 min with pre-washed H+ resin. The resin is filtered off and washed a few times with the solvent used for exchange. The filtrate is then concentrated under vacuum on a rotary evaporator. The sample is analyzed by LC-MS after dissolution in methanol.

Automated Procedure for Synthesis of Moenomycin Library Analogs

This procedure can be carried out simultaneously on two, 48-position Combitec reaction blocks on a TECAN (Switzerland) liquid handling platform. The reaction blocks are assembled as described by TECAN and fitted with 5 mL reaction vessels.

One Rink amide-bound disaccharide (pictured below) is illustrated for this particular procedure.

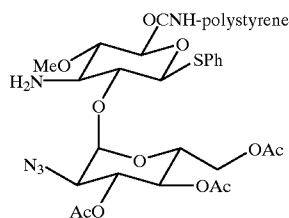

Phenyl 2-O-(2-azido-2-deoxy-3,4,6-tri-O-acetyl-α-D-glucopyranosyl)-(1→2)-3-amino-3-deoxy-4-methoxy-1-thio-β-D-glucopyranosiduronic acid This disaccharide is functionalized with three carboxylic acids and one isocyanate on the acceptor amine, and four different carboxylic acids at the reduced donor azide. In addition, the anomeric position of the sugar is functionalized as either a C5-phospholipid or a phosphosalicylate. Overall, 96 different products and intermediates are isolated using this scheme.

Stirring is conducted magnetically using 10 mm stir bars in each reaction flask and a 48-position stir plate.

All washes are performed with 5 minutes of stirring between solvent addition and removal.

Anhydrous grades of dichloromethane (DCM), tetrahydrofuran (THF), ethanol (EtOH) and methanol (MeOH) are purchased from Aldrich for use in these syntheses. Low amine content N,N-dimethylformamide (DMF) is purchased from PerSeptive Biosystems.

Procedure 1.5 g of the resin-bound disaccharide is swelled in 100 mL of 4:1 DCM/THF for 30 minutes. 1.0 mL of this slurry (15 mg, 0.007 mmol, 1×) is then robotically dispensed into each position of the 2 reaction blocks. 1 mL of the solvent mixture is then added to wash the resin down into the reaction vessels.

Each position is then aspirated, washed with 2×2 mL THF and purged with argon for 60 seconds.

a) 0.5 ml of a 0.057M solution of each carboxylic acid (0.028 mmole, 4×, in DMF) is then added. This is followed by the addition of 0.75 ml of 0.037M HATU (0.028 mmole, 4×, in DMF) and 0.75 ml of 0.037M diisopropylethylamine (0.028 mmole, 4×, in DMF).

b) 1 mL of a 1.0 M solution of the isocyanate in freshly distilled THF is then added, followed by 1 mL of a 0.5M triethylamine solution in THF.

After stirring the reaction mixtures for four hours, each vessel is aspirated and washed with 4×2 mL THF and 2×2 mL DMF.

After the addition of 1.1 mL of 9:2 EtOH/Water to every vessel, 0.9 mL of 0.032M trimethylphosphine (0.028 mmole, 4×, in THF) is added.

The reaction mixtures are then stirred for 4 hours before aspiration of the solvent.

Each vessel is then washed with 4×2ml THF and 2×2 ml DMF.

0.5 ml of a 0.057M solution of each carboxylic acid (0.028 mmole, 4×, in DMF) is then added. This is followed by the addition of 0.75 ml of 0.037M HATU (0.028 mmol, 4×, in DMF) and 0.75 ml of 0.037M diisopropylethylamine (0.028 mmol, 4×, in DMF).

The reaction mixtures were stirred overnight at room temperature before aspiration. Each was then washed with 4×2 mL DMF and 2×2 mL DCM.

After the addition of 2 mL of 0.014M mercury(II) trifluoroacetate (0.028M, 4×) in water saturated DCM to the appropriate wells, the mixtures were stirred at 40° C. for 1 hour.

After aspiration, the vessels are washed with 4×2 mL DMF and 2×2 mL DCM. Each vessel is then purged with argon for 60 seconds.

Procedure for C5 Lipid Attachment 2 mL of a 0.053M isopentyl amidite derived from compound 20.4a (0.105 mmole, 15×)/0.25M tetrazole solution in 1:1 THF/acetonitrile is then added to the appropriate vessels. The reaction mixtures are then stirred overnight at 60° C.

Each flask is then aspirated and washed with 4×2 mL THF.

2 mL of iodine solution ($I_2$/Pyridine/THF/$H_2O$) is then added to the phosphorylated resins and each is stirred for 10 minutes.

Each vessel is then aspirated and washed with 4×2 mL THF.

2.0 mL of 0.035M lithium hydroxide (LiOH) in 4:4:1 THF/MeOH/Water (0.07 mmol, 10×) is then added to all of the phosphorylated resins and each is stirred for 2.5 hours at room temperature.

After washing with 3×2 mL 1:1 THF/MeOH and 2×2 mL THF, 2.0 ml of 0.035M LiOH in 1:1 MeOH/THF (0.07 mmol, 10×) is added to all of the vessels and the mixtures are stirred overnight.

The mixtures are then aspirated and washed with 3×2 mL 1:1 THF/MeOH, 4×2 mL THF and 3×2 mL anhydrous DCM.

Each disaccharide is then cleaved from the resin with 30 minutes of stirring in 2.5 mL of 20% trifluoroacetic acid in DCM.

The product solutions are then transferred to polyethylene microtiter plates before solvent evaporation in a Speedvac.

After drying, the products are dissolved in 20% aqueous DMSO and passed through a column of Amberlite proton exchange resin.

The resulting solutions are analyzed by LC-MS on a Perkin Elmer API100.

Procedure for Cyclic Salicylate Attachment 1 mL of 0.175M diisopropylethylamine (0.105 mmol, 15×, in DCM) and 1 mL of 0.175M 2-chloro-H-2,1,3-benzodioxaphosphorin-4-one (0.105 mmol, 15×, in DCM), available from Aldrich Chemical Co., is then added to the appropriate vessels. The reaction mixtures are then stirred at room temperature for 2 hours.

Each flask is then aspirated and washed with 4×2 ml DCM and 2×2 ml THF.

Each sample is oxidized with 2 mL iodine solution ($I_2$/Pyr/THF/$H_2O$) for ten minutes.

After being washed with 4×2 mL THF, every vessel is treated with 2.0 mL of 0.035M LiOH in 1:1 MeOH/THF (0.07 mmol, 10×). The reactions are stirred overnight.

The mixtures are then washed with 3×2 mL 1:1 THF/MeOH, 4×2 mL THF and 3×2 mL anhydrous DCM.

Each disaccharide is then cleaved from the resin with 30 minutes of stirring in 2.5 mL of 20% trifluoroacetic acid in DCM.

The product solutions are then transferred to polyethylene microtiter plates before solvent evaporation in a Speedvac.

After drying, the products are dissolved in 20% aqueous DMSO and passed through a column of Amberlite proton exchange resin.

The resulting solutions are analyzed by LC-MS on a Perkin Elmer API100.

Mass Specrtra

Figure 20A:
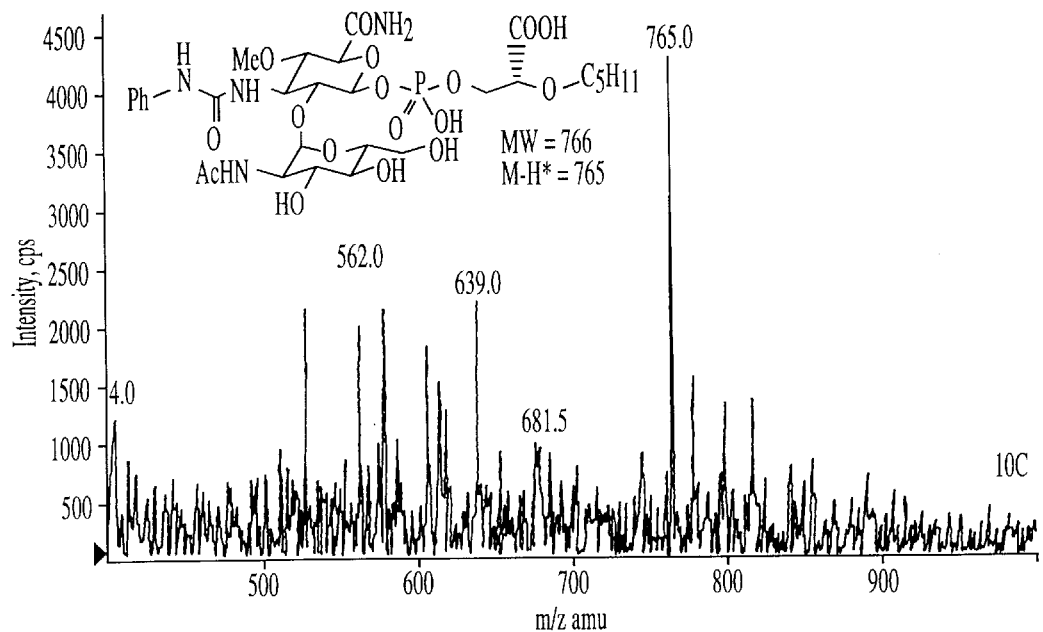
FIG. 20 depicts mass spectra for two moenomycin analogs prepared according to principles of the present invention.
Figure 20B:
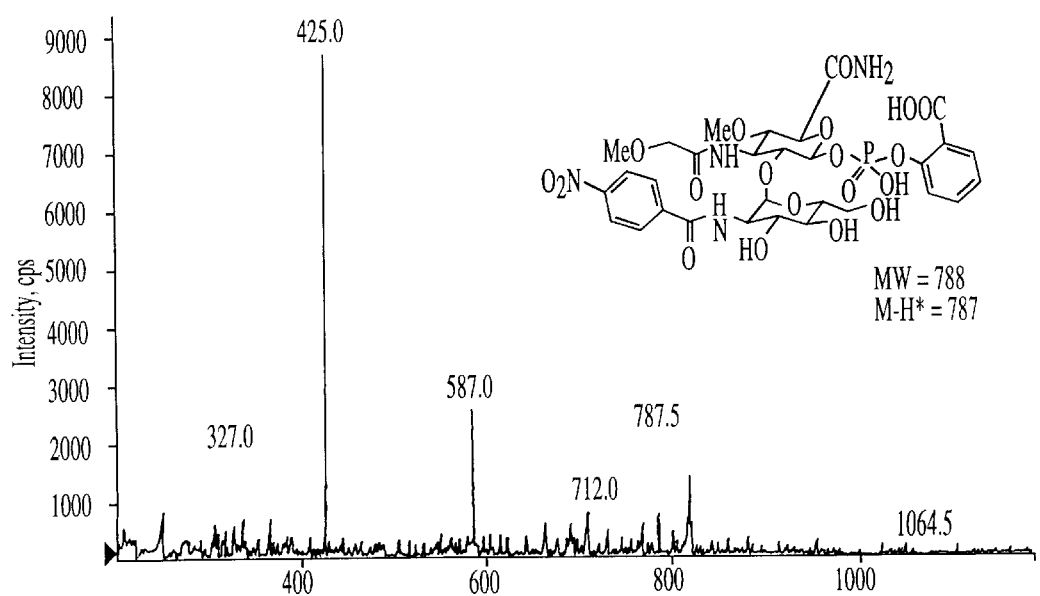

Representative mass spectra (Fab) for moenomycin analogs of the invention, which were constructed as described hereinabove, are shown in FIG. 20.

PART V. SCREENING OF MOENOMYCIN ANALOGS FOR ANTIMICROBIAL ACTIVITY

The following procedures for conducting an assay of bacterial inhibition by a moenomycin analog of the present invention can be performed.

Bacteria. All organisms are grown in a universal rich media to minimize media effects on the inhibition assay. All bacteria are demonstrated to grow in Brain Heart Infusion (BHI) media (Difco, Detroit, Mich.) supplemented with 0.1% Casamino Acids (CAA) (Difco). The following organisms are used in primary screening:

*Enterococcus faecium* (ATCC 49624)
*Enterococcus faecalis* (ATCC 29212)
*Staphylococcus aureus* (ATCC 29213)
*Staphylococcus epidermidis* (ATCC 12228)
*Streptococcus pneumonia* (ATCC 49150)
*Escherichia coli* (ATCC 25922)
*Acinetobacter anitratus* (ATCC 43498)

The bacteria are streaked for isolation from frozen glycerol stocks onto BHI/CAA plates containing 1.5% Bacto-agar (Difco). An isolated colony from each strain is used to inoculate 5 mL of BHI/CAA media and allowed to grow overnight at 37° C. with shaking. The exception is with Streptococcus strains, which are grown in a candle jar at 37° C. without shaking. After overnight growth, the organisms are diluted 1:100 and allowed to incubate until they reach early to mid-logarithmic growth ($OD_{600}$≈0.5). The cells are diluted 100 fold in BHI/CAA containing 0.7% agar maintained at 50° C. to a cell density of approximately $5 \times 10^5$ colony forming units (CFU) permL. The agar slurry is poured into an 86 mm×128 mm assay plate (Nunc), which has the dimensions of a 96-well plate, and allowed to solidify for at least 30 minutes. Streptococcus strains are diluted in BHI/CAA media without agar and 200 µl aliquoted to each well of a 96-well assay plate.

Test Compounds. The test compounds are solubilized in sterile 20% DMSO/water to a concentration of approximately 1–5 mg/ml, aseptically aliquoted among several sterile "daughter" plates and frozen at −20° C. Daughter plates are thawed at room temperature or 37° C. just prior to assay.

Lawn Assay. A sterilized 96-well replicating device (Boekel) is inserted into the daughter plate and used to deliver the test compound to either a 96-well plate containing Streptococcus, or an agar plate imbedded with bacteria. The replicator pierces the agar and is removed vertically to prevent damage to the agar surface. The appearance of zones of inhibition is monitored after 15 to 24 hr. growth at 37° C. Similarly, Streptococcus inhibition is monitored by no observable turbidity in the wells of the 96-well plate after 24–48 hr. growth.

A control plate containing dilutions of antibiotic standards is run at the time of each assay with each organism. The control antibiotics are Ampicillin, Vancomycin and Moenomycin. Control samples are aliquoted in duplicate in a 96-well array. Each antibiotic is tested at eight serial two fold dilutions. Antibiotic concentrations vary from 10 mg/ml to 0.001 mg/ml.

MIC Assay. Putative actives in the Lawn assay are further screened to determine the minimum inhibitory concentrations (MIC) of each compound for each organism affected. Test compounds are serially diluted in 20% DMSO/water and added to 96-well plates in a volume of 5 µl. Each bacterium, grown as described above and diluted in broth without agar, is added to the diluted compound in a volume of 200 µl. The range of concentrations used for each compound in the MIC assay is based on the potency implied by the size of the zone of inhibition in the lawn assay. Each compound is tested at five serial dilutions, ranging anywhere from 1:40 up to the maximium dilution necessary to alleviate the antimicrobial effect. The effect of the test compound on bacterial growth is measured after 18 hrs of growth at 37° C. by determining the turbidity of the medium at 600 nm or by visual inspection. The MIC is defined as the lowest concentration of compound necessary to completely inhibit bacterial growth.

Peptidoglycan Synthesis Assay. The peptidoglycan polymerization assay is adapted from that described by Mirelman, et al. [*Biochemistry* 15:1781–1790 (1976)] and modified by Allen, et al. [*FEMS Microbiol. Lett*. 98:109–116 (1992)]. *E. coli*. (ATCC #23226) are permeabilized with ether according to Mirelman, et al.(1976), and Maas and Pelzer [*Arch. Microbiol*., 130:301–306 (19__)], permitting exogenously added radiolabelled and non-radiolabelled cell wall precursors to penetrate the bacterial cell wall. Screening quantities of UDP muramyl-pentapeptide (UDP-N-acetylmuramyl-L-Ala-D-glu-meso-diaminopimelyl-D-ala-D-ala) are isolated by boiling from an aqueous extract of *B. cereus* (ATCC #11778) according to published preparative (Kohlrausch and Holtje, *FEMS Microbiol. Lett*. 78:253–258 (1991) and analytical HPLC techniques (Kohlrausch, et al., *J. Gen. Microbiol*. 153:1499–1506 (1989). Bacterial protein is determined by the method of Bradford [*Anal. Biochem*. 72: 248 (1976)].

Polymerization assays are conducted in 96-well filter-bottom plates (Millipore GF/C-cat. # MAFC NOB 10). A Tecan Genesis 150 robot is programmed for all subsequent liquid handling steps. In a final assay volume of 100 μL, each well contains: 50 mM Tris-HCl (pH 8.3); 50 mM $NH_4Cl$; 20 mM $MgSO_4.7\,H_2O$; 10 mM ATP (disodium salt); 0.5 mM β-mercaptoethanol; 0.15 mM D-aspartic acid; 0.001 mM UDP-N-acetyl [$^{14}$C-]-D-glucosamine (DuPont/N.E.N.—265–307 mCi/mmol); 0.05 mM UDP-MurNAc-pentapeptide, 100 ug/ml tetracycline and 50 ug/well ether-treated bacterial protein. Novel test compounds are solubilized in 10% DMSO/water and screened at a final assay concentration of 10 ug/ml. With the exception of radiolabeled and isolated native pentapeptide, all remaining biochemicals are purchased from Sigma Chemical or Fisher Scientific.

Assay buffer (10 μL), ATP (20 μL), UDP pentapeptide (10 μL) and $^{14}$C-UDP-GlcNAc (20 μL) are added to all wells, followed by either test compound, reference standard or buffer vehicle (20 μL). The reactions are then started by adding 20 μL aliquots of bacterial protein prepared in assay buffer into each well. Plates are covered, mixed for 30 sec., then incubated at 37° C. for 120 min. Ice cold 20% TCA (100 μL) is added to each well, the plates are gently mixed (60 sec), then refrigerated (4° C.) for 30 min to assure precipitation of all peptidoglycan.

The plates are placed under vacuum filtration on a Millipore manifold, flitered, and washed 3–4 times with 200 μL/well of 10% TCA. Optiphase scintillation cocktail (30 μL/well) is added, then the plates are incubated overnight prior to counting in a Wallac Microbeta. Percent inhibition of incorporation of $^{14}$C-label into peptidoglycan is computed from control (total incorporation) and background (blank) wells containing 300 μg/ml of vancomycin or 100 μg/ml of moenomycin, which completely inhibit incorporation of radiolabel. All wells are arrayed in duplicates, which usually vary by <20%. Concentration-response curves for reference standards are arrayed on each plate as positive controls (IC50 for inhibition of incorporation: vancomycin=2.4+/−0.2 μg/ml; moenomycin=0.04+/−0.005 μg/ml).

Several preferred aspects of the present invention have been discussed hereinabove for purposes of illustration and clarification. It is readily apparent to one skilled in the art that certain obvious improvements and modifications of the present invention can be practiced without departing from the scope of the appended claims.

REFERENCES:

1. Scherkenbeck, J., et al., *Tetrahedron*, 49:3091–3100 (1993)
2. Heuer, M. et al., *Tetrahedron*, 50:2029–2045 (1994)
3. Fehlhaber, H-W., et al., *Tetrahedron*, 46:1557–1568 (1990)
4. Hessler-Klintz, M., et al., *Tetrahedron*, 49:7667–7678 (1993)
5. Welzel, P., et al., *Tetrahedron*, 43:585–598 (1987)
6. Moller, R. et al., *Tetrahedron*, 49:1635–1648 (1993)
7. Marzian, S., et al., *Tetrahedron*, 50:5299–5308 (1994)
8. Luning, J., et al., *Tetrahedron Letters*, 35:1859–1862 (1994)
9. Donnerstag, A., et al., *Tetrahedron*, 51:1931–1940 (1995)
10. Welzel, P., et al., *Carbohydrate Research*, 126:C1–C5 (1984)
11. Ritzeler, O., et al., *Tetrahedron*, 53:1665–1674 (1997a)
12. Ritzeler, O., et al., *Tetrahedron*, 53:1675–1694 (1997b)
13. Range, G., et al., *Tetrahedron*, 53:1695–1706 (1997)

What is claimed is:

1. A method of synthesizing at least one compound having the formula 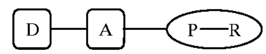 wherein D represents a monosaccharide or disaccharide, A represents a monosaccharide, and P—R represents a lipophosphoglycerate mimetic group that is not a phospholipid group of moenomycin A or a saturated form thereof, said method comprising the steps of:

(a) covalently linking an acceptor monosaccharide (A) to a support by forming a carboxylate or carboxyamide linkage between the C6 carbon of A and the support, with A substituted at its anomeric carbon with a thiophenyl group;

(b) covalently linking the anomeric carbon of a donor saccharide (D) via an O-glycosidic linkage to the C2 carbon of A to form a D-A moiety linked to the support;

(c) coupling a lipophosphoglycerate mimetic group (P—R) to the anomeric position of the A residue of the D-A moitty to form a D-A-P-R moiety linked to the support; and (d) cleaving the D-A-P-R moiety from the support, thereby affording said at least one compound.

2. The method of claim 1, further comprising forming an amide, carbamate, urea, sulfonamide, substituted amine, ester, carbonate or sulfate functionality at the C3 position of A before or after performing step (b).

3. The method of claim 1, further comprising forming an amide, carbamate, urea, sulfonamide, substituted amine, ester, carbonate or sulfate functionality at the C2 position of D before or after performing step (b).

4. The method of claim 1, further comprising forming the P—R group prior to performing step (c).

5. The method of claim 1, further comprising removing protecting groups from the D-A-P-R moiety prior to performing step (d).

6. The method of claim 1, wherein the support is selected from the group consisting of a resin having a photo- or acid-cleavable linker, silica, controlled porosity glass, polystyrene, polyethylene glycol, and grafted polymers.

* * * * *